(12) United States Patent
Dugar et al.

(10) Patent No.: US 9,975,869 B2
(45) Date of Patent: May 22, 2018

(54) ANALOGUES OF EPICATECHIN AND RELATED POLYPHENOLS

(71) Applicant: Sphaera Pharma Pvt. Ltd., Haryana (IN)

(72) Inventors: Sundeep Dugar, Haryana (IN); Dinesh Mahajan, Haryana (IN); Kumar Santosh Rai, Haryana (IN); Sarbjit Singh, Haryana (IN); Ishwar Rakesh Patil, Haryana (IN)

(73) Assignee: SPHAERA PHARMA PVT. LTD., Haryana (IN)

( * ) Notice: Subject to any disclaimer, the term of this patent is extended or adjusted under 35 U.S.C. 154(b) by 0 days. days.

(21) Appl. No.: 14/780,214

(22) PCT Filed: Apr. 4, 2014

(86) PCT No.: PCT/IN2014/000213
§ 371 (c)(1),
(2) Date: Sep. 25, 2015

(87) PCT Pub. No.: WO2014/162320
PCT Pub. Date: Oct. 9, 2014

(65) Prior Publication Data
US 2016/0039781 A1 Feb. 11, 2016

(30) Foreign Application Priority Data

Apr. 4, 2013 (IN) .................... 3104/DEL/2012

(51) Int. Cl.
*C07D 311/62* (2006.01)
*C07D 311/60* (2006.01)
*C07C 45/71* (2006.01)
*C07C 45/72* (2006.01)
*C07D 311/54* (2006.01)
*C07D 405/12* (2006.01)
*A23L 33/10* (2016.01)

(52) U.S. Cl.
CPC ............ *C07D 311/62* (2013.01); *A23L 33/10* (2016.08); *C07C 45/71* (2013.01); *C07C 45/72* (2013.01); *C07D 311/54* (2013.01); *C07D 311/60* (2013.01); *C07D 405/12* (2013.01)

(58) Field of Classification Search
CPC ......... A23L 1/00; C07C 45/71; C07D 311/54; C07D 311/60; C07D 311/62; C07D 405/12
USPC ................. 549/398, 403, 404, 406
See application file for complete search history.

(56) References Cited

U.S. PATENT DOCUMENTS

| | | | |
|---|---|---|---|
| 2010/0048920 A1* | 2/2010 | Romanczyk, Jr. ...... | C07C 41/18 549/399 |
| 2010/0168221 A1* | 7/2010 | Lee ........................ | A61K 36/15 514/456 |
| 2010/0266523 A1* | 10/2010 | Vercauteren .......... | A23L 1/3002 424/78.03 |

FOREIGN PATENT DOCUMENTS

| | | | |
|---|---|---|---|
| CN | 102503924 | * | 6/2012 |
| WO | WO2013/020979 | * | 2/2013 |
| WO | WO2013/022846 | * | 2/2013 |

OTHER PUBLICATIONS

Peng et al, Deuterium Labelling of theaflavin, Journal of Labelled Compounds and Radiopharmaceuticals, 2009, 52(8), p. 312-315.*
Nel et al, The novel flavan-3-ol, (2R,3S)-guibourtinidol and its diastereomers, Phytochemistry 52, 1999, p. 1153-1158.*
Smith et al, 5-Deoxyflavan-3-ol-based proanthocyanidins with antinutritional and antimicrobial properties from the forage legume Acaciella angustissima, Journal of Applied Botany and Food Quality 84, 2011, p. 142-150.*
Fukumitsu, In fluences of adrenochrome derivatives and flavonoids on chline acetylase and histidine decarboxylase, Taishitsu Igaku Kenkyusho Hokoku, 1960,11, p. 137-61, abstract page (p. 2).*
Shadkami et al, Analysis of catechins and condesed tannins by thermally assisted hydrolysis/methylation-GC/MS and by a novel two step methylation, Journal of Analytical and Applied Pyrolysis,85(1+2), p. 54-65, abstract page (1 page).*
Bergot et al, Anthocyanins and related compounds.V. Formation of bisflavenylidenes from flavones by reductive dimerization, Tetrahedron, 1965, 21(3), p. 657-61, 1 page of abstract.*

* cited by examiner

*Primary Examiner* — Taylor V Oh
(74) *Attorney, Agent, or Firm* — Foley & Lardner LLP

(57) ABSTRACT

The present invention provides novel analogs of epicatechin and related polyphenols, their variously functionalized derivatives, process for preparation of the same, composition comprising these compounds and their method of use.

11 Claims, No Drawings

ANALOGUES OF EPICATECHIN AND RELATED POLYPHENOLS

FIELD OF THE INVENTION

The present invention provides novel analogues of epicatechin and related polyphenols, their variously functionalized derivatives, process for preparation of the same, composition comprising these compounds and their method of use.

BACKGROUND OF THE INVENTION

Polyphenolic natural products are of current interest because of their various biological activities, their occurrence in foodstuffs, and hence their relevance for human health. Polyphenolic natural products have two or more hydroxyl groups on their aromatic rings.

Representative examples include: (−)-epiafzelechin, (+)-catechin, (−)-epicatechin, (−)-gallocatechin, (−)-epigallocatechin, their respective 3-gallate esters, as well as two 3-(30-methyl)-gallate esters, herein referred to collectively as "catechins". (+)-Catechin, (−)-catechins, (+)-epicatechin and (−)-epicatechin are flavon-3-ols.

These flavonols are present in the human diet in chocolate, fruits, vegetables and wine and have found use in the treatment of acute coronary syndromes, including but not limited to myocardial infarction and angina; acute ischemic events in other organs and tissues, renal injury, renal ischemia and diseases of the aorta and its branches; injuries arising from medical interventions, including but not limited to coronary artery bypass grafting (CABG) procedures and aneurysm repair; cancer; and metabolic diseases, diabetes mellitus and other such disorders.

Though such polyphenols including catechins and epicatechin are used widely, they have certain drawbacks such as low potency, undesirable pharmacodymanics and pharmacokinetic profile. Hence there is a need to improve the potency, pharmacodynamics and pharmacokinetic profiles of the polyphenols.

One of the means to achieve such an effect is to have new analogues of epicatechin. The analogues of polyphenols may be used, to reduce or eliminate metabolites, increase the half-life of the parent drug, decrease the number of doses needed to achieve a desired effect, and/or create a more effective and/or a safer drug.

Object of the Invention

An object of the invention is to provide novel analogues of polyphenols and a process of preparation thereof.

SUMMARY OF THE INVENTION

The present invention is related to novel analogues of polyphenols of the formula (I).

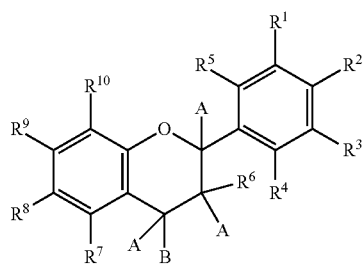

Wherein,
A is independently deuterium, hydrogen, alkyl, F, Cl
B is independently A or hydroxyl; $OR^{11}$, $NR^{11}R^{12}$
$R^1$ to $R^{10}$ are independently hydrogen; deuterium, $NH_2$, F, Cl, hydroxyl, alkoxy, lower acyclic or cyclic alkyl, lower acyclic or cyclic acyl, —CO—$OR_{11}$, —OCO—$OR_{11}$, —CO—$NR_{11}R_{12}$, —$COR_{11}$, —$CR_{11}R_{12}$, —O—CO—$R_{11}$, —$CR_{11}R_{12}$, —O—CO—$NR_{11}R_{12}$, $OCONHCHR^{11}R^{12}$, —$OCR_{11}R_{12}$, —O—CO—$R_{11}R_{12}$, —CO-aminoacid; or —CO-hydroxyacid; which may be optionally substituted with lower alkyl, acyl, alkoxy, $OR^{11}$, $NR^{11}R^{12}$, $COOR^{11}$, $CONR^{11}R^{12}$, $OCOR^{11}R^{12}$, $OCONR^{11}R^{12}$, $OSO_3R^{11}$, $OSO_2NR^{11}R^{12}$, $NR^{11}SO_2NR^{12}$, $NR^{11}SO_3R^{12}$;

When any two adjacent $R^1$ to $R^{10}$ are either OH or $NHR^{11}$, these may be additionally be joined together by a $CR^{11}R^{12}$, —(C=O)$_n$—, —CO(CH$_2$)$_n$—, —C=S, C=$NR^{12}$ or —OSO$_3$—; wherein n−1 to 2, $R^{11}$ and $R^{12}$ are independently hydrogen, OH, halo, $C_{1-6}$ alkyl aryl, alkaryl, arylalkyl, substituted alkyl, which may be straight, branched chain or cyclic, $C_{1-6}$ alkoxy which may be straight, branched chain or cyclic, $COOR_{13}$, $CH_2COOR_{13}$, $C(R^{13})_2OCOR^{13}$, $C(R^{13})_2OCOOR^{13}$, $C(R^{13})_2)OCON(R^{13})_2$, $C(R^{13})_2N(R^{13})COOR^{13}$ or haloalkyl, aryl, substituted aryl, or $R^{11}$ and $R^{12}$ taken together with the atoms to which they may attach to form a 5- to 7-member ring optionally incorporating one or two ring heteroatoms chosen from N, O, or S, which is optionally substituted with further substituents
or A and $R^6$ may form an oxime;

$R^{13}$ is independently hydrogen, lower straight or branched alkyl, substituted or unsubstituted aryl or benzyl when two $R^{13}$ groups are present on the same atom; they may be joined to form a 3 to 6 membered ring;

Where substitution at C2 and C3 of pyran ring is always cis (+) or cis (−) or mixture of two. In other words, absolute configuration at C2 and C3 of pyran ring may either have RR or SS stereochemistry or a racemic mixture of RR and SS.

DETAILED DESCRIPTION OF THE INVENTION

Accordingly, the present invention is related to novel analogues of polyphenols of the formula (I),

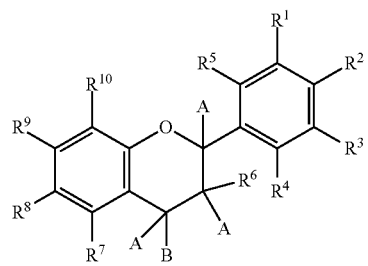

Formula I

Wherein,
A is independently deuterium, hydrogen, alkyl, F, Cl
B is independently A or hydroxyl; $OR^{11}$, $NR^{11}R^{12}$
$R^1$ to $R^{10}$ are independently hydrogen; deuterium, $NH_2$, F, Cl, hydroxyl, alkoxy, lower acyclic or cyclic alkyl, lower acyclic or cyclic acyl, —CO—$OR_{11}$, —OCO—$OR_{11}$, —CO—$NR_{11}R_{12}$, —$COR_{11}$, —$CR_{11}R_{12}$, —O—CO—$R_{11}$, —$CR_{11}R_{12}$, —O—CO—$NR_{11}R_{12}$, $OCONHCHR^{11}R^{12}$, —$OCR_{11}R_{12}$, —O—CO—$R_{11}R_{12}$, —CO-aminoacid; or —CO-hydroxyacid; which may be optionally substituted with lower alkyl, acyl, alkoxy, $OR^{11}$, $NR^{11}R^{12}$, $COOR^{11}$, $CONR^{11}R^{12}$, $OCOR^{11}R^{12}$, $OCONR^{11}R^{12}$, $OSO_3R^{11}$, $OSO_2NR^{11}R^{12}$, $NR^{11}SO_2NR^{12}$, $NR^{12}SO_3R^{12}$;

When any two adjacent $R^1$ to $R^6$ are either OH or $NHR^{11}$, these may be additionally be joined together by a $CR^{11}R^{12}$, $-(C=O)_n-$, $-CO(CH_2)_n-$, $-C=S$, $C=NR^{12}$ or $-OSO_3-$; wherein n=1 to 2, $R^{11}$ and $R^{12}$ are independently hydrogen, OH, halo, alkyl, aryl, alkaryl, arylalkyl, substituted alkyl, which may be straight, branched chain or cyclic, alkoxy which may be straight, branched chain or cyclic, $COOR_{13}$, $CH_2COOR_{13}$, $C(R^{13})_2OCOR^{13}$, $C(R^{13})_2OCOOR^{13}$, $C(R^{13})_2OCON(R^{13})_2$, $C(R^{13})_2N(R^{13})COOR^{13}$ or haloalkyl, aryl, substituted aryl, or $R^{11}$ and $R^{12}$ taken together with the atoms to which they may attach to form a 5- to 7-member ring optionally incorporating one or two ring heteroatoms chosen from N, O, or S, which is optionally substituted with further substituents or A and $R^6$ may form an oxime;

$R^{13}$ is independently hydrogen, lower straight or branched alkyl, substituted or unsubstituted aryl or benzyl, when two $R^{13}$ groups are present on the same atom, they can be joined to form a 3 to 6 membered ring;

Where, substitution at C2 and C3 of pyran ring is always cis (+) or cis (−) or mixture of two. In other words, absolute configuration at C2 and C3 of pyran ring may either have RR or SS stereochemistry or a racemic mixture of RR and SS.

The novel analogues of polyphenols of the present invention of Formula I that may also be represented by compounds of Formula II;

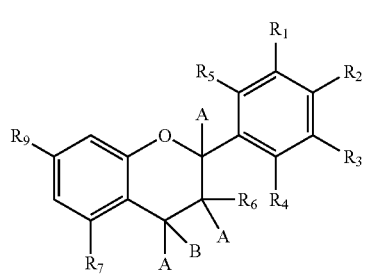

Formula II wherein

A is independently deuterium, hydrogen, alkyl, F, Cl;

B is independently A or hydroxyl; $OR^{11}$, $NR^{11}R^{12}$;

$R_1$ to $R_7$ are $R_9$ are independently; H, D, $NH_2$, F, Cl, hydroxyl, $-CO-OR_{11}$, $-CO-NR_{11}R_{12}$, $OCONHCHR^{11}R^{12}$, $-COR_{11}$, $-CR_{11}R_{12}$, $-O-CO-R_{11}$, $-CR_{11}R_{12}$, $-O-CO-NR_{11}-R_{12}$, $-OCR_{11}R_{12}$, $-O-CO-R_{11}R_{12}$;

$R^{11}$ and $R^{12}$ are independently hydrogen, OH, halo, $C_{1-6}$ alkyl, aryl, alkaryl, arylalkyl, substituted alkyl, which may be straight, branched chain or cyclic, $C_{1-6}$ alkoxy which may be straight, branched chain or cyclic, $COOR_{13}$, $CH_2COOR_{13}$, $C(R^{13})_2OCOR^{13}$, $C(R^{13})_2OCOOR^{13}$, $C(R^{13})_2OCON(R^{13})_2$, $C(R^{13})_2N(R^{13})COOR^{13}$ or haloalkyl, aryl, substituted aryl, or $R^{11}$ and $R^{12}$ taken together with the atoms to which they may attach to form, a 5- to 7-member ring optionally incorporating one or two ring heteroatoms chosen from N, O, or S, which is optionally substituted with further substituents or A and $R^6$ may form an oxime;

$R^{13}$ is independently hydrogen, lower straight or branched alkyl, substituted or unsubstituted aryl or benzyl, when two $R^{13}$ groups are present on the same atom, they can be joined to form a 3 to 6 membered ring;

Where substitution at C2 and C3 of pyran ring is always cis (+) or cis (−) or mixture of two. In other words, absolute configuration at C2 and C3 of pyran ring may either have RR or SS stereochemistry or a racemic mixture of RR and SS.

Compounds of the Present Invention:

The compounds of the present invention are illustrated but not limited to the examples as provide in Table 1.

TABLE 1

Illustrative Compounds of the present invention

| SPR No | Structure | Chemical name | Molecular Formula | Mol. Weight |
|---|---|---|---|---|
| 1001 | 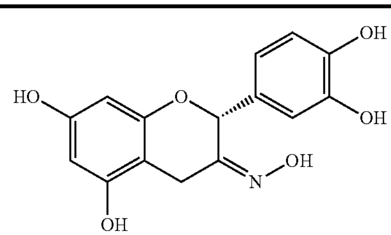 | (R,E)-2-(3,4-dihydroxyphenyl)-5,7-dihydroxychroman-3-one oxime | $C_{15}H_{13}NO_6$ | 303.07 |
| 1002 | 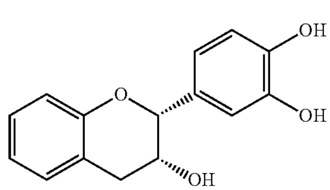 [SMILES: Oc1ccc([C@H]2Oc3ccccc3C[C@H]2O)cc1O] | Cis (±) 3-hydroxychroman-2-yl)benzene-1,2-diol | $C_{15}H_{14}O_4$ | 258.09 |

TABLE 1-continued

Illustrative Compounds of the present invention

| SPR No | Structure | Chemical name | Molecular Formula | Mol. Weight |
|---|---|---|---|---|
| 1003 | 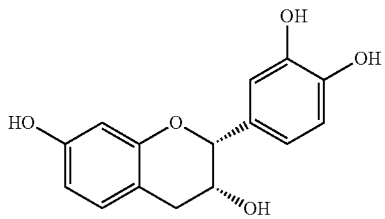 [SMILES: Oc1ccc2c(c1)O[C@H](c1ccc(O)c(O)c1)[C@H](O)C2] | Cis (±) 2-(3,4-dihydroxyphenyl)chroman-3,7-diol | $C_{15}H_{14}O_5$ | 274.08 |
| 1004 | 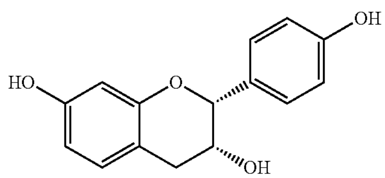 [SMILES: Oc1ccc([C@H]2Oc3cc(O)ccc3C[C@H]2O)cc1] | Cis (±) 2-(4-hydroxyphenyl)chroman-3,7-diol | $C_{15}H_{14}O_4$ | 258.09 |
| 1005 | 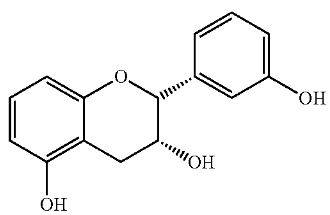 | Cis (±) 2-(3-hydroxyphenyl)chroman-3,5-diol | $C_{15}H_{14}O_4$ | 258.27 |
| 1006 | 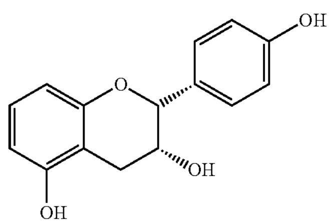 | Cis (±) 2-(4-hydroxyphenyl)chroman-3,5-diol | $C_{15}H_{14}O_4$ | 258.27 |
| 1007 | 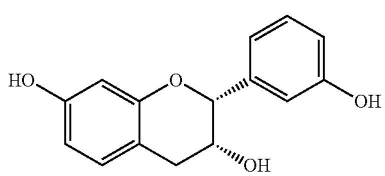 [SMILES: Oc1cccc([C@H]2Oc3cc(O)ccc3C[C@H]2O)c1] | Cis (±) 2-(3-hydroxyphenyl)chroman-3,7-diol | $C_{15}H_{14}O_4$ | 258.27 |
| 1008 | 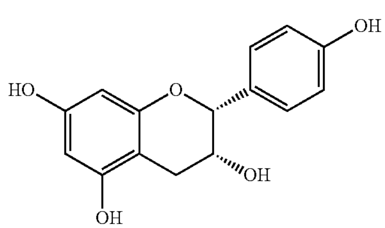 [SMILES: Oc1ccc([C@H]2Oc3cc(O)cc(O)c3C[C@H]2O)cc1] | Cis (±) 2-(4-hydroxyphenyl)chroman-3,5,7-triol | $C_{15}H_{14}O_5$ | 274.27 |
| 1009 | 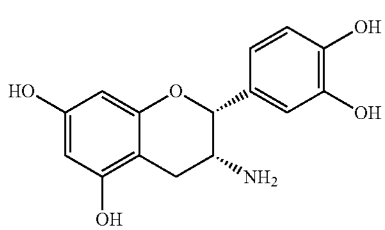 [SMILES: N[C@@H]1Cc2c(O)cc(O)cc2O[C@@H]1c1ccc(O)c(O)c1] | (2R,3S)-2-(3,4-dihydroxyphenyl)-3-methylchroman-3,5,7-triol | $C_{17}H_{18}NO_7$ | 348.11 |

TABLE 1-continued

Illustrative Compounds of the present invention

| SPR No | Structure | Chemical name | Molecular Formula | Mol. Weight |
|---|---|---|---|---|
| 1010 | 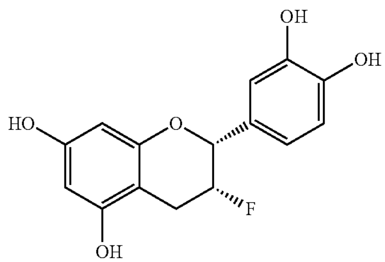 [SMILES: Oc1cc(O)c2c(c1)O[C@H](c1ccc(O)c(O)c1)[C@H](F)C2] | (2R,3R)-2-(2,3-dihydroxyphenyl)-3-fluorochroman-5,7-diol | $C_{15}H_{13}FO_5$ | 292.07 |
| 1011 | 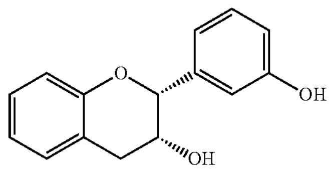 [SMILES: Oc1cccc([C@H]2Oc3ccccc3C[C@H]2O)c1] | Cis (±) 2-(3-hydroxyphenyl)chroman-3-ol | $C_{15}H_{14}O_3$ | 242.09 |
| 1012 | 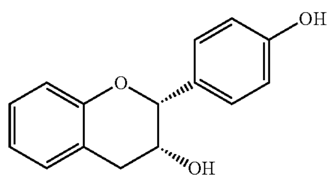 [SMILES: Oc1ccc([C@H]2Oc3ccccc3C[C@H]2O)cc1] | Cis (±) 2-(4-hydroxyphenyl)chroman-3-ol | $C_{15}H_{14}O_3$ | 242.09 |
| 1013 | 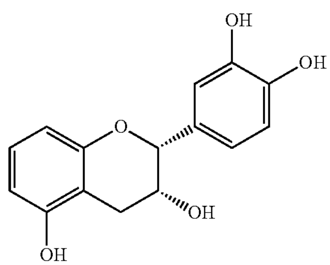 [SMILES: Oc1ccc([C@H]2Oc3cccc(O)c3C[C@H]2O)cc1O] | Cis (±) 2-(3,4-dihydroxyphenyl)chroman-3,5-diol | $C_{15}H_{14}O_5$ | 274.08 |
| 1014 | 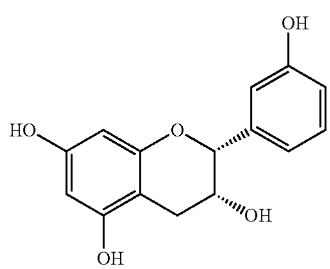 [SMILES: Oc1cccc([C@H]2Oc3cc(O)cc(O)c3C[C@H]2O)c1] | Cis (±) 2-(3-hydroxyphenyl)chroman-3,5,7-triol | $C_{15}H_{14}O_5$ | 274.08 |
| 1015 | 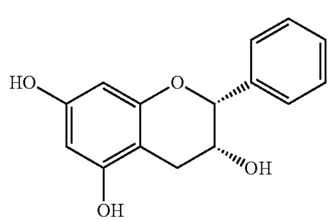 [SMILES: Oc1cc(O)c2c(c1)O[C@H](c1ccccc1)[C@H](O)C2] | Cis (±) 2-phenylchroman-3,5,7-triol | $C_{15}H_{14}O_4$ | 258.1 |

TABLE 1-continued

Illustrative Compounds of the present invention

| SPR No | Structure | Chemical name | Molecular Formula | Mol. Weight |
|---|---|---|---|---|
| 1016 | 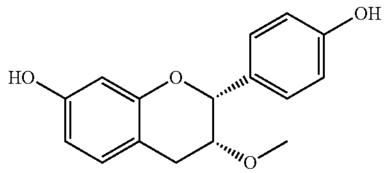 [SMILES: CO[C@@H]1Cc2ccc(O)cc2O[C@@H]1c1ccc(O)cc1] | Cis (±) 2-(4-hydroxyphenyl)-3-methoxychroman-7-ol | $C_{16}H_{16}O_4$ | 272.1 |
| 1017 | 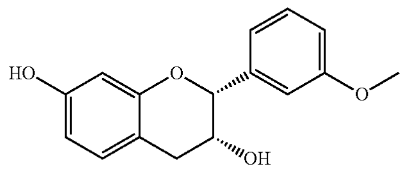 [SMILES: COc1cccc([C@H]2Oc3cc(O)ccc3C[C@H]2O)c1] | Cis (±) 2-(4-methoxyphenyl)chroman-3,7-diol | $C_{16}H_{16}O_4$ | 272.1 |
| 1018 | 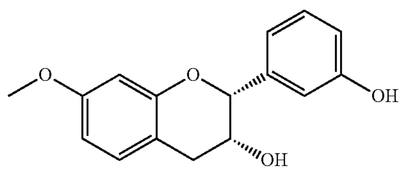 [SMILES: COc1ccc2c(c1)O[C@H](c1cccc(O)c1)[C@H](O)C2] | Cis (±) 2-(4-hydroxyphenyl)-7-methoxychroman-3-ol | $C_{16}H_{16}O_4$ | 272.1 |
| 1019 | 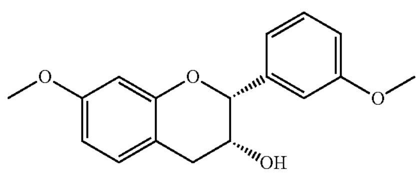 | Cis (±) 7-methoxy-2-(4-methoxyphenyl)chroman-3-ol | $C_{17}H_{18}O_4$ | 286.12 |
| 1020 | 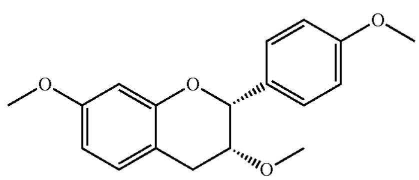 | Cis (±) 3,7-dimethoxy-2-(4-methoxyphenyl)chromic | $C_{18}H_{20}O_4$ | 300.14 |
| 1021 | 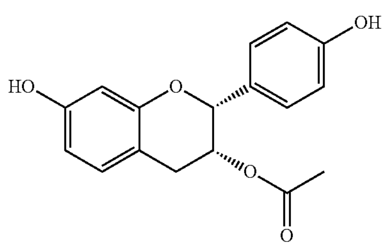 [SMILES: CC(=O)O[C@@H]1Cc2ccc(O)cc2O[C@@H]1c1ccc(O)cc1] | Cis (±) 7-hydroxy-2-(4-hydroxyphenyl)chroman-3-yl acetate | $C_{17}H_{16}O_5$ | 300.1 |
| 1022 | 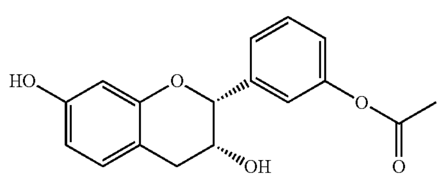 [SMILES: CC(=O)Oc1cccc([C@H]2Oc3cc(O)ccc3C[C@H]2O)c1] | Cis (±) 4-(3,7-dihydroxychroman-2-yl)phenyl acetate | $C_{17}H_{16}O_5$ | 300.1 |
| 1023 | 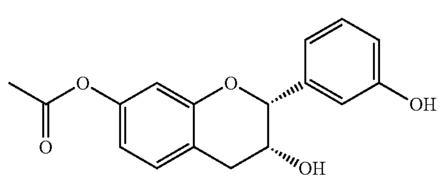 [SMILES: CC(=O)Oc1ccc2c(c1)O[C@H](c1cccc(O)c1)[C@H](O)C2] | Cis (±) 3-hydroxy-2-(4-hydroxyphenyl)chroman-7-yl acetate | $C_{17}H_{16}O_5$ | 300.1 |

TABLE 1-continued

Illustrative Compounds of the present invention

| SPR No | Structure | Chemical name | Molecular Formula | Mol. Weight |
|---|---|---|---|---|
| 1024 | 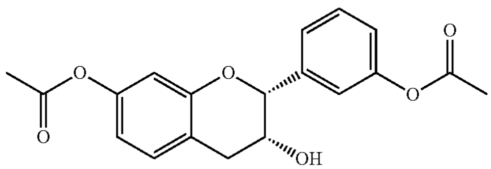 [SMILES: CC(=O)Oc1cccc([C@H]2Oc3cc(OC(C)=O)ccc3C[C@H]2O)c1] | Cis (±) 4-(7-acetoxy-3-hydroxychroman-2-yl)phenyl acetate | $C_{19}H_{18}O_6$ | 342.11 |
| 1025 | 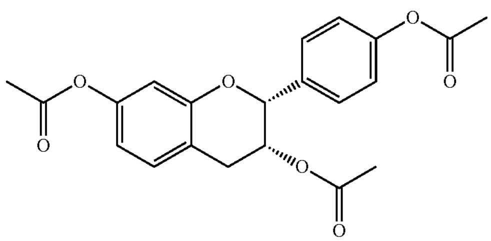 [SMILES: CC(=O)Oc1ccc([C@H]2Oc3cc(OC(C)=O)ccc3C[C@H]2OC(C)=O)cc1] | Cis (±) 2-(4-acetoxyphenyl)chroman-3,7-diyl diacetate | $C_{21}H_{20}O_7$ | 384.12 |
| 1026 | 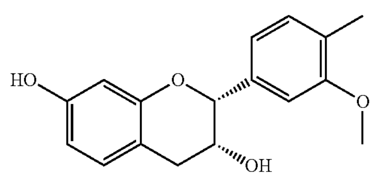 [SMILES: COc1cc([C@H]2Oc3cc(O)ccc3C[C@H]2O)ccc1C] | 2-(3-methoxy-4-methylphenyl)chromane-3,7-diol | $C_{17}H_{18}O_4$ | 286.12 |
| 1027 | 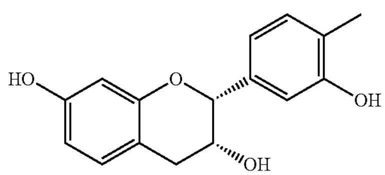 [SMILES: Cc1ccc([C@H]2Oc3cc(O)ccc3C[C@H]2O)cc1O] | 2-(3-hydroxy-4-methylphenyl)chromane-3,7-diol | $C_{16}H_{16}O_4$ | 272.10 |
| 1028 | 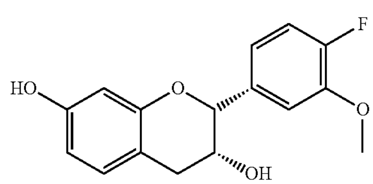 | 2-(4-fluoro-3-methoxyphenyl)chromane-3,7-diol | $C_{16}H_{15}FO_4$ | 290.10 |
| 1029 | 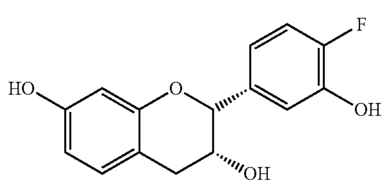 | 2-(4-fluoro-3-hydroxyphenyl)chromane-3,7-diol | $C_{15}H_{13}FO_4$ | 276.08 |
| 1030 | 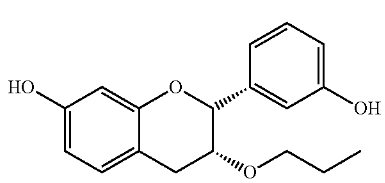 | 2-(3-hydroxyphenyl)-3-propoxychroman-7-ol | $C_{18}H_{20}O_4$ | 300.14 |

TABLE 1-continued

Illustrative Compounds of the present invention

| SPR No | Structure | Chemical name | Molecular Formula | Mol. Weight |
|---|---|---|---|---|
| 1031 | 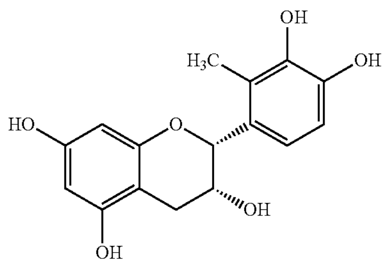 [SMILES: Cc1c([C@H]2Oc3cc(O)cc(O)c3C[C@H]2O)ccc(O)c1O] | Cis (±) 2-(3,4-dihydroxy-2-methylphenyl)chroman-3,5,7-triol | $C_{16}H_{16}O_6$ | 304.29 |
| 1032 | 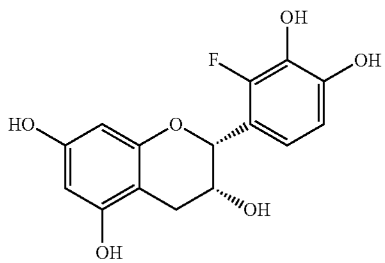 [SMILES: Oc1cc(O)c2c(c1)O[C@H](c1ccc(O)c(O)c1F)[C@H](O)C2] | Cis (±) 2-(2-fluoro-3,4-dihydroxyphenyl)chroman-3,5,7-triol | $C_{15}H_{13}FO_6$ | 308.07 |
| 1033 | 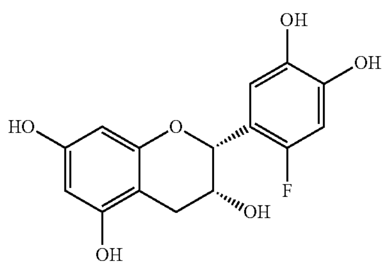 [SMILES: Oc1cc(O)c2c(c1)O[C@H](c1cc(O)c(O)cc1F)[C@H](O)C2] | Cis (±) 2-(2-fluoro-4,5-dihydroxyphenyl)chromane-3,5,7-triol | $C_{15}H_{13}FO_6$ | 308.07 |
| 1034 | 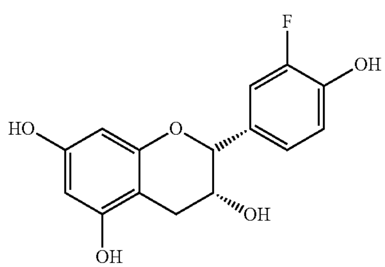 | Cis (±) 2-(3-fluoro-4-hydroxyphenyl)chromane-3,5,7-triol | $C_{15}H_{13}FO_5$ | 292.07 |
| 1035 | 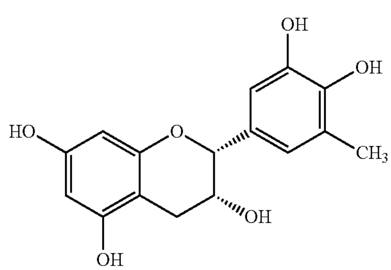 [SMILES: Cc1cc([C@H]2Oc3cc(O)cc(O)c3C[C@H]2O)cc(O)c1O] | Cis (±) (2-(3,4-dihydroxy-5-methylphenyl)chromane-3,5,7-triol | $C_{16}H_{16}O_6$ | 304.09 |

TABLE 1-continued

Illustrative Compounds of the present invention

| SPR No | Structure | Chemical name | Molecular Formula | Mol. Weight |
|---|---|---|---|---|
| 1036 | 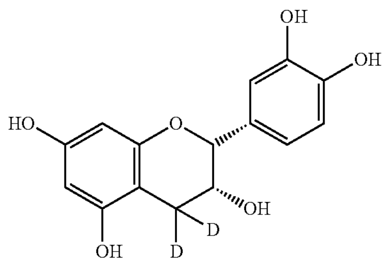 | (2R,3R)-2-(3,4-dihydroxyphenyl)chromane-4,4-d2-3,5,7-triol | $C_{15}H_{12}D_2O_6$ | 292.09 |
| 1037 | 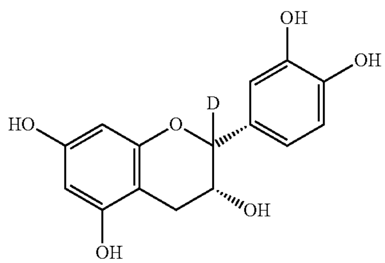 | (2R,3R)-2-(3,4-dihydroxyphenyl)chromane-2-d-3,5,7-triol | $C_{15}H_{13}DO_6$ | 291.09 |
| 1038 | 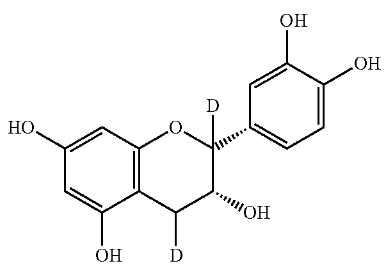 | (2R,3R)-2-(3,4-dihydroxyphenyl)chromane-2,4-d2-3,5,7-triol | $C_{15}H_{12}D_2O_6$ | 292.09 |
| 1039 | 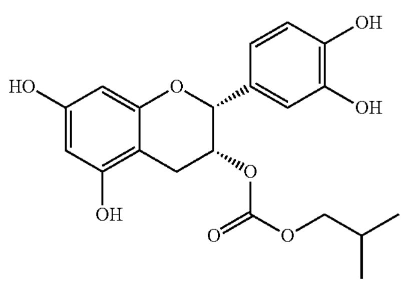 [SMILES: CC(C)COC(=O)O[C@@H]1Cc2c(O)cc(O)cc2O[C@@H]1c1ccc(O)c(O)c1] | (2R,3R)-2-(3,4-dihydroxyphenyl)-5,7-dihydroxychroman-3-yl isobutyl carbonate | $C_{20}H_{22}O_8$ | 390.13 |
| 1040 | 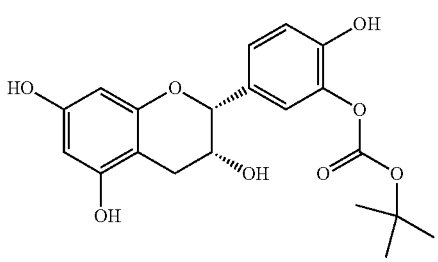 [SMILES: CC(C)(C)OC(=O)Oc1cc([C@H]2Oc3cc(O)cc(O)c3C[C@H]2O)ccc1O] | tert-butyl (2-hydroxy-5-(2R,3R)-3,5,7-trihydroxychroman-2yl)phenyl)carbonate | | |

TABLE 1-continued

Illustrative Compounds of the present invention

| SPR No | Structure | Chemical name | Molecular Formula | Mol. Weight |
|---|---|---|---|---|
| 1041 | 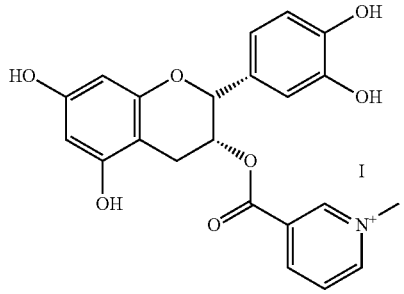 | 3-((((2R,3R)-2-(3,4-dihydroxyphenyl)-5,7-dihydroxychroman-3-yl)oxy)carbonyl)-1-methylpyridin-1-ium | $C_{22}H_{20}INO_7^+$ | 537.03 |
| 1042 | 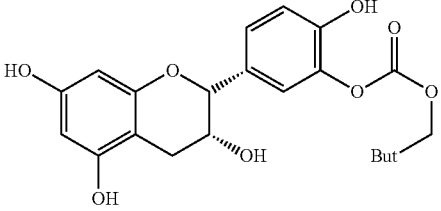 | 2-hydroxy-5-((2R,3R)-3,5,7-trihydroxychroman-2-yl)phenyl neopentyl carbonate | $C_{21}H_{24}O_8$ | 404.15 |
| 1043 | 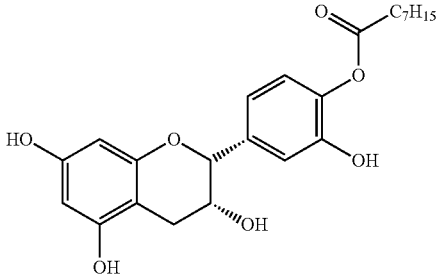 | 2-hydroxy-4-((2R,3R)-3,5,7-trihydroxychroman-2-yl)phenyl octanoate | $C_{23}H_{28}O_7$ | 416.18 |
| 1044 | 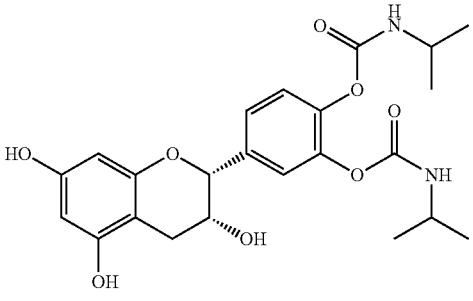 [SMILES: CC(C)NC(=O)Oc1ccc([C@H]2Oc3cc(O)cc(O)c3C[C@H]2O)cc1OC(=O)NC(C)C] | 4-((2R,3R)-3,5,7-trihydroxychroman-2-yl)-1,2-phenylene bis(isopropylcarbamate) | $C_{23}H_{28}N_2O_8$ | 460.18 |
| 1045 | 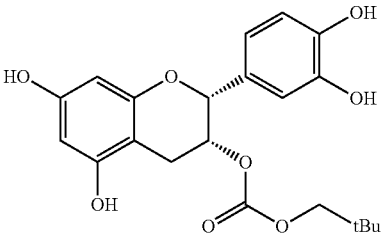 [SMILES: CC(C)(C)COC(=O)O[C@@H]1Cc2c(O)cc(O)cc2O[C@@H]1c1ccc(O)c(O)c1] | (2R,3R)-2-(3,4-dihydroxyphenyl)-5,7-dihydroxychroman-3-yl neopentyl carbonate | $C_{21}H_{24}O_8$ | 404.15 |

TABLE 1-continued

Illustrative Compounds of the present invention

| SPR No | Structure | Chemical name | Molecular Formula | Mol. Weight |
|---|---|---|---|---|
| 1046 | 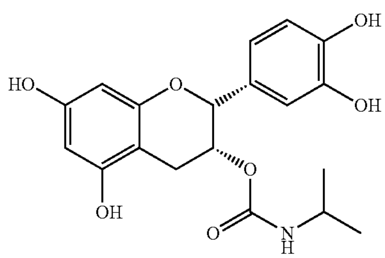 | (2R,3R)-2-(3,4-dihydroxyphenyl)-5,7-dihydroxychroman-3-yl isopropylcarbamate | $C_{19}H_{21}NO_7$ | 375.13 |
| 1047 | 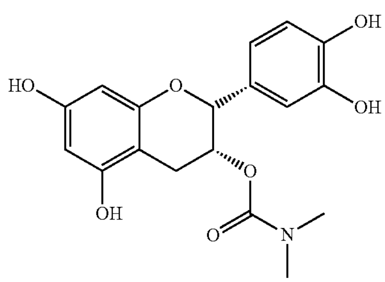 | (2R,3R)-2-(3,4-dihydroxyphenyl)-5,7-dihydroxychroman-3-yl dimethylcarbamate | $C_{18}H_{19}NO_7$ | 361.12 |
| 1048 | 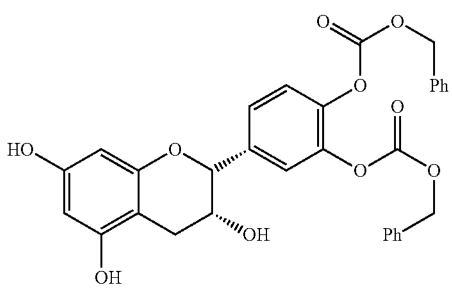 | dibenzyl (4-((2R,3R)-3,5,7-trihydroxychroman-2-yl)-1,2-phenylene) bis(carbonate) | $C_{31}H_{26}O_{10}$ | 558.15 |
| 1049 | 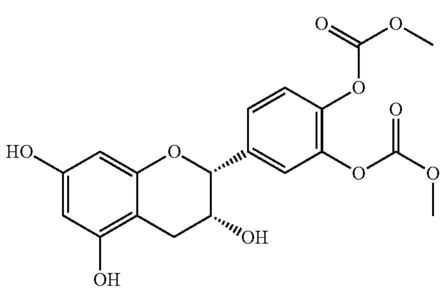 [SMILES: COC(=O)Oc1ccc([C@H]2Oc3cc(O)cc(O)c3C[C@H]2O)cc1OC(=O)OC] | dimethyl (4-((2R,3R)-3,5,7-trihydroxychroman-2-yl)-1,2-phenylene) bis(carbonate) | $C_{19}H_{18}O_{10}$ | 406.09 |
| 1050 | 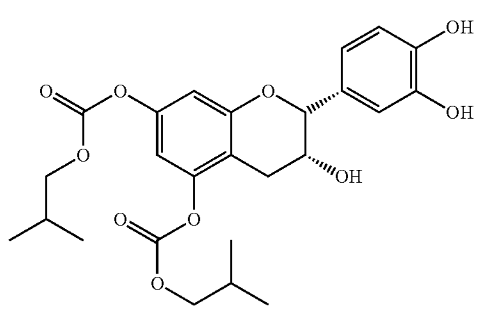 | (2R,3R)-2-(3,4-dihydroxyphenyl)-3-hydroxychromane-5,7-diyl diisobutyl bis(carbonate) | $C_{25}H_{30}O_{10}$ | 490.18 |

TABLE 1-continued

Illustrative Compounds of the present invention

| SPR No | Structure | Chemical name | Molecular Formula | Mol. Weight |
|---|---|---|---|---|
| 1051 | 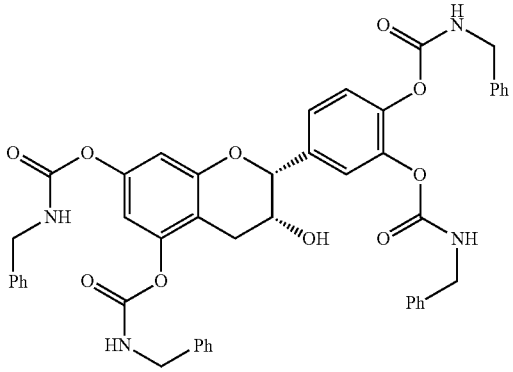 [SMILES: O=C(NCc1ccccc1)Oc1cc(OC(=O)NCc2ccccc2)c2c(c1)O[C@H](c1ccc(OC(=O)NCc3ccccc3)c(OC(=O)NCc3ccccc3)c1)[C@H](O)C2] | 4-((2R,3R)-5,7-bis((benzylcarbamoyl)oxy)-3-hydroxychroman-2-yl)-1,2-phenylene bis(benzylcarbamate) | $C_{47}H_{42}N_4O_{10}$ | 822.29 |
| 1052 | 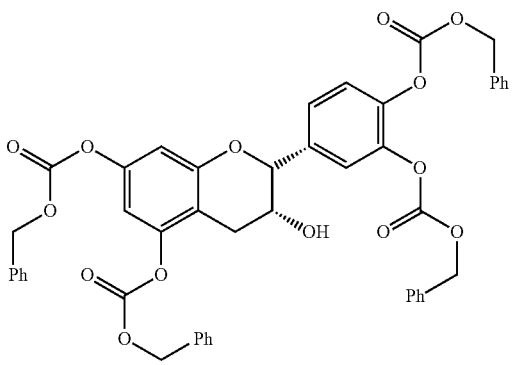 | dibenzyl (4-((2R,3R)-5,7-bis(((benzyloxy)carbonyl)oxy)-3-hydroxychroman-2-yl)-1,2-phenylene) bis(carbonate) | $C_{47}H_{38}O_{14}$ | 826.23 |
| 1053 | 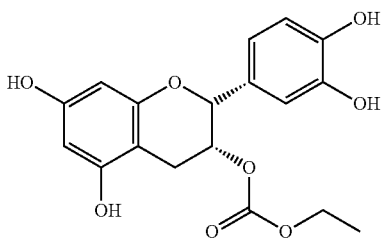 | (2R,3R)-2-(3,4-dihydroxyphenyl)-5,7-dihydroxychroman-3-yl ethyl carbonate | C18H18O8 | 362.10 |
| 1054 | 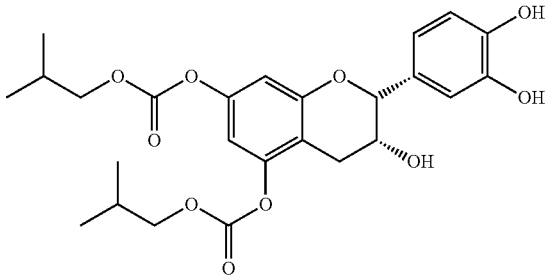 | (2R,3R)-2-(3,4-dihydroxyphenyl)-3-hydroxychromane-5,7-diyl diisobutyl bis(carbonate) | C25H30O10 | 490.18 |
| 1055 | 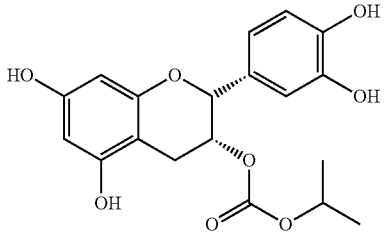 | (2R,3R)-2-(3,4-dihydroxyphenyl)-5,7-dihydroxychroman-3-yl isopropyl carbonate | C19H20O8 | 376.12 |

TABLE 1-continued

Illustrative Compounds of the present invention

| SPR No | Structure | Chemical name | Molecular Formula | Mol. Weight |
|---|---|---|---|---|
| 1056 | 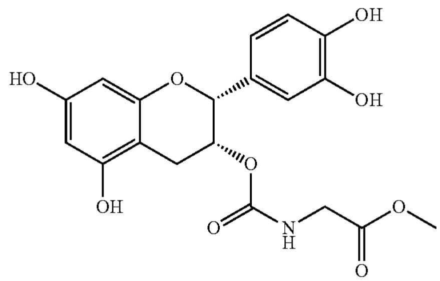 [SMILES: COC(=O)CNC(=O)O[C@@H]1Cc2c(O)cc(O)cc2O[C@@H]1c1ccc(O)c(O)c1] | methyl ((((2R,3R)-2-(3,4-dihydroxyphenyl)-5,7-dihydroxychroman-3-yl)oxy)carbonyl)glycinate | C19H19NO9 | 405.11 |
| 1057 | 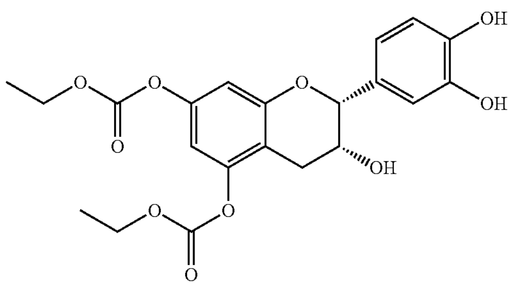 [SMILES: CCOC(=O)Oc1cc(OC(=O)OCC)c2c(c1)O[C@H](c1ccc(O)c(O)c1)[C@H](O)C2] | (2R,3R)-2-(3,4-dihydroxyphenyl)-3-hydroxychromane-5,7-diyl diethyl bis(carbonate) | C21H22O10 | 434.12 |
| 1058 | 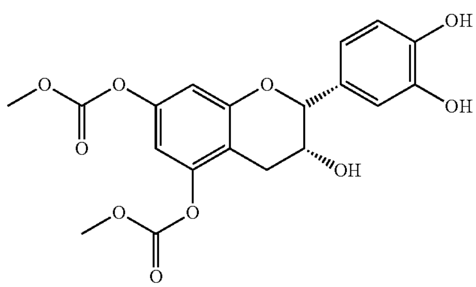 | (2R,3R)-2-(3,4-dihydroxyphenyl)-3-hydroxychromane-5,7-diyl dimethyl bis(carbonate) | C19H18O10 | 406.09 |
| 1059 | 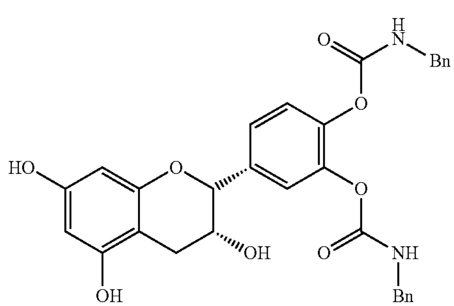 | 4-((2R,3R)-3,5,7-trihydroxychroman-2-yl)-1,2-phenylene bis(benzylcarbamate) | C31H28N2O8 | 556.18 |

TABLE 1-continued

Illustrative Compounds of the present invention

| SPR No | Structure | Chemical name | Molecular Formula | Mol. Weight |
|---|---|---|---|---|
| 1060 | 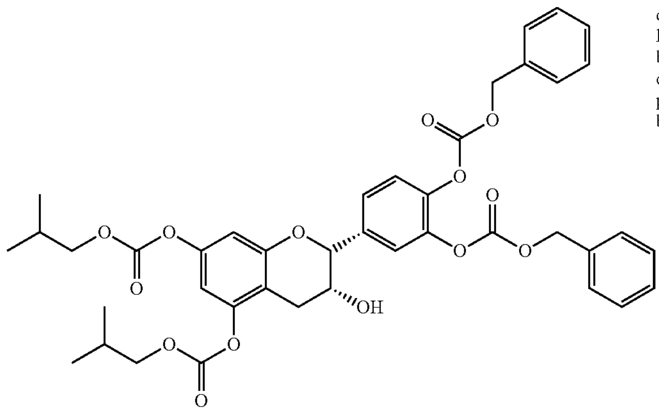 | dibenzyl (4-((2R,3R)-3-hydroxy-5,7-bis((isobutoxycarbonyl)oxy)chroman-2-yl)-1,2-phenylene) bis(carbonate) | C41H42O14 | 758.26 |
| 1061 | 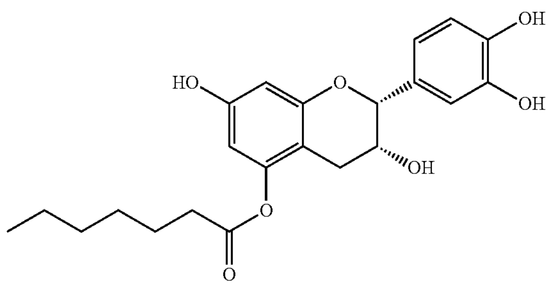 [SMILES: CCCCCCC(=O)Oc1cc(O)cc2c1C[C@@H](O)[C@@H](c1ccc(O)c(O)c1)O2] | (2R,3R)-2-(3,4-dihydroxyphenyl)-3,7-dihydroxychroman-5-yl heptanoate | C22H26O7 | 402.17 |
| 1062 | 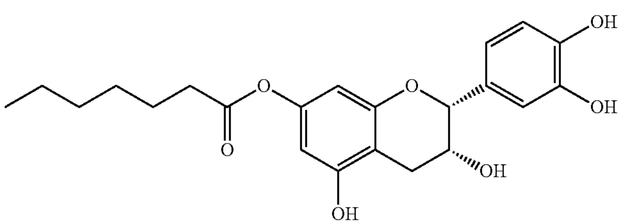 [SMILES: CCCCCCC(=O)Oc1cc(O)c2c(c1)O[C@H](c1ccc(O)c(O)c1)[C@H](O)C2] | (2R,3R)-2-(3,4-dihydroxyphenyl)-3,5-dihydroxychroman-7-yl heptanoate | C22H26O7 | 402.17 |
| 1063 | 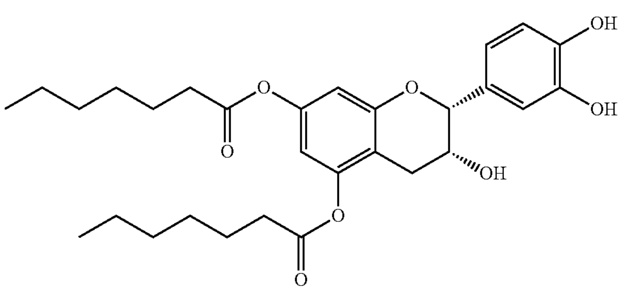 [SMILES: CCCCCCC(=O)Oc1cc(OC(=O)CCCCCC)c2c(c1)O[C@H](c1ccc(O)c(O)c1)[C@H](O)C2] | (2R,3R)-2-(3,4-dihydroxyphenyl)-3-hydroxychromane-5,7-diyl diheptanoate | C29H38O8 | 514.26 |
| 1064 | 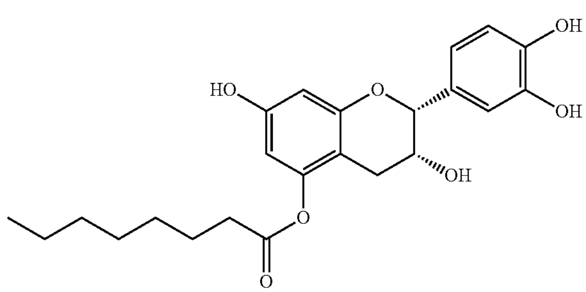 [SMILES: CCCCCCCC(=O)Oc1cc(O)cc2c1C[C@@H](O)[C@@H](c1ccc(O)c(O)c1)O2] | (2R,3R)-2-(3,4-dihydroxyphenyl)-3,7-dihydroxychroman-5-yl octanoate | C23H28O7 | 416.18 |

TABLE 1-continued

Illustrative Compounds of the present invention

| SPR No | Structure | Chemical name | Molecular Formula | Mol. Weight |
|---|---|---|---|---|
| 1065 | 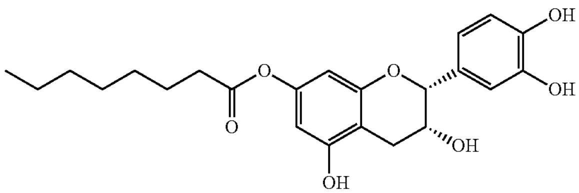 [SMILES: CCCCCCCC(=O)Oc1cc(O)c2c(c1)O[C@H](c1ccc(O)c(O)c1)[C@H](O)C2] | (2R,3R)-2-(3,4-dihydroxyphenyl)-3,5-dihydroxychroman-7-yl octanoate | C23H28O7 | 416.18 |
| 1066 | 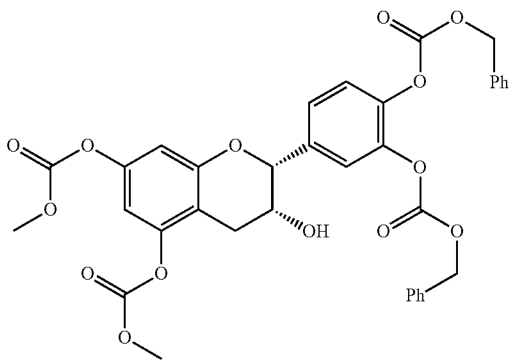 [SMILES: COC(=O)Oc1cc(OC(=O)OC)c2c(c1)O[C@H](c1ccc(OC(=O)OCc3ccccc3)c(OC(=O)OCc3ccccc3)c1)[C@H](O)C2] | dibenzyl (4-((2R,3R)-3-hydroxy-5,7-bis((methoxycarbonyl)oxy)chroman-2-yl)-1,2-phenylene) bis(carbonate) | C35H30O14 | 674.16 |
| 1067 | 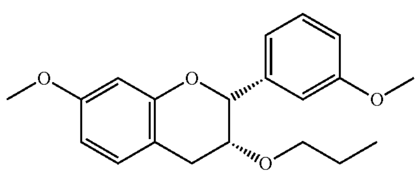 | (2R,3R)-7-methoxy-2-(3-methoxyphenyl)-3-propoxychromane | C20H24O4 | 328.17 |
| 1068 | 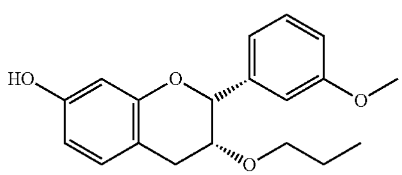 | (2R,3R)-2-(3-methoxyphenyl)-3-propoxychroman-7-ol | C19H22O4 | 314.15 |
| 1069 | 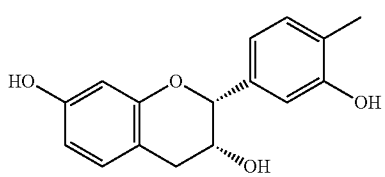 [SMILES: Cc1ccc([C@H]2Oc3cc(O)ccc3C[C@H]2O)cc1O] | (2R,3R)-2-(3-hydroxy-4-methylphenyl)chromane-3,7-diol | C16H16O4 | 272.10 |
| 1070 | 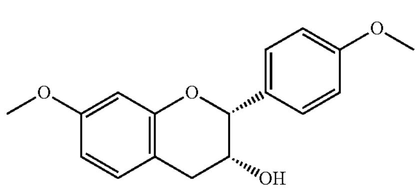 | (2R,3R)-7-methoxy-2-(4-methoxyphenyl)chroman-3-ol | C17H18O4 | 286.12 |

TABLE 1-continued

Illustrative Compounds of the present invention

| SPR No | Structure | Chemical name | Molecular Formula | Mol. Weight |
|---|---|---|---|---|
| 1071 | 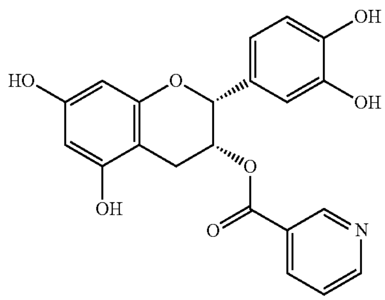 [SMILES: O=C(O[C@@H]1Cc2c(O)cc(O)cc2O[C@@H]1c1ccc(O)c(O)c1)c1cccnc1] | (2R,3R)-2-(3,4-dihydroxyphenyl)-5,7-dihydroxychroman-3-yl nicotinate | C21H17NO7 | 395.10 |
| 1072 | 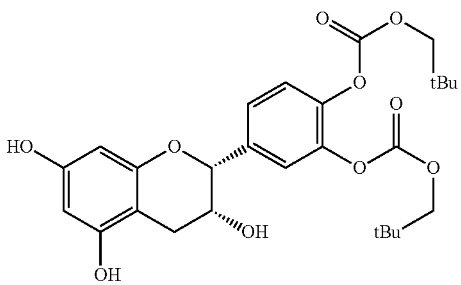 [SMILES: CC(C)(C)COC(=O)Oc1ccc([C@H]2Oc3cc(O)cc(O)c3C[C@H]2O)cc1OC(=O)OCC(C)(C)C] | dineopentyl (4-((2R,3R)-3,5,7-trihydroxychroman-2-yl)-1,2-phenylene) bis(carbonate) | C27H34O10 | 518.22 |
| 1073 | 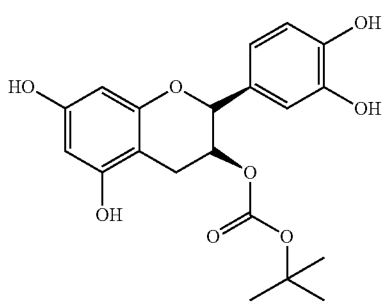 | tert-butyl ((2R,3R)-2-(3,4-dihydroxyphenyl)-5,7-dihydroxychroman-3-yl) carbonate | C20H22O8 | 390.13 |
| 1074 | 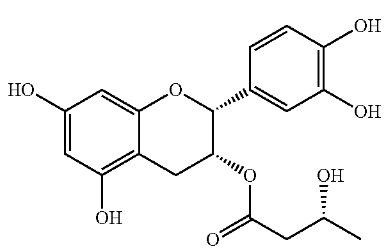 [SMILES: C[C@@H](O)CC(=O)O[C@@H]1Cc2c(O)cc(O)cc2O[C@@H]1c1ccc(O)c(O)c1] | (2R,3R)-2-(3,4-dihydroxyphenyl)-5,7-dihydroxychroman-3-yl (R)-3-hydroxybutanoate | C19H20O8 | 376.12 |
| 1075 | 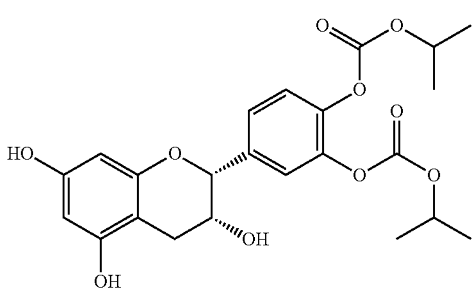 [SMILES: CC(C)OC(=O)Oc1ccc([C@H]2Oc3cc(O)cc(O)c3C[C@H]2O)cc1OC(=O)OC(C)C] | diisopropyl (4-((2R,3R)-3,5,7-trihydroxychroman-2-yl)-1,2-phenylene) bis(carbonate) | C23H26O10 | 462.15 |

TABLE 1-continued

Illustrative Compounds of the present invention

| SPR No | Structure | Chemical name | Molecular Formula | Mol. Weight |
|---|---|---|---|---|
| 1076 | 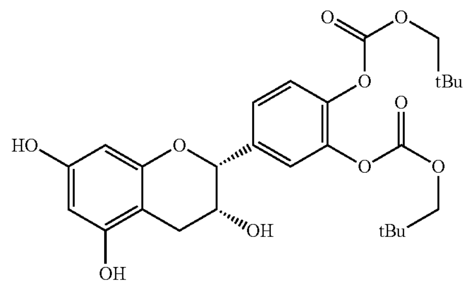 [SMILES: CC(C)(C)COC(=O)Oc1ccc([C@H]2Oc3cc(O)cc(O)c3C[C@H]2O)cc1OC(=O)OCC(C)(C)C] | dineopentyl (4-((2R,3R)-3,5,7-trihydroxychroman-2-yl)-1,2-phenylene) bis(carbonate) | C27H34O10 | 518.22 |

The compounds of the present invention include:
I. (R,E)-2-(3,4-dihydroxyphenyl)-5,7-dihydroxychroman-3-one oxime
II. Cis (±) 3-hydroxychroman-2-yl)benzene-1,2-diol;
III. Cis (±) 2-(3,4-dihydroxyphenyl)chroman-3,7-diol;
IV. Cis (±) 2-(4-hydroxyphenyl)chroman-3,7-diol;
V. Cis (±) 2-(3-hydroxyphenyl)chroman-3,5-diol;
VI. Cis (±) 2-(4-hydroxyphenyl)chroman-3,5-diol;
VII. Cis (±) 2-(3-hydroxyphenyl)chroman-3,7-diol;
VIII. Cis (±) 2-(4-hydroxyphenyl)chroman-3,5,7-diol;
IX. (2R,3S)-2-(3,4-dihydroxyphenyl)-3-aminochroman-5,7-diol;
X. (2R,3S)-2-(3,4-dihydroxyphenyl)-3-fluorochroman-5,7-diol;
XI. Cis (±) 2-(3-hydroxyphenyl)chroman-3-ol;
XII. Cis (±) 2-(4-hydroxyphenyl)chroman-3-ol;
XIII. Cis (±) 2-(3,4-dihydroxyphenyl)chroman-3,5-diol;
XIV. Cis (±) 2-(3-hydroxyphenyl)chroman-3,5,7-triol;
XV. Cis (±) 2-phenylchroman-3,5,7-triol;
XVI. Cis (±) 2-(4-hydroxyphenyl)-3-methoxychroman-7-ol;
XVII. Cis (±) 2-(3-methoxyphenyl)chroman-3,7-diol;
XVIII. Cis (±) 2-(3-hydroxyphenyl)-7-methoxychroman-3-ol;
XIX. Cis (±) 7-methoxy-2-(3-methoxyphenyl)chroman-3-ol;
XX. Cis (±) 3,7-dimethoxy-2-(4-methoxyphenyl)chromic;
XXI. Cis (±) 7-hydroxy-2-(4-hydroxyphenyl)chroman-3-yl acetate;
XXII. Cis (±) 4-(3,7-dihydroxychroman-2-yl)phenyl acetate;
XXIII. Cis (±) 3-hydroxy-2-(3-hydroxyphenyl)chroman-7-yl acetate;
XXIV. Cis (±) 4-(7-acetoxy-3-hydroxychroman-2-yl)phenyl acetate;
XXV. Cis (±) 2-(4-acetoxyphenyl)chroman-3,7-diyl diacetate;
XXVI. 2-(3-methoxy-4-methylphenyl)chromane-3,7-diol;
XXVII. 2-(3-hydroxy-4-methylphenyl)chromane-3,7-diol;
XXVIII. 2-(4-fluoro-3-methoxyphenyl)chromane-3,7-diol;
XXIX. 2-(4-fluoro-3-hydroxyphenyl)chromane-3,7-diol;
XXX. 2-(3-hydroxyphenyl)-3-propoxychroman-7-ol;
XXXI. Cis (±) 2-(3,4-dihydroxy-2-methylphenyl)chroman-3,5,7-triol;
XXXII. Cis (±) 2-(2-fluoro-3,4-dihydroxyphenyl)chroman-3,5,7-triol;
XXXIII. Cis (±) 2-(2-fluoro-4,5-dihydroxyphenyl)chroman-3,5,7-triol;
XXXIV. Cis (±) 2-(3-fluoro-4-hydroxyphenyl)chromane-3,5,7-triol;
XXXV. Cis (±) 2-(3,4-dihydroxy-5-methylphenyl)chromane-3,5,7-triol;
XXXVI. (2R,3R)-2-(3,4-dihydroxyphenyl)chromane-4,4-d2-3,5,7-triol;
XXXVII. (2R,3R)-2-(3,4-dihydroxyphenyl)chromane-2-d-3,5,7-triol;
XXXVIII. (2R,3R)-2-(3,4-dihydroxyphenyl)chromane-2,4-d2-3,5,7-triol;
XXXIX. (2R,3R)-2-(3,4-dihydroxyphenyl)-5,7-dihydroxychromane-3-yl isobutyl carbonate;
XL. tert-butyl neopentyl (4-((2R,3R)-3,5,7-trihydroxychroman-2-yl)-1,2-phenylene) bis(carbonate);
XLI. 3-((((2R,3R)-2-(3,4-dihydroxyphenyl)-5,7-dihydroxychroman-3-yl)oxy)carbonyl)-1-methylpyridin-1-ium;
XLII. 2-hydroxy-5-((2R,3R)-3,5,7-trihydroxychroman-2-yl)phenyl neopentyl carbonate;
XLIII. 2-hydroxy-4-((2R,3R)-3,5,7-trihydroxychroman-2-yl)phenyl octanoate;
XLIV. 4-((2R,3R)-3,5,7-trihydroxychroman-2-yl)-1,2-phenylene bis(isopropyl carbamate);
XLV. (2R,3R)-2-(3,4-dihydroxyphenyl)-5,7-dihydroxychroman-3-yl neopentyl carbonate;
XLVI. (2R,3R)-2-(3,4-dihydroxyphenyl)-5,7-dihydroxychroman-3-yl-isopropyl carbamate;
XLVII. (2R,3R)-2-(3,4-dihydroxyphenyl)-5,7-dihydroxychroman-3-yl dimethyl carbamate;
XLVIII. dibenzyl (4-((2R,3R)-3,5,7-trihydroxychroman-2-yl)-1,2-phenylene) bis(carbonate);
XLIX. dimethyl (4-((2R,3R)-3,5,7-trihydroxychroman-2-yl)-1,2-phenylene) bis(carbonate);
L. (2R,3R)-2-(3,4-dihydroxyphenyl)-3-hydroxychromane-5,7-yl diisobutyl bis(carbonate);
LI. 4-((2R,3R)-5,7-bis((benzylcarbamoyl)oxy)-3-hydroxychromane-2-yl)-1,2-phenylene bis(benzylcarbamate);
LII. dibenzyl (4-((2R,3R)-5,7-bis(((benzyloxy)carbonyl)oxy)-3-hydroxychroman-2-yl)-1,2-phenylene bis(carbonate);
LIII. (2R,3R)-2-(3,4-dihydroxyphenyl)-5,7-dihydroxychroman-3-yl ethyl carbonate);
LIV. (2R,3R)-2-(3,4-dihydroxyphenyl)-3-dihydroxychromane-5,7-diyl diisobutyl bis(carbonate);
LV. (2R,3R)-2-(3,4-dihydroxyphenyl)-5,7-dihydroxychroman-3-yl isopropyl carbonate);
LVI. methyl ((((2R,3R)-2-(3,4-dihydroxyphenyl)-5,7-dihydroxychroman-3-yl)oxy)carbonyl)glycinate;

LVII. (2R,3R)-2-(3,4-dihydroxyphenyl)-3-hydroxychromane-5,7-diyl diethyl bis(carbonate);
LVIII. (2R,3R)-2-(3,4-dihydroxyphenyl)-3-hydroxychromane-5,7-diyl dimethyl bis(carbonate);
LIX. 4-((2R,3R)-3,5,7-trihydroxychromane-2-yl)-1,2-phenylene bis(benzyl carbamate);
LX. dibenzyl (4-((2R,3R)-3-hydroxy-5,7-bis((isobutoxycarbonyl)oxy)chroman-2-yl)-1,2-phenylene bis(carbonate);
LXI. (2R,3R)-2-(3,4-dihydroxyphenyl)-3,7-dihydroxychroman-5-yl heptanoate;
LXII. (2R,3R)-2-(3,4-dihydroxyphenyl)-3,5-dihydroxychromane-7-yl heptanoate;
LXIII. (2R,3R)-2-(3,4-dihydroxyphenyl)-3-hydroxychromane-5,7-yl diheptanoate;
LXIV. (2R,3R)-2-(3,4-dihydroxyphenyl)-3,7-dihydroxychromane-5-yl octanoate;
LXV. (2R,3R)-2-(3,4-dihydroxyphenyl)-3,5-dihydroxychromane-7-yl octanoate;
LXVI. dibenzyl (4-((2R,3R)-3-hydroxy-5,7-bis((methoxycarbonyl)oxy)chroman-2-yl)-1,2-phenylene bis(carbonate);
LXVII. (2R,3R)-7-methoxy-2-(3-methoxyphenyl)-3-propoxychromane;
LXVIII. (2R,3R)-2-(3-methoxyphenyl)-3-propoxychroman-7-ol;
LXIX. (2R,3R)-2-(3-hydroxy-4-methylphenyl)chromane-3,7-diol;
LXX. (2R,3R)-7-methoxy-2-(4-methoxyphenyl)chroman-3-ol;
LXXI. (2R,3R)-2-(3,4-dihydroxyphenyl)-5,7-dihydroxychroman-3-yl nicotinate;
LXXII. dineopentyl (4-((2R,3R)-3,5,7-trihydroxychroman-2-yl)-1,2-phenylene) bis(carbonate);
LXXIII. tert-butyl ((2R,3R)-2-(3,4-dihydroxyphenyl)-5,7-dihydroxychroman-3-yl) carbonate;
LXXIV. (2R,3R)-2-(3,4-dihydroxyphenyl)-5,7-dihydroxychroman-3-yl (R)-3-hydroxybutanoate
LXXV. diisopropyl (4-((2R,3R)-3,5,7-trihydroxychroman-2-yl)-1,2-phenylene) bis(carbonate);
LXXVI. dineopentyl (4-((2R,3R)-3,5,7-trihydroxychroman-2-yl)-1,2-phenylene) bis(carbonate).

In another embodiment, the present invention also discloses a process of preparing the compounds of formula (I) and formula (II) as below, Synthetic Scheme 1:

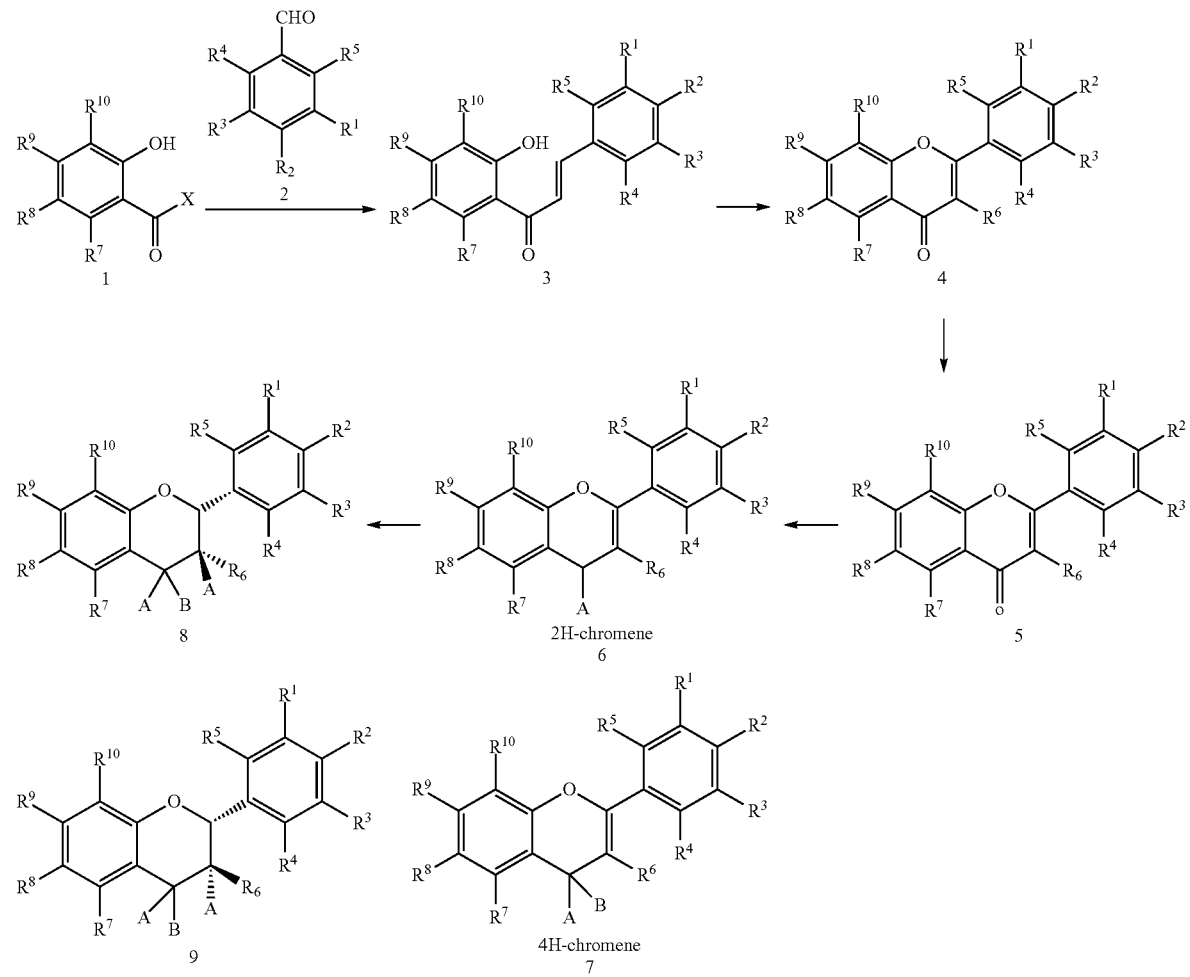

$R^1, R^2, R^7, R^8$ = H or OH or OBn
$R_9$ = Me, F
$R_6$ = OBn
A, B = H or D

Scheme 1 comprises the following steps:
Step 1:
Hydroxyl groups of an acetophenone of Formula 1 is optionally protected with a protecting agent in presence of a base and a solvent;

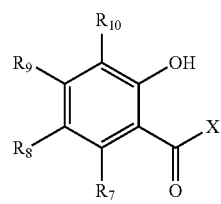

1

The protecting agent is preferably a benzylating agent such as benzyl bromide in presence of suitable base such as Scheme 2 comprises the following steps:

Synthetic Scheme 2:

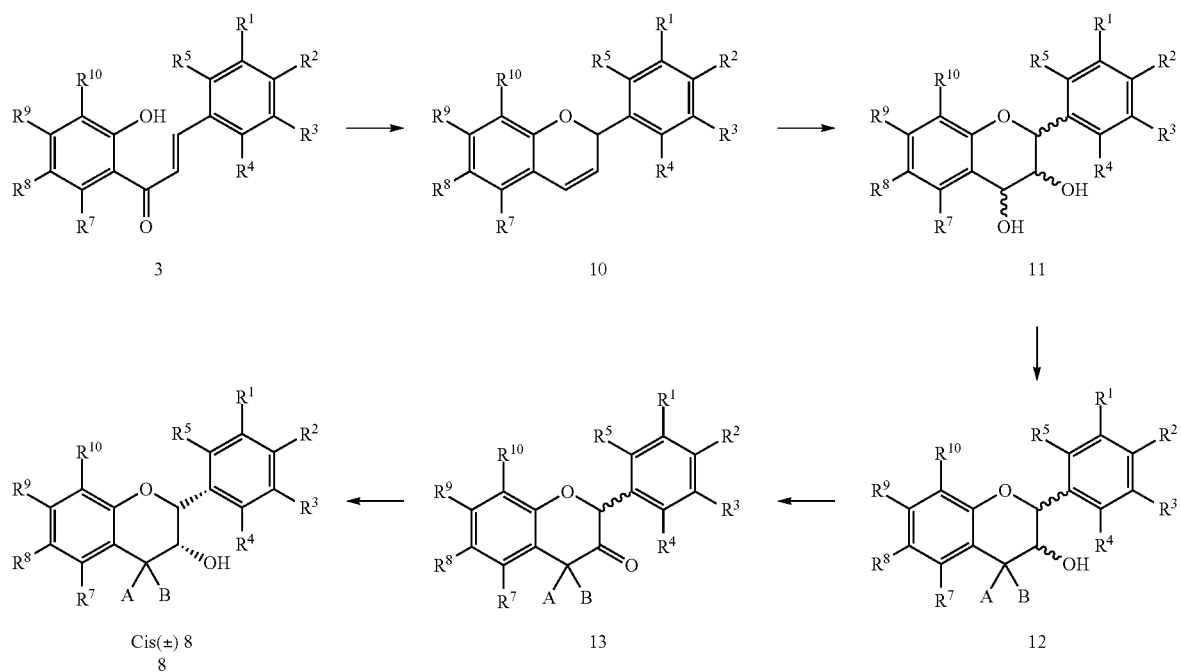

potassium carbonate in presence of suitable solvent such as dimethylformamide or acetone at ambient temperature may be converted to a compound having protected hydroxyl group. The protected compound is further converted to chalcone of formula [3] in presence of suitable base such as NaOH, KOH, or piperidine in presence of suitable solvents as such MeOH, EtOH, THF at an ambient temperature;
Step 2:
Chalcone of formula [3] may be converted into compound [4] in presence of suitable base such as NaOH, in presence of suitable epoxidizing agent such as hydrogen peroxide and in presence of suitable solvent such as MEOH or EtOH.
Step 3:
Compound of formula [4] may be treated with a protecting agent to protect the hydroxyl group(s) if any, preferably with a benzylating agent such as benzyl bromide in presence of suitable base such as potassium carbonate in presence of suitable solvent such as dimethylformamide or acetone at ambient temperature may be converted to a compound [5] having protected hydroxyl group;
Step 4:
Compound [5] may be converted to mixture of compound [6] and [7] in presence of chiral/achiral reducing agents such as lithium aluminum hydride/deutride in solvents such as THF or ether at a temperature ranging from ambient to reflux.
Step 5:
Compounds [6] and [7] may be converted to compound [8] and [9] on deprotection. 4H-chromene and 2H-chromene compounds obtained in step 4 when subjected to hydrogenation in presence of palladium on carbon in presence of hydrogen atmosphere or palladium hydroxide at a temperature ranging front ambient to 60° C. is converted to polyphenol analogues of the present invention.

Step 1:
Chalcone 3 which may be synthesized as described in synthetic scheme 1, on treatment with a reducing reagent such as $NaBH_4$ may be converted to 10 in presence of a suitable solvent such as EtOH or MeOH at temperature ranging from ambient to reflux.
Step 2:
Compound 10 may be converted to compound of general formula 11 in presence of suitable reagents such as $OsO_4$, with or without chiral co-catalysts such as AD-mix-α or AD-mix-β in presence of suitable solvent such as THF at a temperature ranging from ambient to reflux.
Step 3:
Compound 11 may be converted to 12 when treated with suitable reducing agents such as $NaCNBH_3$ in presence of suitable solvents as AcOH or THF at ambient temperature.

Step 4:

Compound 12 may be converted to compound 13 in presence of suitable oxidizing agents such as dess-martin periodinane in presence of suitable solvents such as THF or DCM.

Step 5:

Compound [13] may be converted to compound 8 in presence of suitable reducing agents such as l-selectride at a temperature ranging from −78° C. to room temperature in presence of suitable solvents such as THF.

Synthetic Scheme 3:

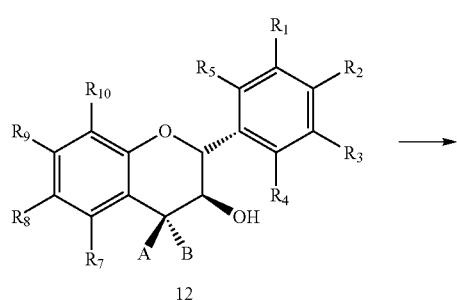

12

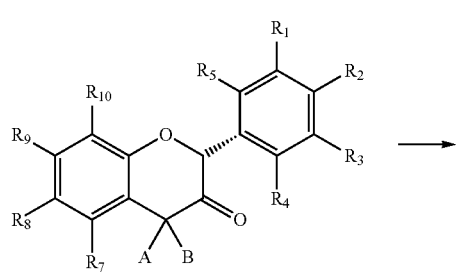

13

Synthetic Scheme 4:

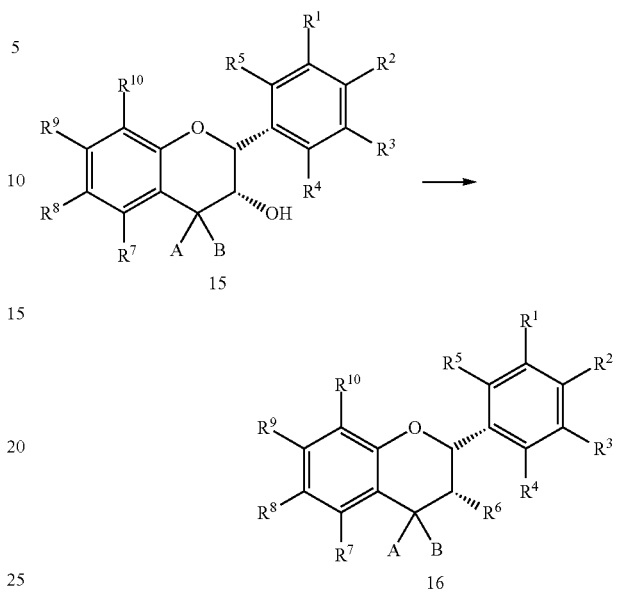

Any flavan-3-ol (15) such as epicatechin with or without a suitable protecting groups such as benzyl on phenolic OH can be functionalized into compound of general formula [16] in presence of suitable nucleophiles such as alkylating agents like alkyl iodide or bromide or acylating agents such as acetyl chloride or alkyl chloroformate reagents in presence of suitable base such as NaH, pyridine in presence of suitable solvents such as THF, DCM. The protecting groups if present can then be removed or retained to provide the final compounds Synthetic Scheme 5:

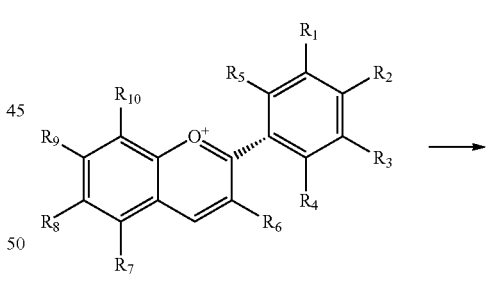

Cis 14
or
Trans 14

Any flavan-3-ol (12) such as catechin with or without a suitable protecting group such as benzyl on phenolic OH can be converted to compound [13] in presence of suitable oxidizing agents such as Dess-Martin periodinane in presence of suitable solvents such as THF or DCM. Compound [13] may be further functionalized to compound 14 with or without diastereoselectivity, exploiting different transformations of ketone group known in literature such as but not limited to cyanohydrins, oximes synthesis or halogenations or when treated with different Grignard reagents to obtain tertiary alcohols.

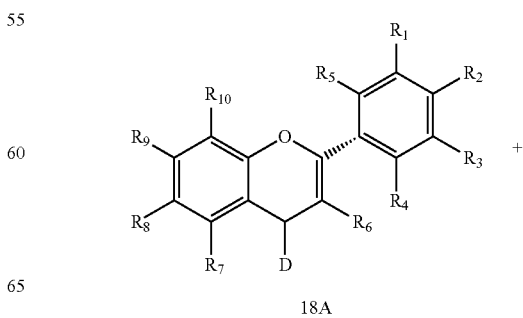

18A

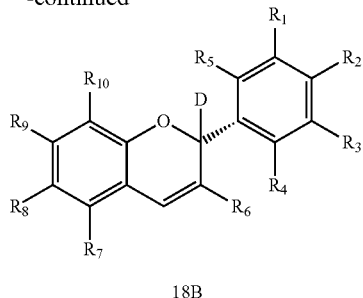

18B

Any flavan-3-ol intermediate such as cyanidin [17] with or without a suitable protecting group such as benzyl on phenolic OH can be converted to compound [18A] and [18B] in presence of suitable reducing agents such as NaCNBD$_4$ in presence of suitable solvents such as THF or DCM. Compounds [18A] and [18B] may be further reduced as well as deprotected in a single step when treated with Pd(OH)$_2$ in hydrogen atmosphere to obtain the final products with or without diastereoselectivity.

It is submitted that the synthetic schemes as disclosed herein are not meant to limit the scope of the invention, but are meant as general synthetic schemes representative for synthesizing all analogues of the present invention.

Salts and Isomers and Counter Ions

The present invention includes within its scope the salts and isomers. Compounds of the present invention after being novel may in some cases form salts which are also within the scope of this invention. All stereoisomers of the present compounds, such as those which may exist due to asymmetric carbons on the R substituents of the compound, including enantiomeric and diastereomeric forms, are contemplated within the scope of this invention.

Composition Containing the Novel Entities of the Invention

The present invention also contemplates a composition or formulation comprising the compounds of the present invention. The composition or formulation may be used for cosmetic or nutraceutical or pharmaceutical purposes. Further the compounds of the present invention can be used in combination with other pharmaceutical or nutraceutical agents.

In another aspect, the present invention is also drawn to the use of the compounds for indications wherein epicatechin and other polyphenols are found to be useful.

The compounds of the present invention may be used for inducing mitochondrial biogenesis. The compounds of the present invention may be useful as supplements/medication in meeting the muscle requirement by sports men/exercised muscles to meet the increasing energy demand. The compound of the present invention may be used for treating the diseases associated with mitochondria dysfunction.

Without being limited by theory, it is submitted that the novel analogues of the present invention exhibit substantially different pharmacokinetic, pharmacodynamic, and acute and long-term toxicity profiles in comparison to the other polyphenols. Further, they exhibit rapid oxidations and generally produce a detectable kinetic isotope effect that affects the pharmacokinetic, pharmacological, and/or toxicological profiles of a compound.

EXAMPLES

The following examples are representative of the disclosure, and provide detailed methods for preparing the compounds of the disclosure, including the preparation of the intermediate compounds. The preparation, of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions.

For all of the following examples, standard work-up and purification methods known to those skilled in the art may be utilized. Unless otherwise indicated, all temperatures are expressed in ° C. (degrees Centigrade). All reactions conducted at room temperature unless otherwise noted. Synthetic methodologies illustrated herein are intended to exemplify the applicable chemistry through the use of specific examples and are not indicative of the scope of the disclosure.

Example 1

Synthesis of (R,E)-2-(3,4-dihydroxyphenyl)-5,7-dihydroxychroman-3-one oxime [1001]

Step 1: Synthesis Tetrabenzylated Catechin [20] from Catechin [19]

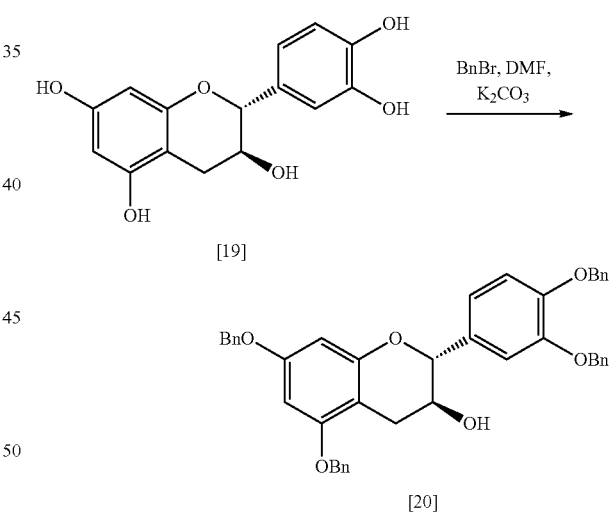

To a stirred solution of [19] (1.0 g, 3.4 mmol) in DMF, anhydrous K$_2$CO$_3$ (2.3 g, 17.0 mmol) was added at 0° C. under nitrogen atmosphere. After an additional stirring at this for 15 minutes at same temperature, benzyl bromide (2.0 ml, 17.0 mmol) was added drop-wise. The reaction temperature was allowed to increase up to 25° C. and stirring was continued for overnight. Consumption of [19] was monitored by TLC. After complete consumption of [19], water (50 ml) was added and organic layer was extracted with ethyl acetate (3×100 ml). The combined organic layers were washed with water, brine and dried over sodium sulphate. The organic layer was concentrated to afford light brown sticky material which was further purified using silica gel column chromatography using 8% ethyl acetate in hexane as eluent to afford [20] as white powder (1.5 g, 68%); ESIMS: 651 [M$^+$+1]

Step 2: Synthesis of [21] from Tetrabenzylated Catechin [20]

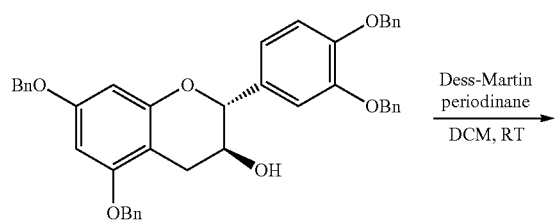

[20]

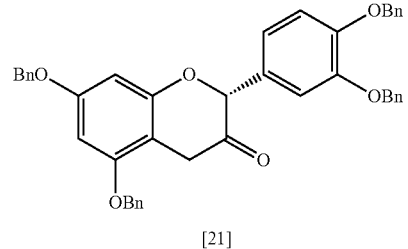

[21]

To a stirred solution of [20] (1.0 g, 1.53 mmol) in Dry DCM, Dess-Martin Periodinane (0.98 g, 23 mmol) was added in one portion at room temperature. After an additional, stirring for 6-7 h, saturated NaH$_2$CO$_3$ (20 ml) was added and was extracted with DCM (3×100 ml). The combined organic layers were washed with water and dried over sodium sulphate. The organic layer was concentrated to afford light pink sticky material which was further purified using silica gel flash column chromatography using DCM as eluent to afford off [21] as a white-pinkish solid powder (0.65 g, 71%); ESIMS: 649 [M$^+$1]

Step 3: Synthesis of [22] from [21]

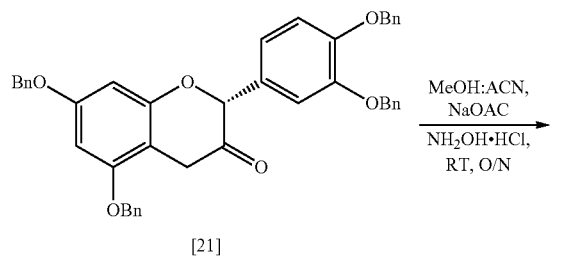

[21]

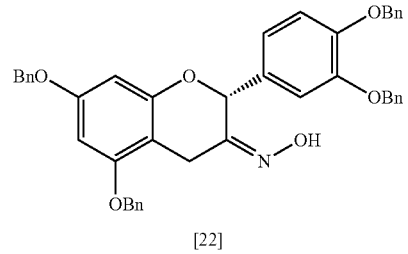

[22]

To a stirred solution of [21] (0.20 g, 0.30 mmol) in a mixture of acetonitrile (2 ml) and methanol (5 ml), ammonium acetate (0.03 g, 0.36 mmol) was added in one portion at room temperature. After additional stirring at this temperature for 10 min hydroxylamine hydrochloride (0.02 g, 0.36 mmol) was added. Consumption of [21] was monitored by TLC. After complete consumption of [21], the reaction mixture was concentrated and water (50 ml) was added. The organic layer was then extracted with ethyl acetate (2×100 ml). The combined organic layers were washed with water, brine and dried over sodium sulphate. The organic layer was concentrated to afford [22] as off white sticky solid which was used as such for further steps (0.12 g, 68%); ESIMS: 664 [M$^+$+1]

Step 4: Synthesis of 1001 from [22]

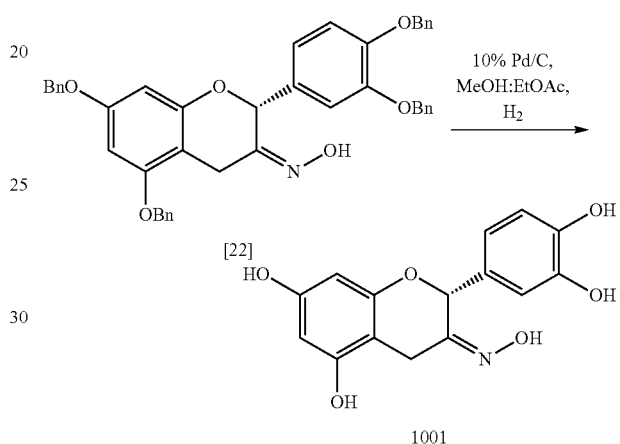

[22]

1001

To a stirred solution of [22] (0.15 g, 0.22 mmol) in a mixture of ethyl acetate and methanol (1:1, 5 ml), was added a slurry of 10% Pd/C (0.02 g) at room temperature. Hydrogen balloon pressure was applied and the reaction mixture was stirred for 1 hr at RT, followed by additional stirring of overnight at 50° C.-55° C. Reaction was monitored using TLC. The reaction mass was filtered over celite and excess of solvent was removed under vacuum to afford light brown sticky material, which was further purified using silica gel column and 6% methanol in dichloromethane as eluent to afford [1001] as off white sticky material (0.02 g, 25%); ESIMS: 304 [M$^+$1].

Example 2

Synthesis of (2R,3R)-2-(2,3-dihydroxyphenyl)-3-fluoro-chroman-5,7-diol [1010]

Step 1: Synthesis of [1010] from Catechin [19]

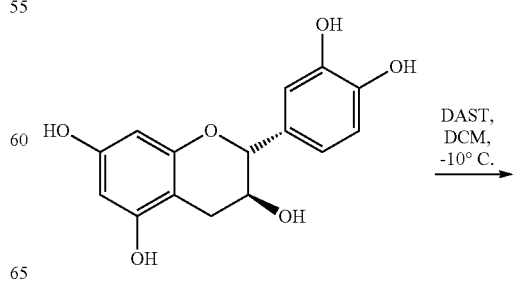

19

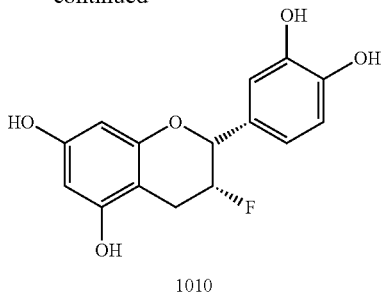

1010

To a stirred solution of [19] (0.10 g, 0.34 mmol) in Dry DCM at −10° C. was added DAST (0.20 ml, 1.0 mmol) dissolved in DCM to form a solution. The stirring was continued for 2 h before addition of saturated NaHCO$_3$ followed by extraction with DCM (2×50 ml). The combined organic layer was washed with brine and dried over sodium sulphate and concentrated to afford light brown sticky material. The crude reaction mixture was purified using Flash silica gel column and 1% MeOH in DCM as eluent to afford 1014 (0.01 g, 10%) as a light yellowish sticky material; ESIMS: 293 [M$^+$+1].

Example 3

Synthesis of (2R,3R)-2-(3,4-dihydroxyphenyl)-3-aminochroman-5,7-diol [1009]

Step 1: Synthesis of [23(A+B)] from [21]

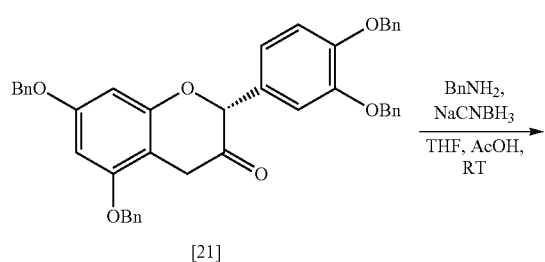

[21]

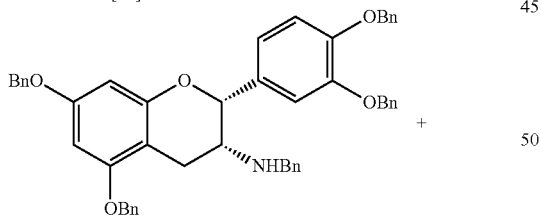

[23A]

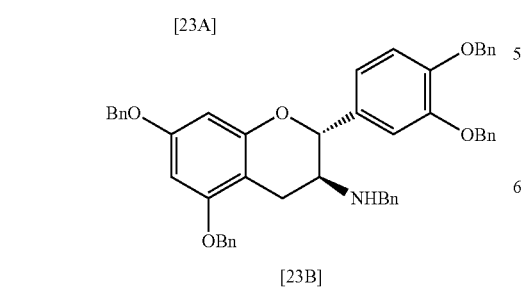

[23B]

To a stirred solution of [21] (0.50 g, 0.77 mmol) in dry THF, benzylamine (0.18 ml, 1.5 mmol) was added at room temperature under nitrogen atmosphere. After an additional stirring at this for 15 minutes at same temperature, acetic acid (3-4 drops) was added drop-wise. Further stirring at this temperature for 1 h, NaCNBH$_3$ (0.09 g, 1.5 mmol) was added. Consumption of [21] was monitored by TLC. After complete consumption of the starting material, water (50 ml) was added and organic layer was extracted with ethyl acetate (3×100 ml). The combined organic layers were washed with water, brine and dried over sodium sulphate. The organic layer was concentrated to afford light brown sticky material which was further purified using silica gel column chromatography using 5% ethyl acetate in hexane as eluent to afford [23] (0.21 g, 36%) and 15 (0.07 g, 13%) as a light yellow sticky material. ESIMS: 740 [M$^+$+1]

Step 2: Synthesis of 1009 from [23A]

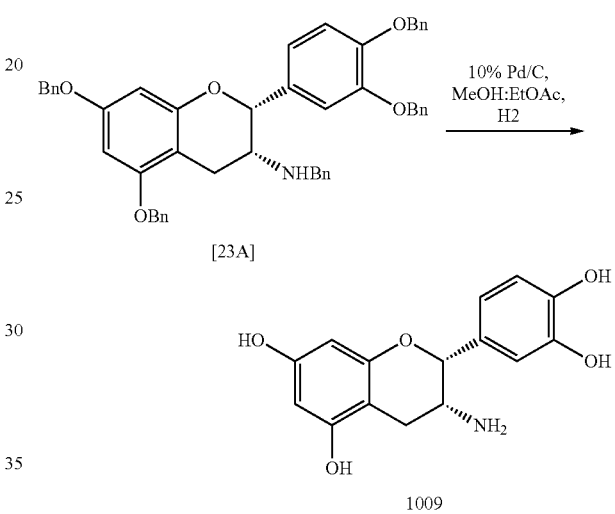

1009

To a stirred solution of [23A] (0.10 g, 0.13 mmol) in a mixture of ethyl acetate and methanol (1:1, 5 ml), was added a slurry of 10% Pd/C (0.02 g) at room temperature. Hydrogen balloon pressure was applied and the reaction mixture was stirred for overnight at RT. Reaction was monitored using TLC. The reaction mass was filtered over celite and excess of solvent was removed under vacuum at low temperature to afford light brown, sticky material, which was further purified using Prep HPLC to afford [1009] as light brown sticky material (0.01 g, 27%). ESIMS: 290 [M$^+$+1]

Example 4

Synthesis of Cis (±) 2-(4-hydroxyphenyl)chroman-3,7-diol [1004]

Step 1: Synthesis of 1-(4-benzyloxy)-2-hydroxyphenyl)ethanone from 1-(2,4-dihydroxyphenyl)ethanone

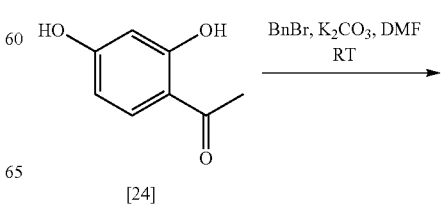

[24]

-continued

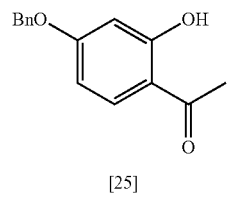

[25]

To a stirred solution of [24] (10.0 g, 65.78 mmol) in DMF (60 ml) was added $K_2CO_3$ (27.2 g, 197 mmol) at 0° C. under nitrogen atmosphere. After stirring at this temperature for 15 min, was added Benzyl bromide drop-wise (7.2 ml, 65.7 mmol). The temperature of reaction mixture was allowed to raise to room temperature and stirred it for overnight. TLC showed complete consumption of [24]. Reaction mixture was quenched with water (500 ml) and extracted with ethyl acetate (2×500 ml). The combined organic layer was washed with water, brine and dried over sodium sulphate. The organic layer was rotary evaporated to afford light brown sticky material. This crude product was loaded on to silica gel column and elated with 8% ethyl acetate/hexane to afford brown powder [25] (12 g, 75%); ESIMS: 242 [M$^+$+1].

Step 2: Synthesis of [27] from 1-(4-benzyloxy)-2-hydroxyphenyl) ethanone and [26]

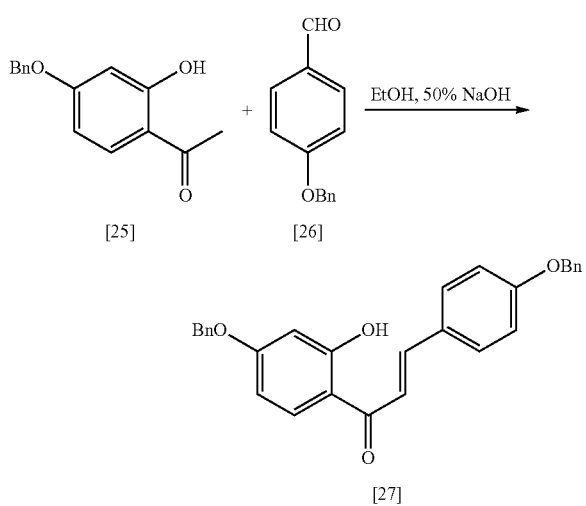

To a stirred solution of [25] (3.0 g, 12.3 mmol) in EtOH (30 ml) was added [26] (3.1 g, 14.8 mmol) and reaction mixture was heated to 50° C., then 50% aq.NaOH solution (9.0 ml) was added dropwise with constant stirring to reaction mixture at 50° C. and allowed to stir at rt for overnight. Completion of reaction was monitored, by checking TLC. TLC showed complete consumption of [25]. Reaction mixture was poured into crushed ice and neutralized with 5% HCl solution, crude product was obtained as yellow precipitate which was filtered through buchener funnel and crude product was recrystallised with aq.EtOH to obtained pure product [27] as a yellow powder. This pure product [27] (3.5 g, 64%) was used for further step. ESIMS: 436 [M$^+$+1]

Step 3: Synthesis of [28] from [27]

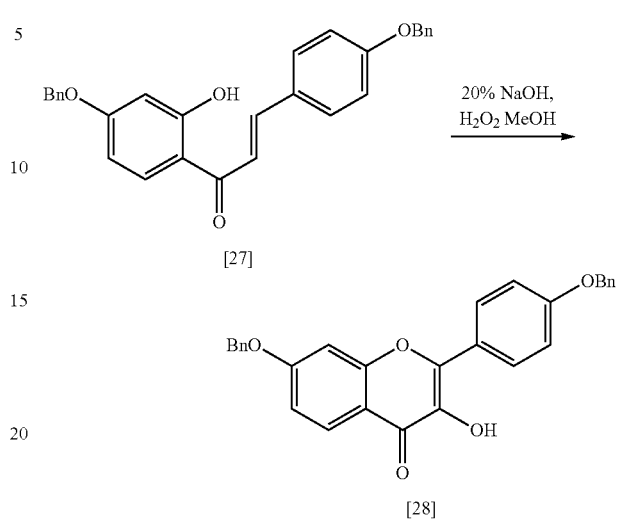

To a stirred solution of [27] (3.0 g, 6.88 mmol) in methanol (40 ml), was added 20% aq.NaOH (7.0 ml). The reaction mixture, was kept in an ice bath at 0° C. and 30% $H_2O_2$ (3.2 ml) was added, dropwise with constant stirring then reaction temperature was raised to RT and stirred at this temperature for overnight. Completion of reaction was monitored by c TLC. TLC showed complete consumption of [27]. Reaction mixture was acidified with cold 5% HCl solution. The yellow precipitate formed was filtered off through Buchner funnel and crude product was recrystallized with aq. EtOH to obtained pure product [28] as a yellow powder. This pure product [28] (1.7 g, 56%) was used for the next step; ESIMS: 450 [M$^+$+1]

Step 4: Synthesis of [29] from [28]

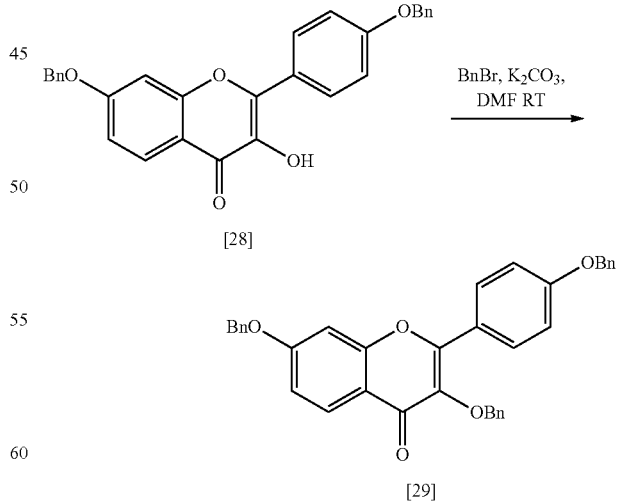

To a stirred solution of [28] (1.6 g, 3.55 mmol) in DMF was added $K_2CO_3$ (0.588 g, 4.26 mmol) at 0° C. coder nitrogen atmosphere. After stirring at this temperature for 15 min, was added Benzyl bromide drop-wise (0.42 ml, 3.55 mmol). The temperature of reaction mixture was allowed to rise to room temperature and stirred it for overnight TLC showed complete consumption of [28]. Reaction mixture was quenched with water (300 ml) and extracted with ethyl acetate (2×200 ml). The combined organic layer was washed with water, brine and dried over sodium sulphate. The organic layer was rotary evaporated to afford yellow solid. This erode product was washed with diethyl ether to afford light yellow powder [29] (1.5 g, 78%), ESIMS: 540 [M$^+$+1]

Step 5: Synthesis of [30] and [31] from [29]

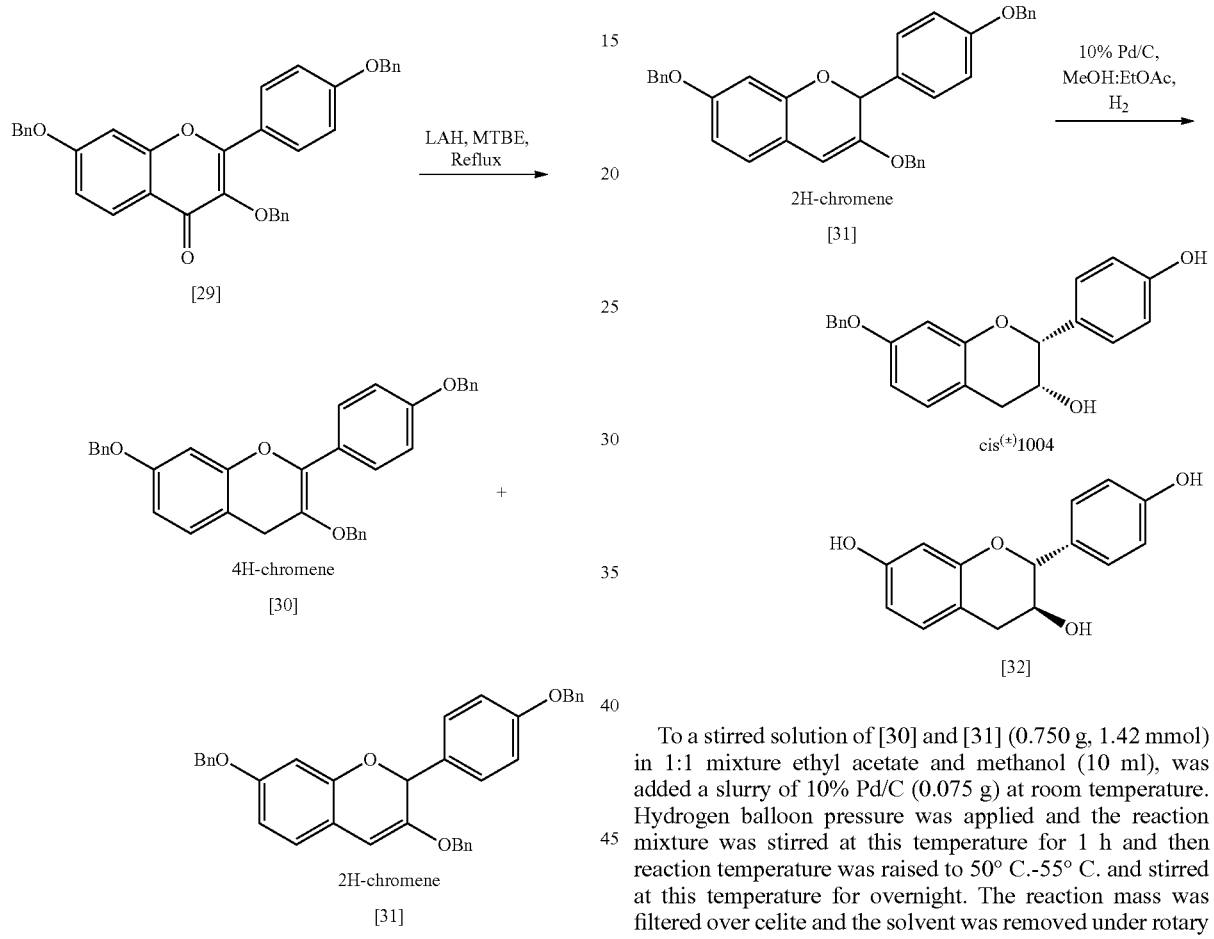

To a stirred solution of [29] (1.5 g, 2.77 mmol) in MTBE (20 ml) was added LAH (0.422 g, 11.1 mmol) at 40° C. under nitrogen atmosphere. After stirring at this temperature for 5 min, The temperature of reaction, mixture was allowed to raise to 80° C. for 2 h. Completion of reaction as monitored by TLC showed complete consumption of [29]. Reaction mixture was quenched with water (50 ml) and extracted with ethyl acetate (2×100 ml). The combined organic layer was washed with water, brine and dried over sodium sulphate. The organic layer was rotary evaporated to afford dark brown sticky material. This crude product was loaded on to silica gel column and elated with 100% DCM to afford light brown sticky material as a mixture of [30] and [31] (0.90 g, 61%). The mixture of [39] and [31] was used in the next step; ESIMS: 526 [M$^+$+1].

Step 6: Synthesis of [1004] from [30] and [31]

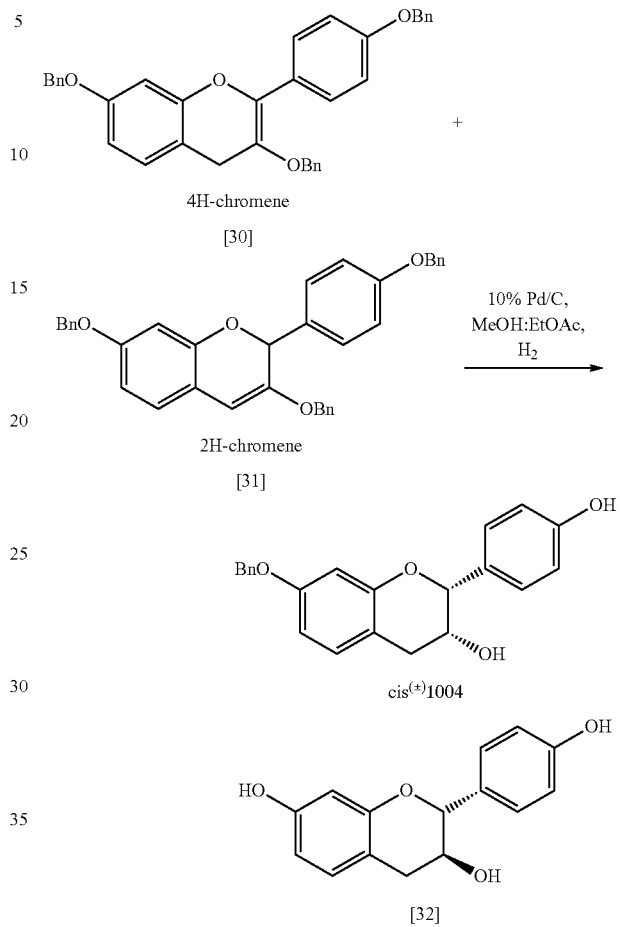

To a stirred solution of [30] and [31] (0.750 g, 1.42 mmol) in 1:1 mixture ethyl acetate and methanol (10 ml), was added a slurry of 10% Pd/C (0.075 g) at room temperature. Hydrogen balloon pressure was applied and the reaction mixture was stirred at this temperature for 1 h and then reaction temperature was raised to 50° C.-55° C. and stirred at this temperature for overnight. The reaction mass was filtered over celite and the solvent was removed under rotary evaporator to afford light brown sticky material. This crude product was purified by prep HPLC to afford cis racemic [1004] as an off white powder (0.035 g, 10%) and its trans isomer [32] as an off white powder (0.013 g, 4%); ESIMS: 258 [M$^+$+1].

Example 5

Synthesis of Cis (±) 2-(3,4-dihydroxyphenyl)chroman-3,7-diol [1003] was carried out by procedure as described for [1004] with [25] and 3,4-bis(benzyloxy)benzaldehyde as starting material.

Example 6

Synthesis of Cis (±) 2-(3-hydroxyphenyl)chroman-3,7-diol [1007] was carried out by procedure as described for [1004] with [25] and 3-bis(benzyloxy)benzaldehyde as starting material.

Example 7

Synthesis of Cis (±) 3-hydroxychroman-2-yl)benzene-1,2-diol

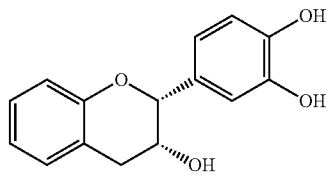

[1002]

Step 1: Synthesis of (E)-3-(3,4-bis-(benzyloxy)phenyl)-1-(2-hydroxyphenyl)prop-2-en-1-one [35]

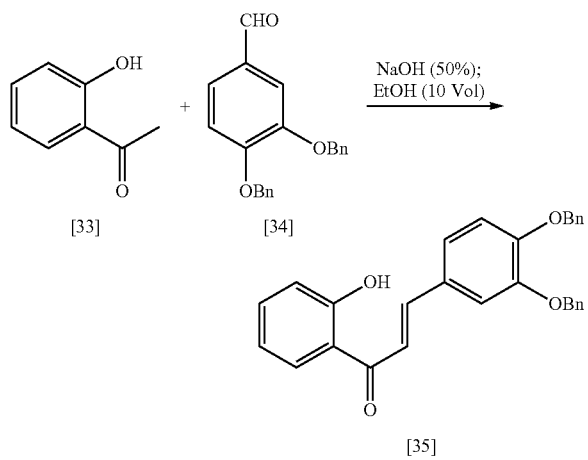

To a stirred solution of compound [33] (2.0 g, 14.68 mmol) and compound [34] (1.75 g, 8.28 mmol) in EtOH (20 ml), were added aq. NaOH solution (2 g dissolve in 10 ml water). Reaction mixture was stirred at 50° C. for 30 min and then stirred at RT for overnight. Consumption of [33] and [34] were monitored by TLC. Reaction mixture was acidified with 2N HCl to pH 4, water (50 ml) was added and organic layer was extracted with ethyl acetate (2×100 ml). The combined organic layers were washed with water, brine and dried over sodium sulphate. The organic layer was concentrated to afford light yellow sticky material which was further purified using recrystallisation by using EtOH to afford [35] as light yellow solid (3.04 g, 55%). ESIMS: 437 [M$^+$+1]

Step 2: Synthesis of 2-(3,4-bis(benzyloxy)phenyl)-3-hydroxy-4H-chromen-4-one (36)

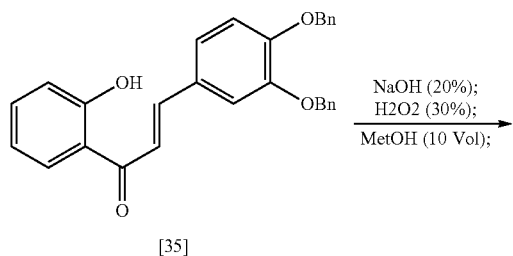

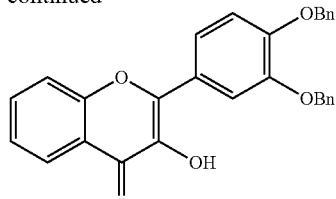

[36]

Compound [35] (2.5 g, 5.77 mmol) was stirred at 0° C. for 10 minute in EtOH (20 ml). Then solution of 20% NaOH (8 ml) was added in reaction mixture followed by 30% H$_2$O$_2$ (10 ml) was added and stirred at 0° C. for 4-5 hrs. Then reaction mixture was kept in freeze for overnight at 4° C. Consumption of [35] was monitored by TLC. Reaction mixture was acidified with 2N HCl to pH 3, and organic layer was extracted with ethyl acetate (2×100 ml). The combined organic layers were washed with water, brine and dried over sodium sulphate. The organic layer was concentrated to afford light yellow sticky material which was further purified using recrystallisation by using EtOH to afford [36] as light yellow solid (1.56 g, 62%). ESIMS: 451 [M$^+$1]

Step 3: Synthesis of 3-(benzyloxy)-2-(3,4-bis(benzyloxy)phenyl)-4H-chromen-4-one [37]

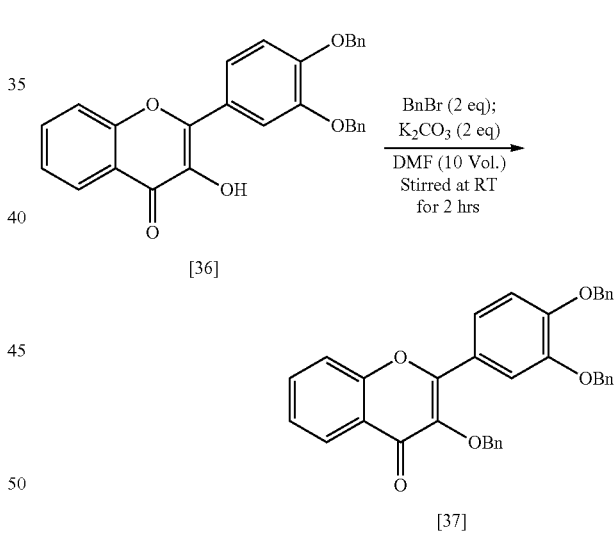

To a stirred solution of [36] (1.40 g, 3.11 mmol) in DMF, anhydrous K$_2$CO$_3$ (0.865 g, 6.22 mmol) was added at RT under nitrogen atmosphere. After an additional stirring at this for 15 minutes at same temperature, benzyl bromide (0.57 ml 4.66 mmol) was added drop-wise in reaction mixture. The reaction mixture was stirred continued for 2-3 h at RT. Consumption of [36] was monitored by TLC. After complete consumption of [36], water (20 ml) was added and organic layer was extracted with ethyl acetate (2×50 ml). The combined organic layers were washed with water, brine and dried over sodium sulphate. The organic layer was concentrated to afford light brown sticky material which was further purified by crystallization using EtOH to afford [37] as light yellow solid (1.70 g, 90%). ESIMS: 541 [M$^+$+1]

Step 4: Synthesis of Compound [38] and [39]

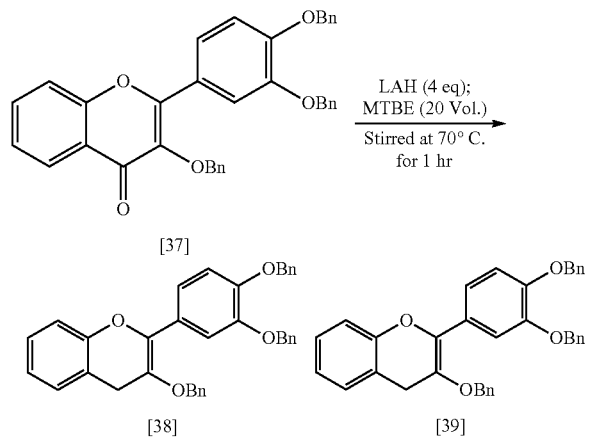

To a stirred solution of [37] (1.30 g, 2.41 mmol) in MTBE (30 ml), LAH (0.366 g, 0.647 mmol) was added at RT under nitrogen atmosphere. Reaction mixture temperature was increased to 70° C. and stirred at this temperature for 1 hrs. Consumption of [37] was monitored by TLC. After complete consumption of [37], reaction mixture was cooled to 0° C. and then quenched by NH$_4$Cl (25 ml). Water (20 ml) was added and organic layer was extracted with ethyl acetate (2×50 ml). The combined organic layers were washed with water, brine and dried over sodium sulphate. The organic layer was concentrated to afford off-white sticky material of compound [38] and compound [39] (1.20 g, 80%), which was directly used for next step. ESIMS: 527 [M$^+$+1]

Step 5: Synthesis of 1002

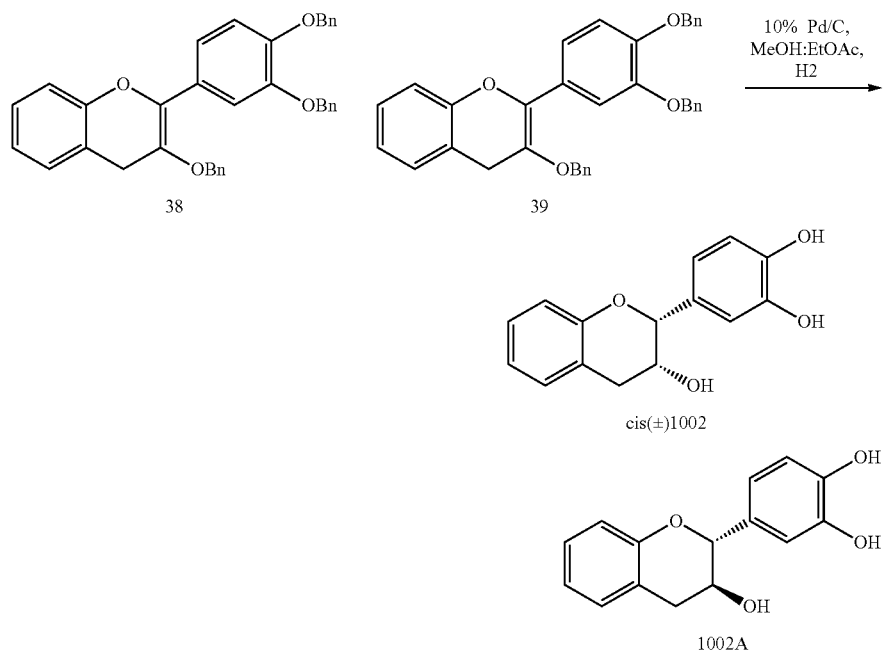

To a stirred solution of [38] and [39] (0.500 g, 9.53 mmol) in a mixture of ethyl acetate and methanol (1:1, 20 ml), was added a slurry of 10% Pd/C (0.05 g) at room temperature under nitrogen atmosphere. Hydrogen balloon pressure was applied and the reaction mixture was stirred for 1 h at RT, followed by additional stirring of overnight at 50° C.-55° C. Reaction was monitored by using TLC. The reaction mass was filtered over celite bed and excess of solvent was removed under vacuum to afford light brown sticky material, which was further purified using silica gel column, and 2% methanol in dichloromethane as eluent to afford cis racemic 1002 (0.090 g, 40%) as an off-white solid and 1002A (0.010 g, 10%). ESIMS: 250 [M$^+$+1]

Example 8

Synthesis of Cis (±) 2-(3-hydroxyphenyl)chroman-3-ol [1011] was carried out by procedure as described for 1002 with [33] and 3-(benzyloxy)benzaldehyde as starting material.

Example 9

Synthesis of Cis (±) 2-(4-hydroxyphenyl)chroman-3-ol [1012] was carried out by procedure as described for 1002 with [33] and 4-(benzyloxy)benzaldehyde as starting material.

Example 10

Synthesis of Cis (±) 2-(4-hydroxyphenyl)chroman-3,5-diol [1006]

Step 1: Synthesis of 1-(2-(benzyloxy)-4-hydroxyphenyl)-ethanone [41]

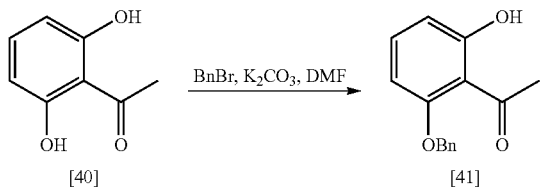 [SMILES: CC(=O)c1c(O)cccc1O ; CC(=O)c1c(O)cccc1OCc1ccccc1]

To a stirred solution of [40] (2.0 g, 1.34 mmol) in DMF, anhydrous K$_2$CO$_3$ (2.17 g, 15.77 mmol) was added at RT under nitrogen atmosphere. After an additional stirring at this for 15 minutes at same temperature, benzyl bromide (1.92 ml, 15.77 mmol) was added drop-wise. The reaction mixture was stirred continuously for overnight at RT. Consumption of [40] was monitored by TLC. After complete consumption of [40], water (50 ml) was added and organic layer was extracted with ethyl acetate (2×100 ml). The combined organic layers were washed with water, brine and dried over sodium sulphate. The organic layer was concentrated to afford light brown sticky material which was further purified using silica gel column chromatography using 5% ethyl acetate in hexane as eluent to afford [41] as white powder (2.1 g, 80%). ESIMS: 243 [M$^+$+1]

Step 2: Synthesis of (E)-1-(2-(benzyloxy)-6-hydroxyphenyl)-3-(4-(benzyloxy)-phenyl)-prop-2-en-1-one (43)

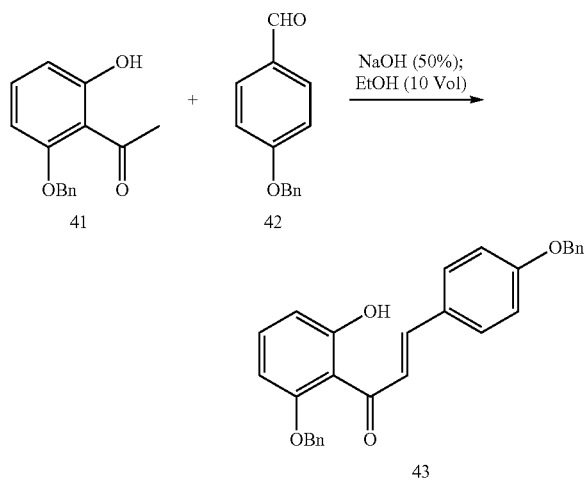

To a stirred solution of compound [41] (2.0 g, 8.28 mmol) and compound [42] (1.75 g, 8.28 mmol) in EtOH (20 ml), were added aq. NaOH solution (1 g dissolve in 6 ml water). Reaction mixture was stirred at 50° C. for 30 min and then stirred at RT for overnight. Consumption of [41] and [42] were monitored by TLC. Reaction mixture was acidified with 2N HCl to pH 4, water (50 ml) was added and organic layer was extracted with ethyl acetate (2×100 ml). The combined organic layers were washed with water, brine and dried over sodium sulphate. The organic layer was concentrated to afford light yellow sticky material which was further purified using recrystallisation by using EtOH to afford [43] as light yellow solid (2.0 g, 50%). ESIMS: 437 [M$^+$+1]

Step 3: Synthesis of 5-(benzyloxy)-2-(4-(benzyloxy)-phenyl)-3-hydroxy-4H-chromen-4-one (44)

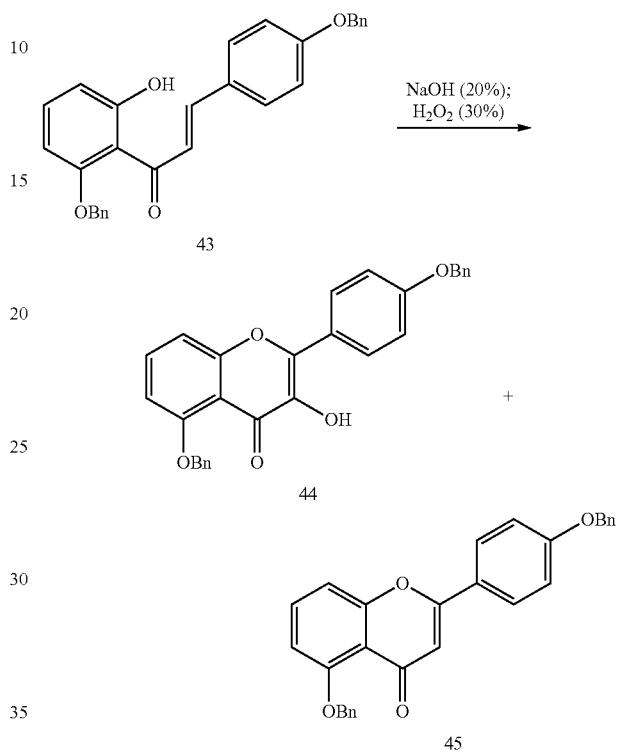

Compound [43] (1.5 g, 3.44 mmol) was stirred at 0° C. for 10 minute in EtOH (20 ml). Then solution of 20% NaOH (10 ml) was added in reaction mixture followed by 30% H2O2 (10 ml) was added and stirred at 0° C. for 4-5 h. Then reaction mixture was kept in freeze for overnight at 4° C. Consumption of [43] was monitored by TLC. Reaction mixture was acidified with 2N HCl to pH 3, and organic layer was extracted with ethyl acetate (2×100 ml). The combined organic layers were washed with water, brine and dried over sodium sulphate. The organic layer was concentrated to afford light yellow sticky material which was further purified using recrystallisation by using EtOH to afforded [44] and [45] as a light yellow solid (890 mg, 50%). ESIMS: 451 [M$^+$+1]

Step 4: Synthesis of 3,5-bis-(benzyloxy)-2-(4-(benzyloxy)-phenyl)-4H-chromen-4-one (46)

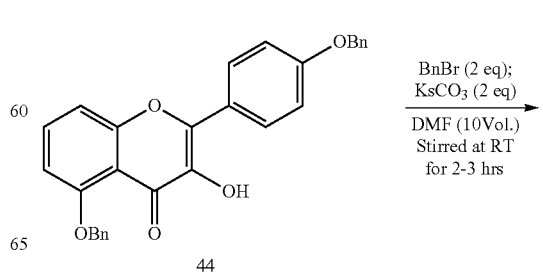

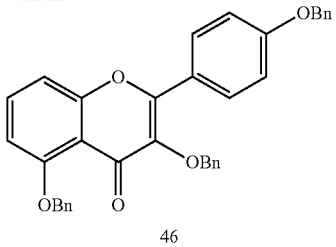

To a stirred solution of [44] (0.6 g, 1.33 mmol) in DMF, anhydrous K$_2$CO$_3$ (0.36 g, 2.66 mmol) was added at RT under nitrogen atmosphere. After an additional stirring at this for 15 minutes at same temperature, benzyl bromide (0.325 ml, 2.66 mmol) was added drop-wise in reaction mixture. The reaction mixture was stirred continued for 2-3 hrs at RT. Consumption of [44] was monitored by TLC. After complete consumption of [44], water (20 ml) was added and organic layer was extracted with ethyl acetate (2×50 ml). The combined organic layers were washed with wafer, brine and dried over sodium sulphate. The organic layer was concentrated to afford light brown sticky material which was further purified by crystallization using EtOH to afford [46] as light yellow solid (0.3 g, 52%). ESIMS: 541 [M$^+$+1]

Step 5: Synthesis of Compound 62 (A)+62 (B) from [61]

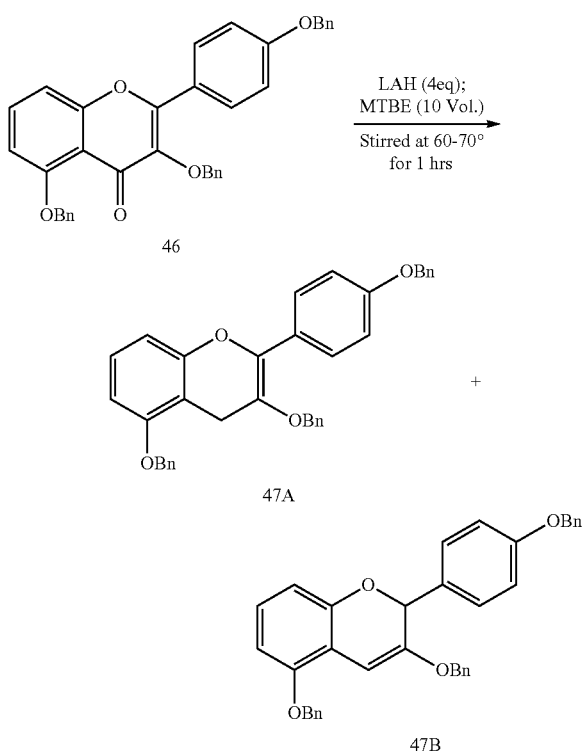

To a stirred solution of [46] (0.5 g, 9.25 mmol) in MTBE (20 ml), LAH (0.140 g, 37.03 mmol) was added at RT under nitrogen atmosphere. Reaction mixture temperature was increased to 70° C. and stirred at this temperature for 1 hrs. Consumption of [46] was monitored by TLC. After complete consumption of [46], reaction mixture was cooled to 0° C. and then quenched by NH$_4$Cl (25 ml). Water (20 ml) was added and organic layer was extracted with ethyl acetate (2×50 ml). The combined organic layers were washed with water, brine and dried over sodium sulphate. The organic layer was concentrated to afford off-white sticky material of compound 47 (A+B) (0.4 g, 80%), which was directly used for next stop. ESIMS: 527 [M$^+$+1]

Step 6: Synthesis of 2-(4-hydroxyphenyl)-chroman-3,5-diol (1006)

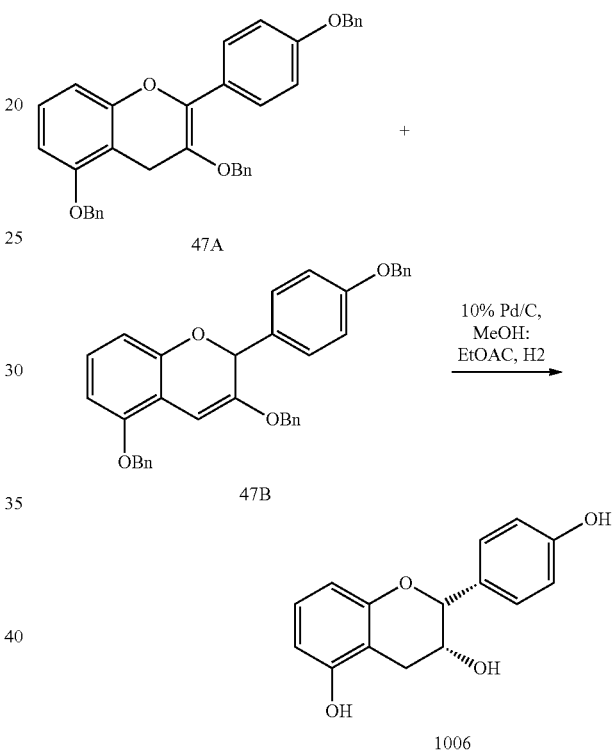

To a stirred solution of 47 (A+B) (0.400 g, 0.76 mmol) m a mixture of ethyl acetate and methanol (1:1, 20 ml), was added a slurry of 10% Pd/C (0.04 g) at room temperature under nitrogen atmosphere. Hydrogen balloon pressure was applied and the reaction mixture was stirred for 1 hr at RT, followed by additional stirring of overnight at 50° C.-55° C. Reaction was monitored by using TLC. The reaction mass was filtered over celite bed and excess of solvent was removed under vacuum to afford light brown sticky material, which was further purified using silica gel column and 2% methanol in dichloromethane as eluent to afforded cis racemic 1006 (0.028 g, 30%) as an off-white solids. ESIMS: 259 [M$^+$+1]

Example 11

Synthesis of Cis (±) 2-(3-hydroxyphenyl)chroman-3,5-diol [1005] was carried out by procedure as described for 1006 with [41] and 3-(benzyloxy)benzaldehyde as starting material.

Example 12

Synthesis of Cis (±) 2-(3,4-dihydroxyphenyl)chroman-3,5-diol [1013] was carried out by procedure as described for 1006 with [41] and 3,4-(benzyloxy)benzaldehyde as starting material.

Example 13

Synthesis of 2-(3-methoxy-4-methylphenyl)chromane-3,7-diol [1026] and 2-(3-hydroxy-4-methylphenyl)chromane-3,7-diol [1027] was carried out by procedure as described for 1004 with [25] and 3-methoxy-4-methylbenzaldehyde as starting material. [1026] ESIMS: 287 [M$^+$+1][1027] ESIMS: 272 [M$^+$+1]

Example 14

Synthesis of 2-(4-fluoro-3-methoxyphenyl)chromane-3,7-diol [1028] and 2-(4-fluoro-3-hydroxyphenyl)chromane-3,7-diol [1029] was carried out by procedure as described for 1004 with [25] and 4-fluoro-3-methoxybenzaldehyde as starting material. [1028] ESIMS: 290 [M$^+$+1][1029] ESIMS: 276 [M$^+$+1]

Example 15

Synthesis of Cis (±) 2-(3-methoxyphenyl)chroman-3,7-diol, Cis (±) 2-(3-hydroxyphenyl)-7-methoxychroman-3-ol, Cis(±)methoxy-2-(3-methoxyphenyl)chroman-ol [1017, 1018 and 1019]

Step 1: Synthesis of [1017], [1018] and [1019] from [1007]

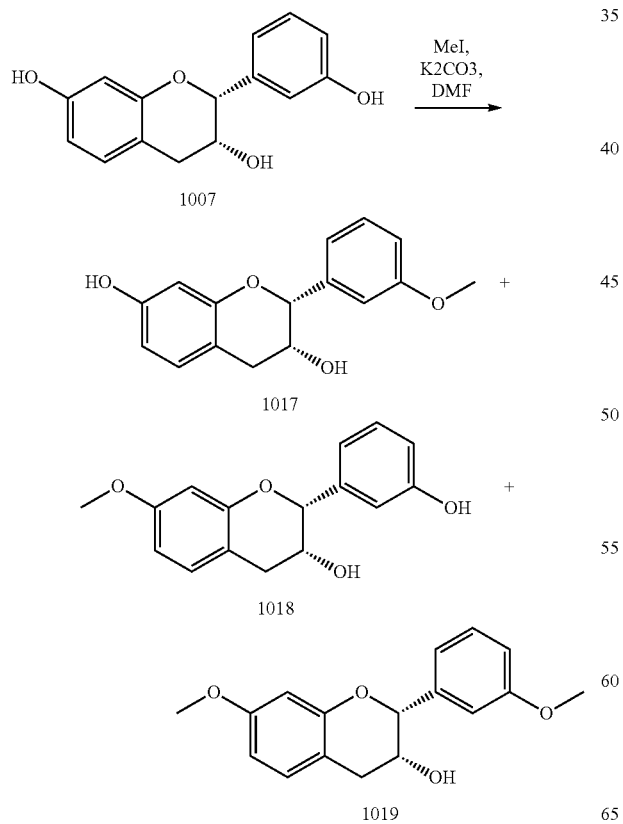

To a stirred solution of [1007] (0.12 g, 0.40 mmol) in DMF, anhydrous K$_2$CO$_3$ (0.12 g, 0.93 mmol) was added at 0° C. under nitrogen atmosphere. After an additional stirring for 15 minutes at same temperature. Methyl iodide (0.05 ml, 0.93 mmol) was added drop-wise. The reaction temperature was allowed to increase up to 25° C. and stirring was continued for 4 h. Consumption of [1007] was monitored by TLC. After complete consumption of [1007], water (50 ml) was added and organic layer was extracted with ethyl acetate (2×50 ml). The combined organic layers, were washed with water, brine and dried over sodium sulphate. The organic layer was concentrated to afford light brown sticky material which was further purified using silica gel column chromatography using 5% ethyl acetate/hexane as eluent to afford [1017] as light green sticky material (0.05 g, 37%), [1018] and [1019] as light yellow sticky material (0.02 g, 16%). [1019] ESIMS: 287 [M$^+$+1] [1017] and [1018] ESIMS: 272 [M$^+$+1]

Example 16

Synthesis of Cis (±)4-(3,7-dihydroxychroman-2-yl)phenyl acetate [1022], Cis (±) 3-hydroxy-2-(4-hydroxyphenyl)chroman-7-yl acetate [1023] and Cis (±)4-(7-acetoxy-3-hydroxychroman-2-yl)phenyl acetate [1024]

Step 1: Synthesis of [1022], [1023] and [1024] from [1007]

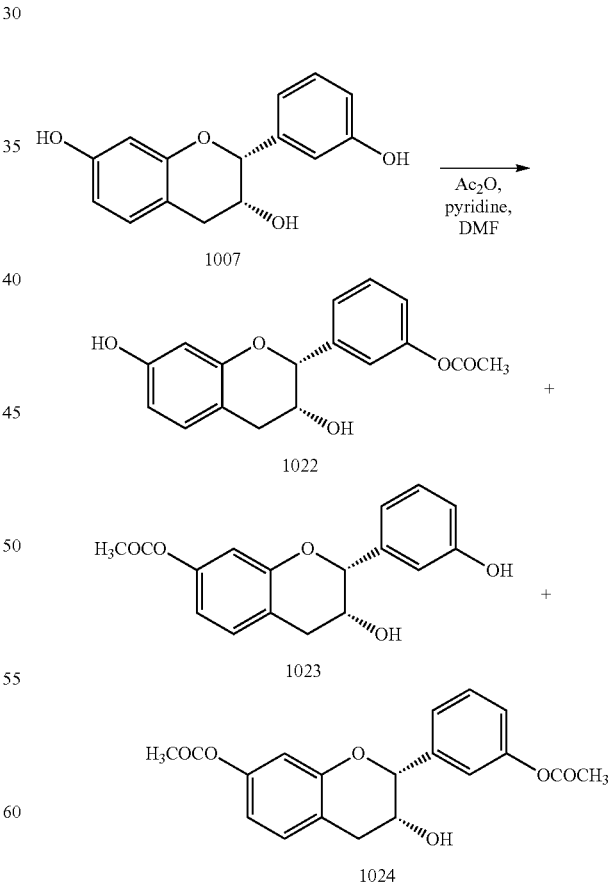

To a stirred solution of [1007] (0.2 g, 0.77 mmol) in DMF, pyridine (0.12 ml, 1.5 mmol) was added at 0° C. under nitrogen atmosphere. After an additional stirring for 5 minutes at same temperature, Acetic anhydride (0.15 ml, 1.5 mmol) was added drop-wise. The reaction temperature was allowed to increase up to 25° C. and stirring was continued for 1 h. Consumption of [1007] was monitored by TLC. After complete consumption of [1007], water (50 ml) was added and organic layer was extracted with ethyl acetate (2×50 ml). The combined organic layers were washed with water, brine and dried over sodium sulphate. The organic layer was concentrated to afford light brown sticky material which was further purified using silica gel column chromatography using 5% ethyl acetate/hexane as eluent to afford [1024] as light yellow sticky material (0.08 g, 30%), [1022] and [1023] as yellow sticky material (0.04 g, 17%). [1024] ESIMS: 343 [M$^+$+1] [1022] and [1023] ESIMS: 301 [M$^+$+1]

Example 17

Synthesis of 2-(3-hydroxyphenyl)-3-propoxychroman-7-ol [1030]

Step 1: Synthesis of [48] from [1007]

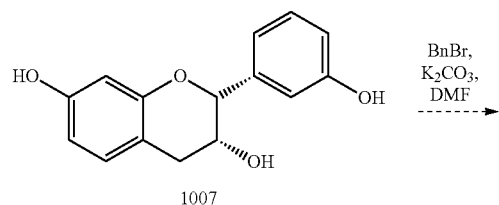

To a stirred solution of [1007] (0.15 g, 0.58 mmol) in DMF, anhydrous K$_2$CO$_3$ (0.24 g, 1.14 mmol) was added at RT under nitrogen atmosphere. After an additional stirring for 15 minutes at same temperature, benzyl bromide (0.13 ml, 1.16 mmol) was added drop-wise in reaction mixture. The reaction mixture was stirred continued for overnight at RT. Consumption of [1007] was monitored by TLC. After complete consumption of [1007], water (20 ml) was added and organic layer was extracted with ethyl acetate (2×50 ml). The combined organic layers were washed with water, brine and dried over sodium sulphate. The organic layer was concentrated to afford light brown sticky material which was further purified using silica gel column chromatography using 5% ethyl acetate/hexane as eluent to afford [48] as off-white sticky material (0.17 g, 67%). [81] ESIMS: 439 [M$^+$+1]

Step 2: Synthesis of [49] from [48]

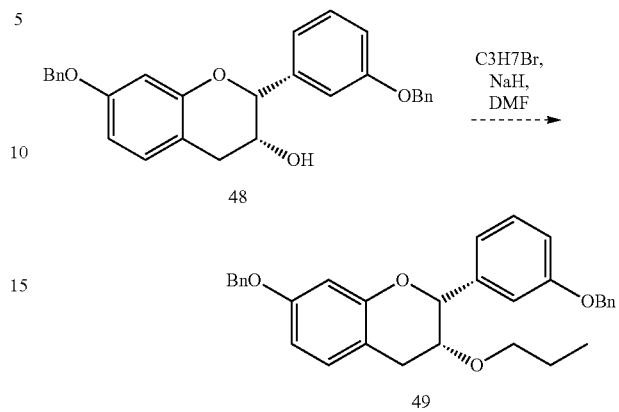

To a stirred solution of [48] (0.25 g, 0.57 mmol) in DMF, Sodium hydride (0.45 g, 1.1 mmol) was added at RT under nitrogen atmosphere. After an additional stirring for 15 minutes at same temperature, propyl bromide (0.13 ml, 1.1 mmol) was added drop-wise in reaction mixture. The reaction mixture was stirred continued for overnight at RT. Consumption of [48] was monitored by TLC. After complete consumption of [48], water (20 ml) was added and organic layer was extracted with ethyl acetate (2×50 ml). The combined organic layers were washed with water, brine and dried over sodium sulphate. The organic layer was concentrated to afford light brown sticky material which was further purified using silica gel column chromatography using 7% ethyl acetate/hexane as eluent to afford [49] as off-white sticky material (0.20 g, 73%), [49] ESIMS: 481 [M$^+$+1]

Step 3: Synthesis of [1030] from [49]

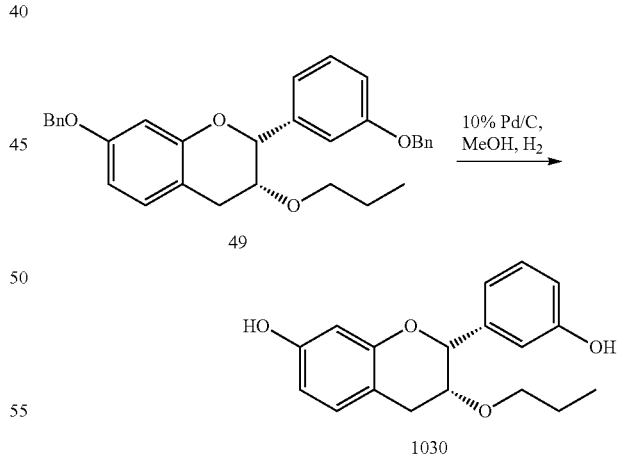

To a stirred solution of [49] (0.20 g, 0.4 mmol) in a mixture of ethyl acetate and methanol (1:1, 20 ml), was added a slurry of 10% Pd/C (0.02 g) at room, temperature under nitrogen atmosphere. Hydrogen balloon pressure was applied and the reaction mixture was stirred for 1 hr at RT, followed by additional stirring of overnight at 50° C.-55° C. Reaction was monitored by using TLC. The reaction mass was filtered over celite bed and excess of solvent was removed under vacuum to afford light brown sticky material, which was further purified using silica gel column and 2% methanol in dichloromethane as eluent to afforded [1030] (0.9%, 72%) as an off-white solid. ESIMS: 301 [M++1]

Example 18

Synthesis of Cis (±) 2-(4-hydroxyphenyl)chroman-3,5,7-triol [1008]

Step 1: Synthesis of 1-(2,4-bis(benzyloxy)-6-hydroxyphenyl)-ethanone

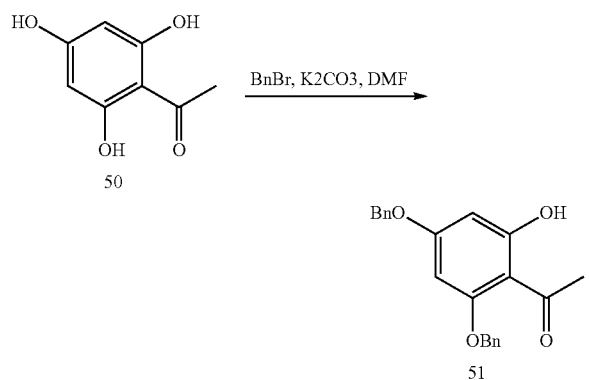

To a stirred solution of [50] (3.0 g, 16.19 mmol) in DMF, anhydrous K$_2$CO$_3$ (5.56 g, 40.32 mmol) was added at 0° C. under nitrogen atmosphere. After an additional stirring at this for 15 minutes at same temperature, benzyl bromide (4.92 ml, 40.32 mmol) was added drop-wise. The reaction temperature was allowed to increase up to 23° C. and stirring was continued for overnight. Consumption of [50] was monitored by TLC. After complete consumption of [50], water (50 ml) was added and organic layer was extracted with ethyl acetate (2×100 ml). The combined organic layers were washed with water, brine and dried over sodium sulphate. The organic layer was concentrated to afford light brown sticky material which was further purified using silica gel column chromatography using 5% ethyl acetate/hexane as eluent to afford [51] as white powder (3.2 g, 70%). ESIMS: 349 [M$^+$1]

Step 2: Synthesis of (E)-3-(4-(benzyloxy)phenyl)-1-(2,4-bis(benzyloxy)-6-hydroxyphenyl)-prop-2-en-1-one

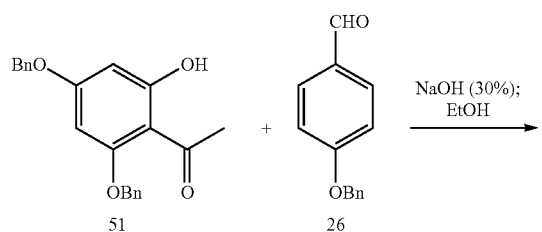

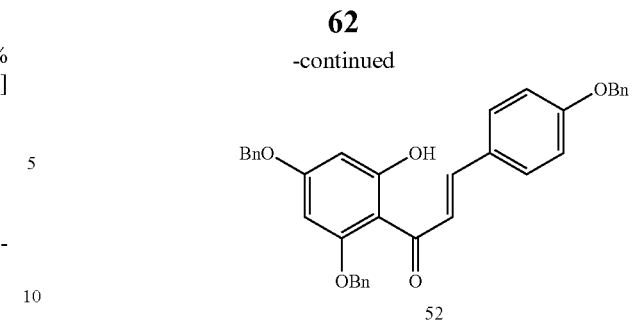

To a stirred solution of compound [51] (2.0 g, 5.74 mmol) and compound [26] (1.21 g, 5.74 mmol) in EtOH (20 ml), were added aq. NaOH solution (2 g dissolve in 10 ml water). Reaction mixture was stirred at 50° C. for 30 min and then stirred at RT for overnight. Consumption of [51] and [26] were monitored by TLC. Reaction mixture was acidified with 2N HCl to pH 4, water (50 ml) was added and organic layer was extracted with ethyl acetate (2×100 ml). The combined organic layers were washed with water, brine and dried over sodium sulphate. The organic layer was concentrated to afford light yellow sticky material which was further purified using recrystallisation by using EtOH to afford [52] as light yellow solid (2.0 g, 65%). ESIMS: 543 [M$^+$1]

Step 3: Synthesis of 5,7-bis(benzyloxy)-2-(4-(benzyloxy)phenyl)-3-hydroxy-4H-chromen-4-one

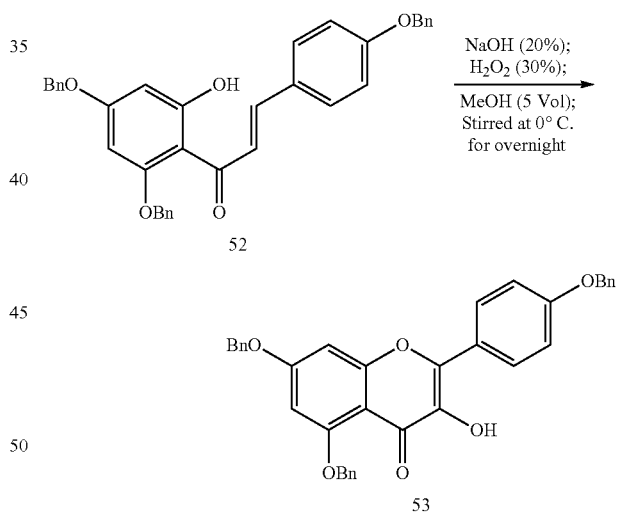

Compound [52] (1.8 g, 3.32 was stirred at 0° C. for 10 minute in EtOH (20 ml). Then solution of 20% NaOH (8 ml) was added in reaction mixture followed by 38% H$_2$O$_2$ (20 ml) was added and stirred at 0° C. for 4-5 hrs. Then reaction mixture was kept in freeze for overnight at 4° C. Consumption of [52] was monitored by TLC. Reaction mixture was acidified with 2N HCl to pH 3, and organic layer was extracted with ethyl acetate (2×100 ml). The combined organic layers were washed with water, brine and dried over sodium sulphate. The organic layer was concentrated to afford light yellow sticky material which was further purified using recrystallisation by using EtOH to afford [53] as light yellow solid (1.3 g, 60%). ESIMS: 557 [M$^+$+1]

Step 4: Synthesis of 3,5,7-tris(benzyloxy)-2-(4-(benzyloxy)phenyl)-4H-chromen-4-one

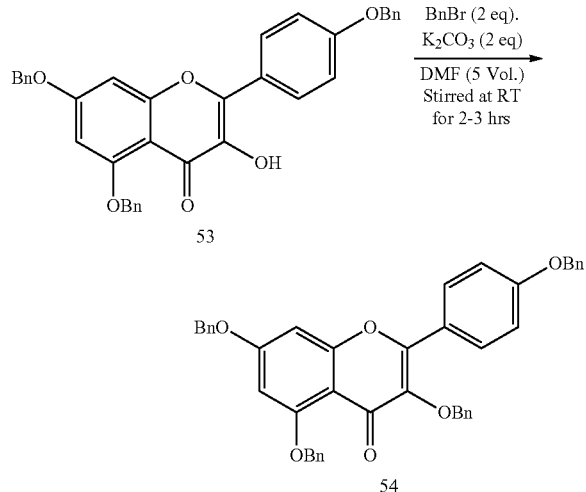

To a starred solution of [53] (1.25 g, 2.24 mmol) in DMF, anhydrous K$_2$CO$_3$ (0.370 g, 2.69 mmol) was added at RT under nitrogen atmosphere. After an additional stirring at this for 15 minutes at same temperature, benzyl bromide (0.330 ml, 2.69 mmol) wax added drop-wise in reaction mixture. The reaction mixture was stirred, continuously for 2-3 hrs at RX. Consumption of [53] was monitored by TLC. After complete consumption of [53], water (20 ml), was added and organic layer was extracted with ethyl acetate (2×50 ml). The combined organic layers were washed with water, brine and dried over sodium sulphate. The organic layer was concentrated to afford light brown sticky material which was further purified by crystallization using EtOH to afford [54] as light yellow solid (0.900 g, 60%). ESIMS: 646 [M$^+$+1]

Step 5: Synthesis of Compound 55(A)+55(B)

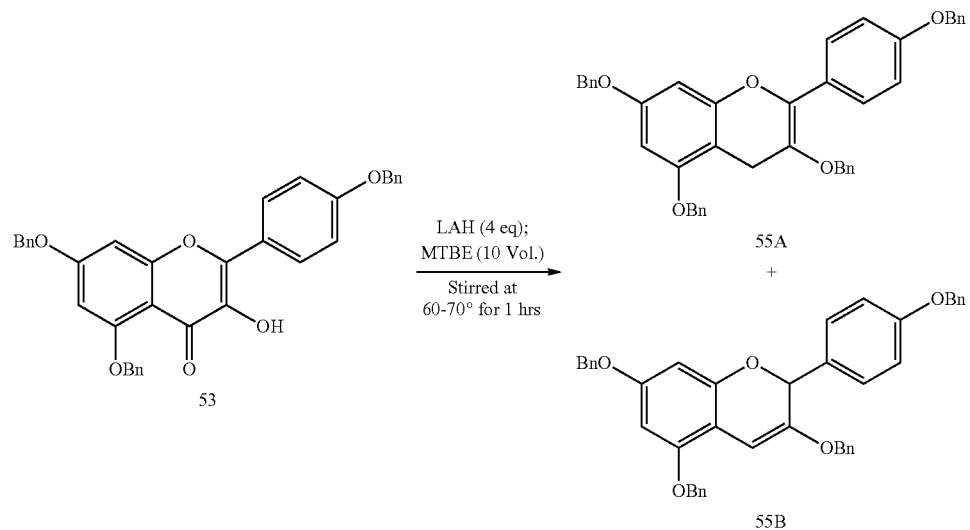 [SMILES: O=c1c(O)c(-c2ccc(OCc3ccccc3)cc2)oc2cc(OCc3ccccc3)cc(OCc3ccccc3)c12 ; C1=C(OCc2ccccc2)C(c2ccc(OCc3ccccc3)cc2)Oc2cc(OCc3ccccc3)cc(OCc3ccccc3)c21 ; c1ccc(COC2=C(c3ccc(OCc4ccccc4)cc3)Oc3cc(OCc4ccccc4)cc(OCc4ccccc4)c3C2)cc1]

To a stirred solution of [54] (0.950 g, 1.47 mmol) in MTBE (20 ml), LAH (0.223 g, 5.82 mmol) was added at RT under nitrogen atmosphere. Reaction mixture temperature was increased to 70° C. and stirred at this temperature for 1 hrs. Consumption of [54] was monitored by TLC. After complete consumption of [54], reaction mixture was cooled to 0° C. and then quenched by NH$_4$Cl (25 ml). Water (20 ml) was added and organic layer was extracted with ethyl acetate (2×50 ml). The combined organic layers were washed with water, brine and dried over sodium sulphate. The organic layer was concentrated to afford off-white sticky material of compound [55 (A+B)] (0.590 g, 70%), which was directly used for next step. ESIMS: 633 [M$^+$+1]

Step 6: Synthesis of 1011 from 55(A) and 55(B)

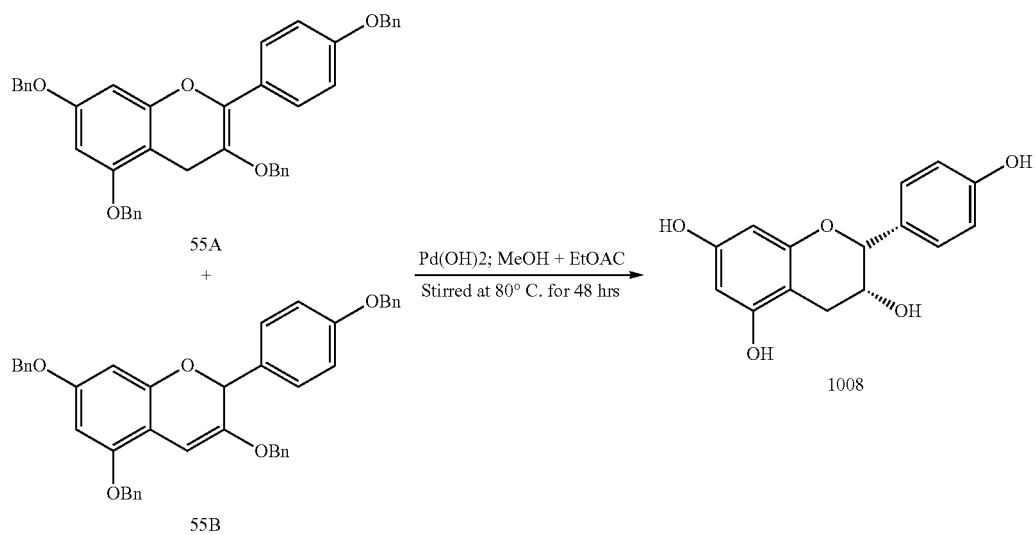

To a stirred solution of 55 (A+B) (0.300 g, 4.7 mmol) in a mixture of ethyl acetate and methanol (1:1, 20 ml), was added a slurry of 10% Pd/C (0.05 g) at mom temperature under nitrogen atmosphere. Hydrogen balloon pressure was applied and the reaction mixture was stirred for 1 hr at RT, followed by additional stirring of overnight at 50° C.-55° C. Reaction was monitored by using TLC. The reaction mass was filtered over celite bed and excess of solvent was removed under vacuum to afford light brown sticky material, which was further purified using silica gel column and 2% methanol in dichloromethane as eluent to afforded cis racemic 1008 (0.040 g, 35%) as an off-white solid. ESIMS: 275 [M$^+$+1]

Example 19

Synthesis of Cis (±) 2-(3-hydroxyphenyl)chroman-3,5,7-triol [1014] was carried out by procedure as described for 1008 with [51] and 3-(benzyloxy)benzaldehyde as starting material.

Example 20

Synthesis of Cis (±) 2-phenylchroman-3,5,7-triol [1015] was carried out by procedure as described for 1008 with [51] and benzaldehyde as starting material.

Example 21

Synthesis of Cis (±) 2-(3,4-dihydroxy-2-methylphenyl)chroman-3,5,7-triol [1035]

Step 1: Synthesis of 51 from 50

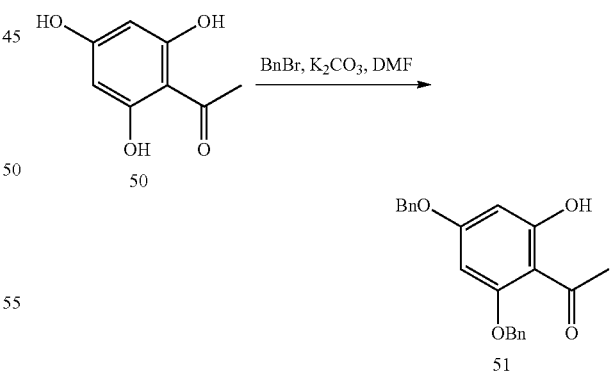

To a stirred solution of [50] (5.0 g, 26.8 mmol) in DMF (50 ml) was added K$_2$CO$_3$ (11.1 g, 80.6 mmol) at 0° C. under nitrogen atmosphere. After stirring at this temperature for 15 min, was added Benzyl bromide drop-wise (6.42 ml, 53.7 mmol). The temperature of reaction mixture was allowed to rise to room temperature and stirred it for overnight. TLC showed complete consumption of [50]. Reaction mixture was quenched with water (500 ml) and extracted with ethyl acetate (2×400 ml). The combined organic layer was washed with water, brine and dried over sodium sulphate. The organic layer was rotary evaporated to afford light brown solid. This crude product was loaded on to silica gel column and elated with 10% ethyl acetate/hexane to off-white powder [51] (3.3 g, 35%). This pure product [51] was used for further step. ESIMS: 348 [M$^+$+1]

Step 2: Synthesis of [53] from [51] and [56]

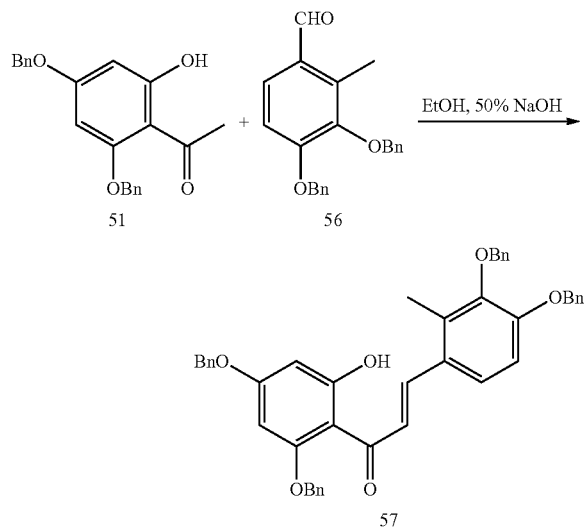

To a stirred solution of [51] (3.3. g, 9.48 mmol) in EtOH (35.0 ml) was added [56] (3.6 g, 11.3 mmol) and reaction mixture was heated to 50° C., then 50% aq.NaOH solution (10.0 ml) was added dropwise with constant stirring to reaction mixture at 50° C. and allowed to stir at room temperature for overnight. Completion of reaction was monitored TLC. TLC showed complete consumption of [56]. Reaction mixture was poured into crushed ice and neutralized with 5% HCl solution, crude product was obtained as yellow precipitate which was filtered through Buchner funnel and crude product was recrystallised with aq.EtOH to obtained pure product [57] as a yellow powder. This pure product [57] (4.2 g, 68%) was used for further step. ESIMS: 663 [M$^+$+1]

Step 3: Synthesis of [58] from [57]

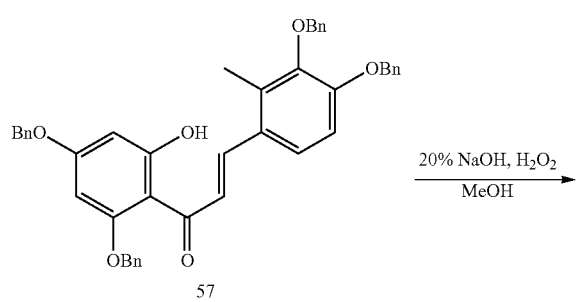

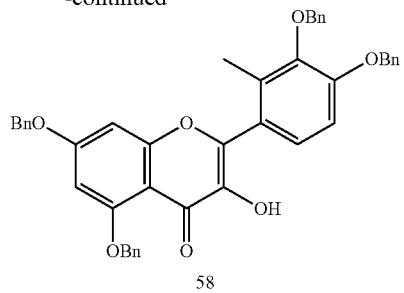

To a stirred solution of [57] (3.0 g, 5.33 mmol) in methanol (35 ml), was added 20% aq. NaOH (5.0 ml). The reaction mixture was kept in an ice bath at 0° C. and 30% H$_2$O$_2$ (2.5 ml) was added dropwise with constant stirring then reaction temperature was raised to rt and stirred at this temperature for overnight. Completion of reaction was monitored by checking TLC. Reaction mixture was acidified with cold 5% HCl solution. The yellow precipitate formed was filtered off through Buchner funnel and crude product was re-crystallised with aq.EtOH to obtained pore product [58] as a yellow powder. This pure product [58] (0.4 g, 10%) was used for further step. ESIMS: 677 [M$^+$+1]

Step 4: Synthesis of [59] from [58]

To a stirred solution of [58] (0.4 g, 0.59 mmol) in DMF was added K$_2$CO$_2$ (0.12 g, 0.86 mmol) at 0° C. under nitrogen atmosphere. After stirring at this temperature for 15 min, was added Benzyl, bromide drop-wise (0.10 ml, 0.88 mmol). The temperature of reaction mixture was allowed to raise to room temperature and stirred it for overnight. TLC showed complete consumption of [58]. Reaction mixture was quenched with water (500 ml) and extracted with ethyl acetate (2×200 ml). The combined organic layer was washed with water, brine and dried over sodium sulphate. The organic layer was rotary evaporated to afford a yellow solid. This crude product was washed with diethyl ether to afford light yellow powder [59] (0.4 g, 88%). ESIMS: 767 [M$^+$+1]

69

Step 5: Synthesis of [60] and [61] from [59]

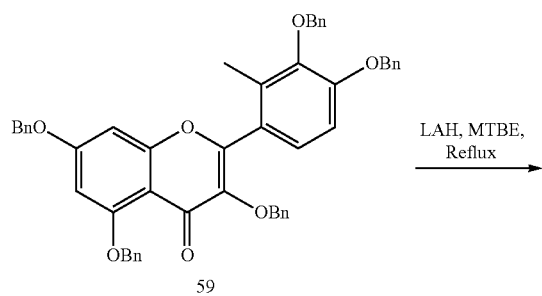

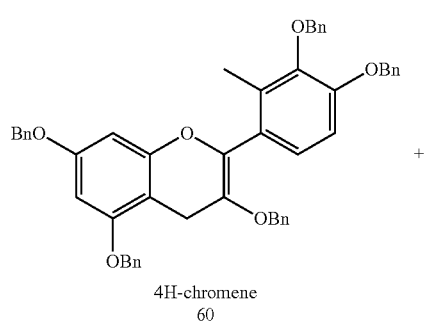

4H-chromene
60

+

70

-continued

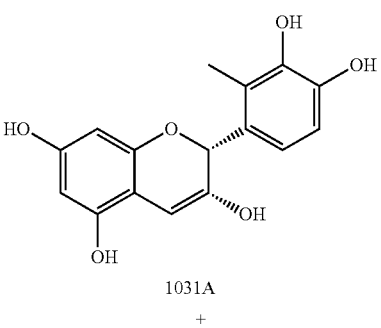

2H-chromene
61

To a stirred solution of (0.4 g, 0.52 mmol) in MTBE (10 ml) was added LAH (0.05 g, 1.50 mmol) at 40° C. under nitrogen atmosphere. After stirring at this temperature for 5 min, the temperature of reaction mixture was allowed to raise to 80° C. for 2 h. Completion of reaction was monitored by checking TLC showed complete consumption of [59]. Reaction mixture was quenched with water (50 ml) and extracted with ethyl acetate (2×100 ml). The combined organic layer was washed with water, brine and dried over sodium sulphate. The organic layer was rotary evaporated to afford dark brown sticky material. This crude product was loaded on to silica gel column and elated with 100% DCM to afford light brown sticky material as a mixture of [60] and [61] (0.25 g, 67%). The mixture of [60] and [61] was used for further step. ESIMS: 727 [M$^+$+1]

Step 6: Synthesis of 1031 from [60] and [61]

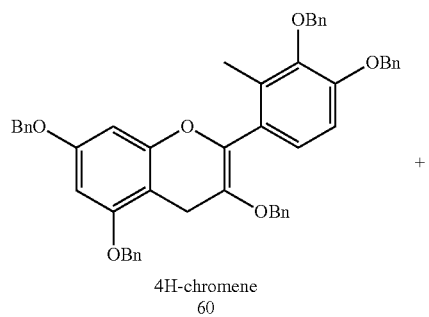

4H-chromene
60

+

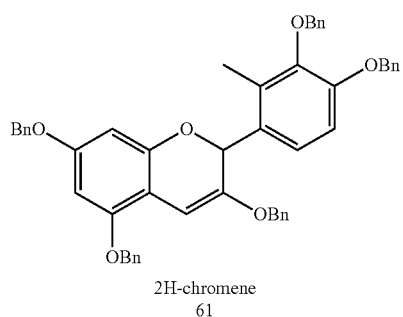

2H-chromene
61

→ 10% Pd/C, MeOH; EtOAc, H$_2$ →

1031A

+

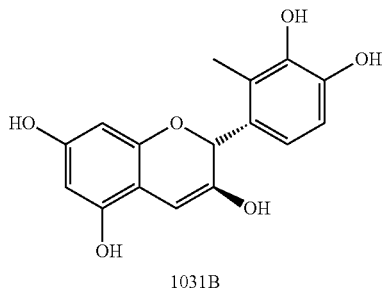
1031B

To a stirred solution of [60] and [61] (0.25 g, 0.34 mmol) in 1:1 mixture ethyl acetate and methanol (10 ml), was added a slurry of 10% Pd/C (0.03 g) at room temperature under nitrogen atmosphere. Hydrogen balloon pressure was applied and the reaction mixture was stirred at this temperature for 1 hr and then reaction temperature was raised to 50° C.-55° C. and stirred at this temperature for overnight. The reaction mass was filtered over celite and the solvent was removed under rotary evaporator to afford light brown sticky material. This crude product was purified by prep HPLC to afford cis racemic [1031A] as a off-white powder (0.02 g, 20%) and trans racemic [1031B] as a off white powder (0.01 g, 9%).

Example 22

Synthesis of Cis (±) 2-(2-fluoro-3,4-dihydroxyphenyl)chroman-3,5,7-triol [1032] was carried out by procedure as described for 1031 with [51] and 3,4-bis(benzyloxy)-2-fluorobenzaldehyde as starting material. ESIMS: 309 [M$^+$+1]

Example 23

Synthesis of Cis (±) 2-(2-fluoro-4,5-dihydroxyphenyl)chromane-3,5,7-triol [1033] was carried out by procedure as described for 1031 with [51] and 4,5-bis(benzyloxy)-2-fluorobenzaldehyde as starting material. ESIMS: 309 [M$^+$+1]

Example 24

Synthesis of Cis (±) 2-(3-fluoro-4-hydroxyphenyl)chromane-3,5,7-triol [1034]

Step 1: Synthesis of [63] from [51] and [62]

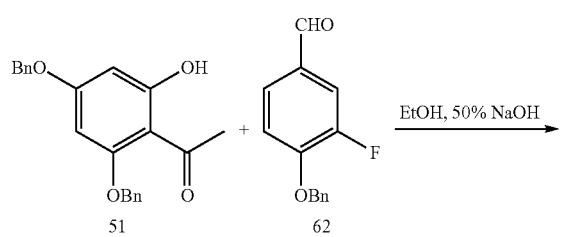

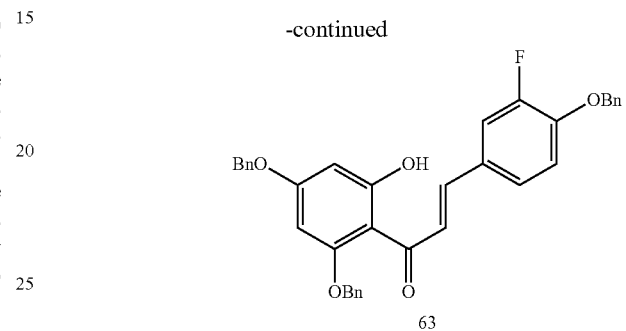
63

To a stirred solution of [51] (2.2 g, 6.32 mmol) in EtOH (35.0 ml) was added [62] (1.7 g, 7.58 mmol) and reaction mixture was heated to 50° C., then 50% aq.NaOH solution (10.0 ml) was added dropwise with constant stirring to reaction mixture at 50° C. and allowed to stir at room temperature for overnight. Completion of reaction was monitored TLC. TLC showed complete consumption of [62]. Reaction mixture was poured into crushed ice and neutralized with 5% HCl solution, crude product was obtained as yellow precipitate which was filtered through Buchner funnel and crude product was recrystallised with aq.EtOH to obtained pure product [63] as a yellow powder. This pure product [63] (2.0 g, 55%) was used for further step. ESIMS: 560 [M$^+$1]

Step 2: Synthesis of [64] from [63]

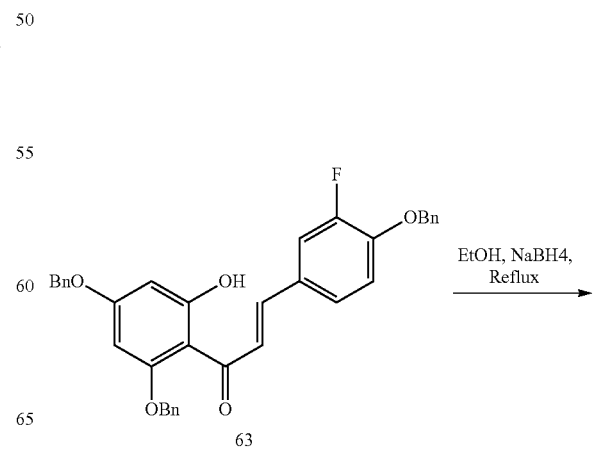
63

-continued

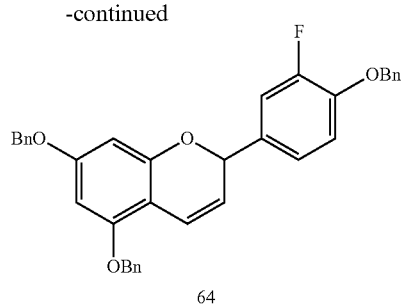
64

To a stirred solution of [63] (2.0 g, 3.57 mmol) in mixture of EtOH (20.0 ml) and THF (10 ml) was added NaBH$_4$ (0.3 g, 7.14 mmol) and reaction mixture was heated to 80° C. for 2 hr, then the reaction mixture was rotary-evaporated to dryness and was added 1:2 mixture of AcOH and water (20 ml) at 0° C. The reaction mixture was allowed to stir at room temperature for overnight. Reaction mixture was again rotary evaporated to dryness and saturated solution of Na$_2$CO$_3$ was poured and was extracted with DCM (200 ml). The combined organic layer was washed with water, brine and dried over sodium sulphate. The organic layer was rotary evaporated to afford light brown sticky material. This crude product was loaded on to silica gel flash column and eluted with 100% DCM to afford light yellow sticky material [64] (1.0 g, 51%). ESIMS: 545 [M$^+$+1]

Step 3: Synthesis of [65] from [64]

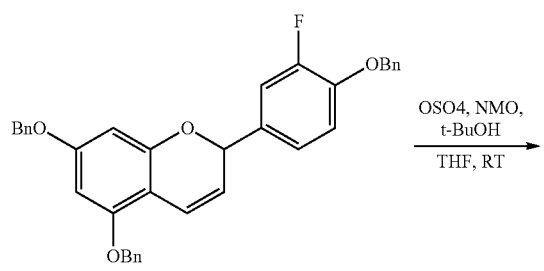

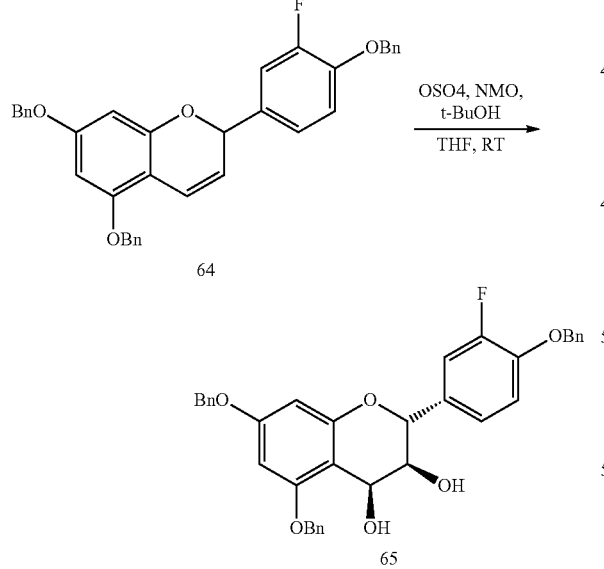

To a stirred solution of [64] (1.0 g, 1.8 mmol) in dry THF was added N-methyl morpholine oxide (0.2 g, 2.29 mmol), OsO$_4$ in t-BuOH (3%, 2 ml) and water (3 ml) at room temperature and the resulting solution was stirred at this temperature for 6 h. Reaction was monitored by TLC. After complete consumption of [64], saturated solution of sodium thiosulfate was added and extracted with DCM. The combined organic layer was washed with brine and dried over sodium sulphate and evaporated to afford the desired material [65] (0.9 g, 86%) which was used as such for further reaction. ESIMS: 579 [M$^+$+1]

Step 4: Synthesis of [66] from [65]

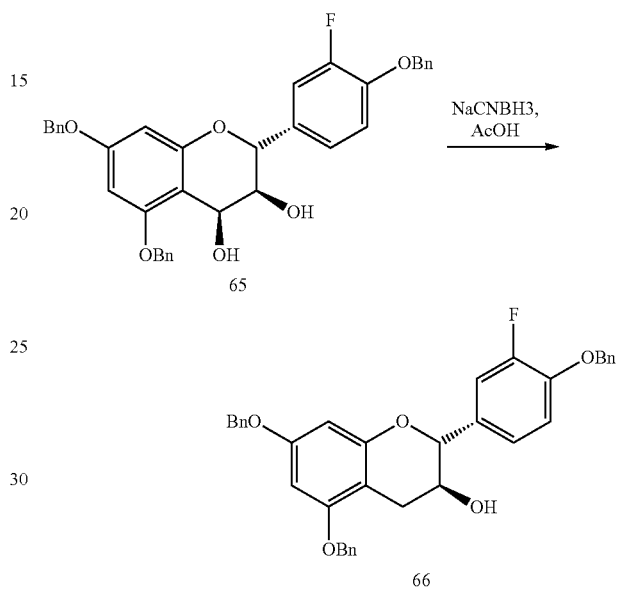

To a stirred solution of [65] (0.9 g, 1.55 mmol) in AcOH at 0° C. was added NaCNBH$_3$ (1.4 g 23.3 mmol) portion-wise under constant stirring. The resulting solution was stirred at 0° C. for 1 h and then the temperature of reaction, mixture was allowed to come to room temperature. Reaction was monitored by TLC. After complete consumption of [65], saturated NaHCO$_3$ was added and extracted with DCM. The combined organic layer was washed with brine and dried over sodium sulphate and evaporated to afford the desired material trans [66] (0.60 g, 68%) which was used, as such for further reaction. ESIMS: 563 [M$^+$+1]

Step 5: Synthesis of [67] from [66]

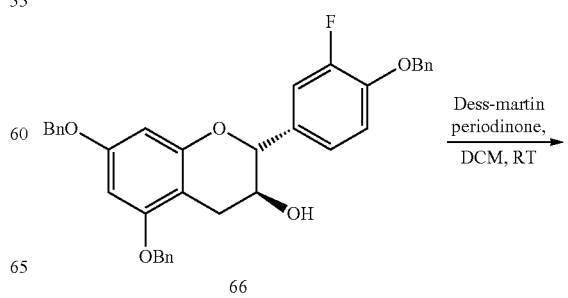

-continued

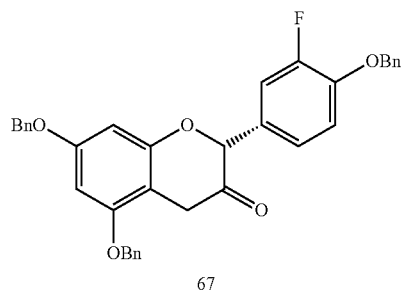
67

To a stirred solution of [66] (0.6 g, 1.0 mmol) in Dry DCM, Dess-Martin Periodinane (1.2 g, 3.0 mmol) was added in one portion at room temperature. After an additional stirring for 6-7 h, saturated NaHCO$_3$ (20 ml) was added and was extracted with DCM (3×100 ml). The combined organic layers were washed with water and dried over sodium sulphate. The organic layer was concentrated to afford light pink sticky material which was further purified using silica gel flash column chromatography using DCM as eluent to afford off [67] as a white-pinkish solid powder (0.40 g, 71%) ESIMS: 561 [M$^+$+1]

Step 6: Synthesis of [68] from [67]

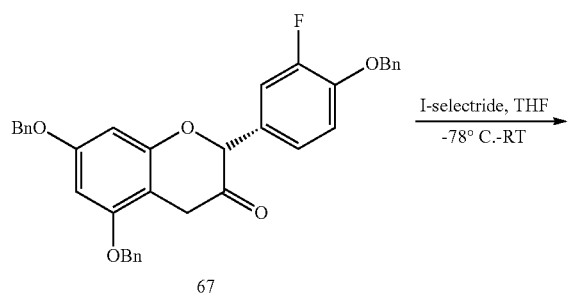

To a stirred solution of [67] (0.2 g, 0.35 mmol) in dry THF at −78° C. was added L-selectride (1.78 ml) drop wise under nitrogen atmosphere. The resulting solution was stirred at −78° C. for 5 h and then the temperature of reaction mixture was allowed to come to room temperature. Reaction was monitored by TLC. After complete consumption of [67], saturated NaHCO$_3$ was added and extracted with ethyl acetate. The combined organic layer was washed with brine and dried over sodium sulphate and evaporated to afford the desired material cis [68] (0.10 g, 51%). ESIMS: 563 [M$^+$+1]

Step 7: Synthesis of [1034] from [68]

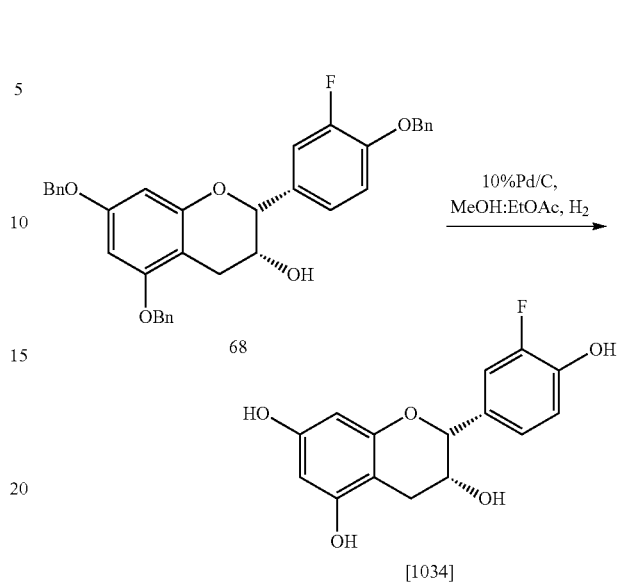

To a stirred solution of [68] (0.10 g, 0.17 mmol) in 1:1 mixture ethyl acetate and methanol (10 ml), was added a slurry of 10% Pd/C (0.010 g) at room temperature. Hydrogen balloon pressure was applied and the reaction mixture was stirred at this temperature for 1 hr and then reaction temperature was raised to 50° C.-55° C. and stirred at this temperature for overnight. The reaction mass was filtered over celite and the solvent was removed under rotary evaporator to afford light brown sticky material. This crude product was loaded on to silica gel column and eluted with 4% methanol/Dichloromethane to afford off white powder [1034] (0.028, 57%). ESIMS: 293 [M$^+$1]

Example 25

Synthesis of Cis (±) 2-(2-fluoro-3,4-dihydroxyphenyl)chroman-3,5,7-triol [1035] was carried out by procedure as described for 1031 with [51] and 3,4-bis(benzyloxy)-5-methylbenzaldehyde as starting material. ESIMS: 305 [M$^+$+1]

Example 26

Synthesis of (2R,3R)-2-(3,4-dihydroxyphenyl)chromane-4,4-d2-3,5,7-triol [1036]

Step 1: Synthesis of [84 and 85] from [86]

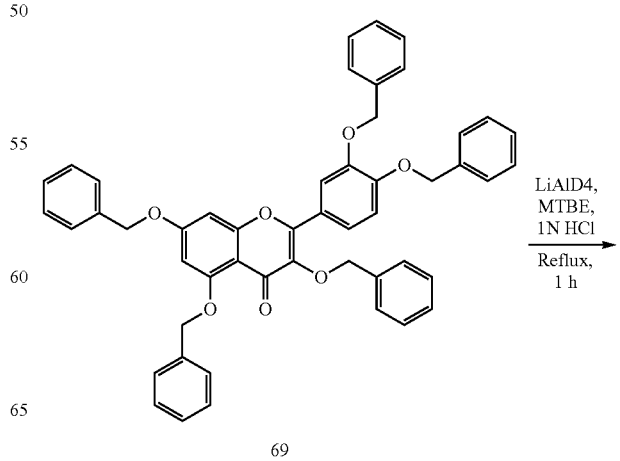

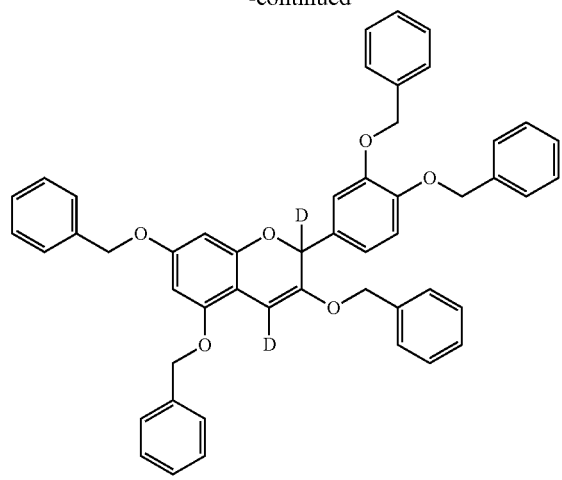

70

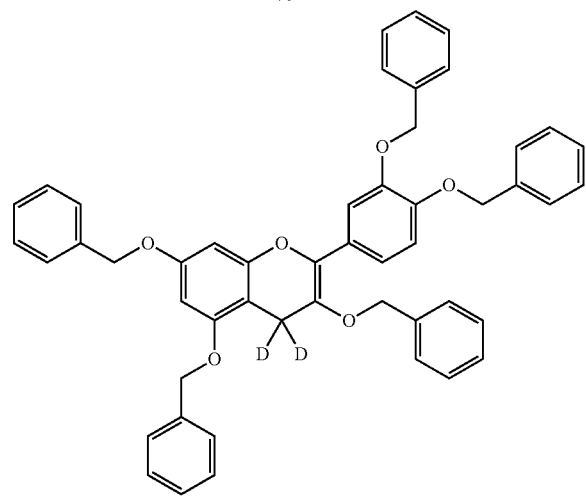

71

To a stirred suspension of [69] (2.5 g) in methyl tertiary butyl ether (75.0 mL, 30 vol) was added lithium aluminium deuteride (0.251 mg, 3.6 eq) in small portions at room temperature under a nitrogen atmosphere. After stirring for 10 min at this temperature, the temperature of the reaction was raised from 65° C. to 70° C. After stirring at the same temperature for 1 hour, reaction mass was quenched with a 1 N HCl (10 ml) solution at 0 to −5° C., then the temperature of the reaction was raised to room temperature. Ethyl acetate (10 ml) was added to the reaction and stirred for 30 min. The organic layer was decanted and removed. Ethyl acetate was added to the aqueous layer. The mixture was filtered through a celite bed, and the aqueous and organic layer was separated. The organic layers were combined and concentrated under reduced pressure to afford art off-white solid (2.5 g). The crude compound was triturated with ethyl acetate (10 ml) at room temperature for 4 h, then filtered, washed with ethyl acetate, and dried under vacuum to afford an off-white solid. (1.0 g, 40% yield) [70].

After isolation of [70], the mother liquor was concentrated under reduced pressure to afford a pale yellow residue. The semi solid obtained was triturated with 50% ethyl acetate:hexane (250 ml) for 30 min at room temperature, thus solid was obtained. The solid was filtered and washed with 50% ethyl acetate:hexane (200 ml). The solid obtained was dried under vacuum to obtain off white solid (0.250 g, 10% yield) [71]. ESIMS: 741 [M$^+$+1]

Step 2: Synthesis of [1036] from [71]

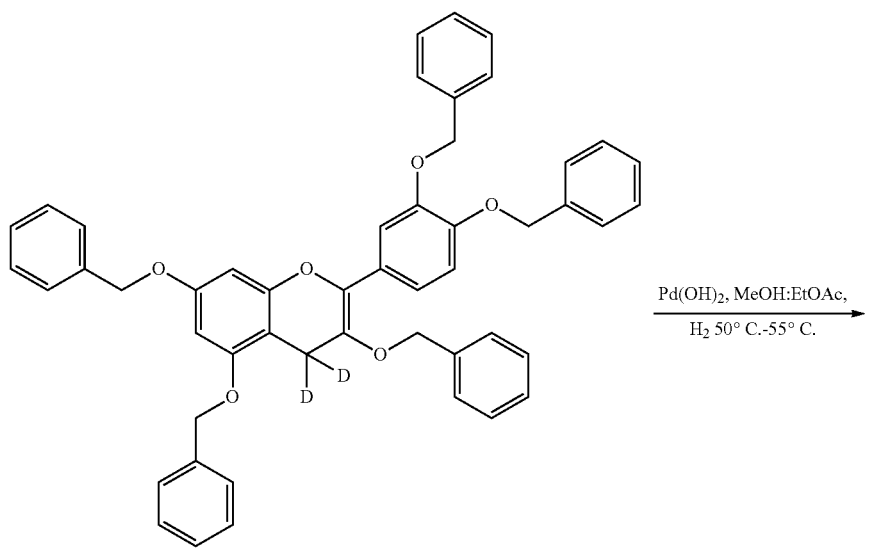

71

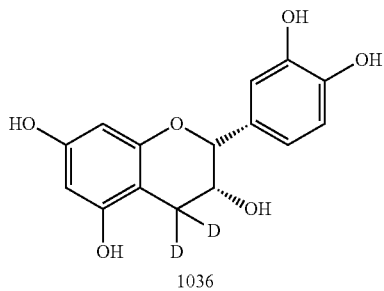

1036

To a stirred solution of [71] (0.3 g, 0.404 mmol) in 1:1 mixture ethyl acetate and methanol (10 ml), was added a slurry of Pd(OH)$_2$ (0.030 g) at room temperature. The reaction mixture was stirred, at room temperature for 1 h then the reaction temperature was raised to 50 to 55° C. and stirred at this temperature for overnight. The reaction was filtered through celite. The collected solvent was removed with a rotary evaporator to afford a light brown sticky material. This crude product was loaded on to silica gel column and elated with a 4% methanol/dichloromethane to afford a light pink powder (0.055 g, 46% yield) [1036]. ESIMS: 293 [M$^+$+1]

To a stirred solution of [70] (0.18 g, 0.24 mmol) in a 1:1 mixture of ethyl acetate and methanol (8 ml), was added a slurry of Pd(OH)$_2$ (0.020 g) at room temperature. The reaction mixture was stirred at this temperature for 1 h and then the reaction temperature was raised to 50-55° C. and stirred at this temperature for overnight. The reaction was filtered through celite. The collected solvent was removed with a rotary evaporator to afford a light brown sticky material. This crude product was loaded on to silica gel column and elated with 4% methanol/dichloromethane to afford an off while powder, which was then separated on prep-HPLC to afford [1038] (0.045 g, 64% yield). ESIMS: 293 [M$^+$+1]

Step 3: [1038] from [70]

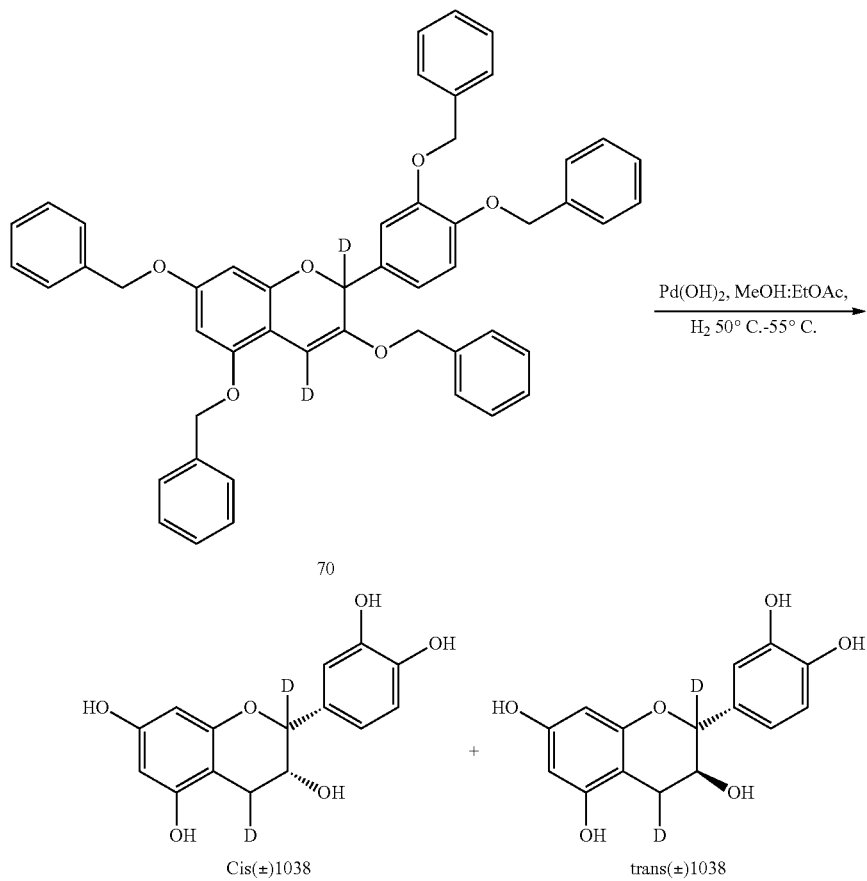

Example 27
Synthesis of (2R,3R)-2-(3,4-dihydroxyphenyl)chromane-2-d-3,5,7-triol [1037]
Step 1: Synthesis of [73 and 74] from [72]
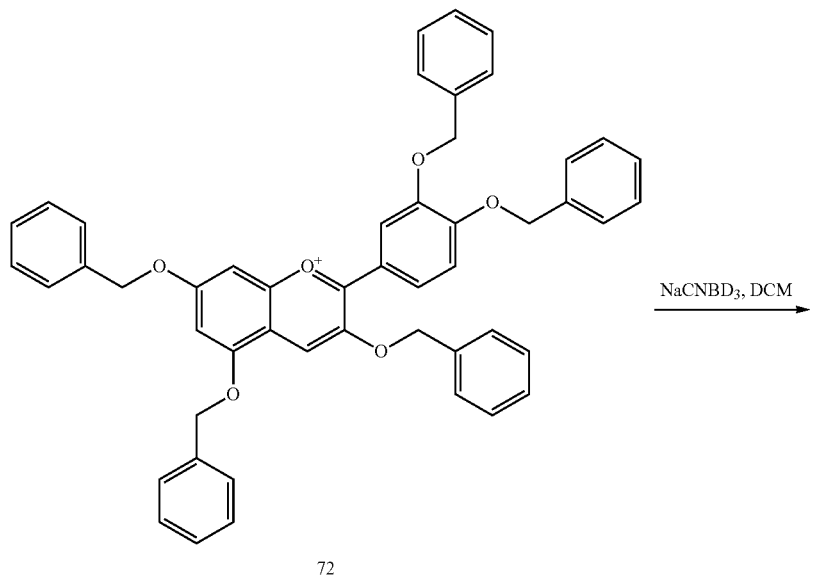
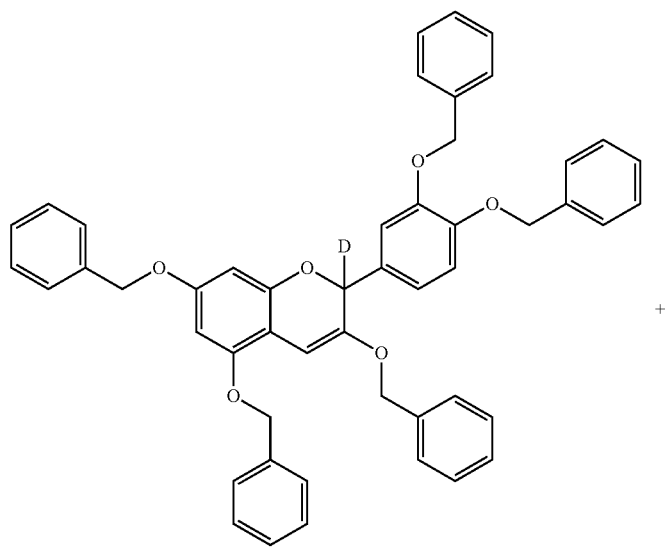

-continued

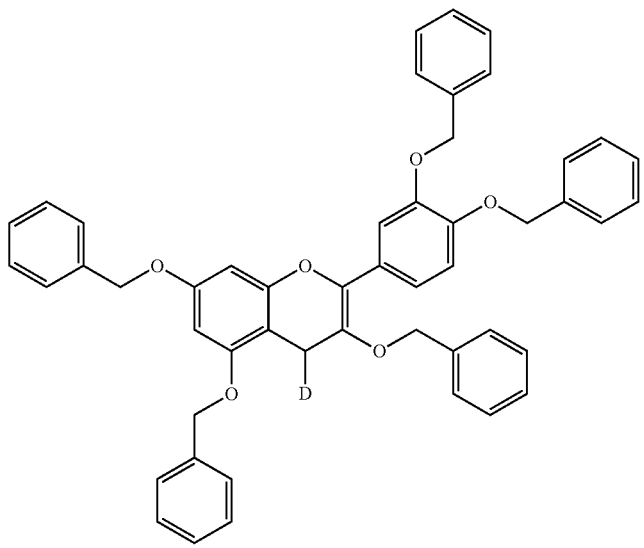
74

To a stirred solution of [72] (0.2 g, 0.25 mmol) in dry dichloromethane under nitrogen atmosphere was added NaCNBD$_3$ (0.02 g, 0.25 mmol) in one portion at room temperature. Reaction mixture was allowed to stir at this temperature for 15 min. After completion of reaction, the reaction mixture was quenched with water under cooling. Reaction mixture was further diluted with dichloromethane, organic layer was separated, dried over sodium sulfate and evaporated under reduced pressure to give [73] and [74] as light pink sticky material (0.16 g, 85%). ESIMS: 740 [M$^+$1]

Step 2: Synthesis of [1037] from [73]

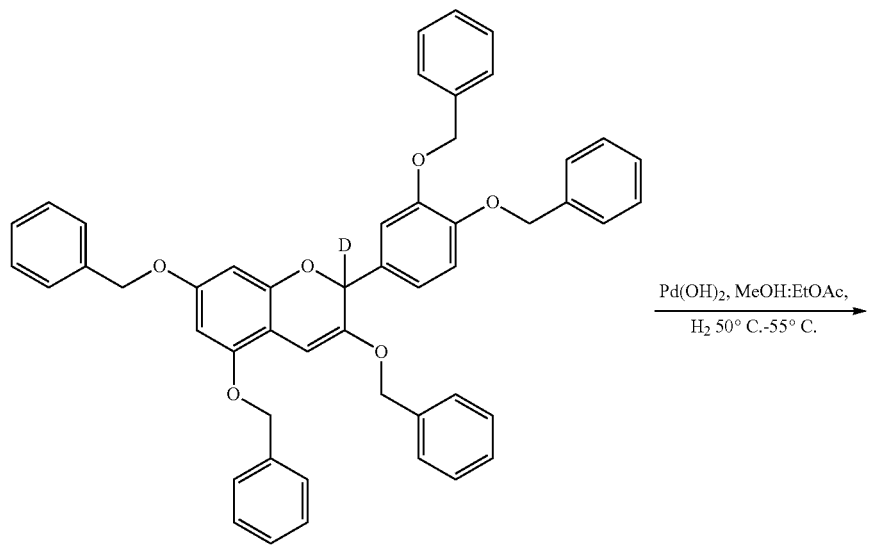
73

Pd(OH)$_2$, MeOH:EtOAc,
H$_2$ 50° C.-55° C.

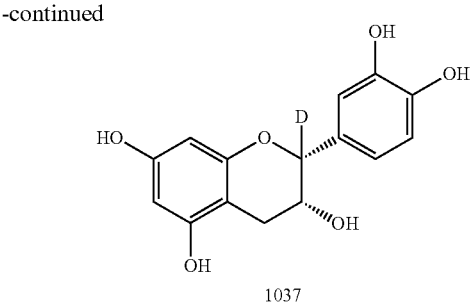

1037

To a stirred solution of [73] (0.150 g, 0.20 mmol) in a 1:1 mixture of ethyl acetate and methanol (8 ml), was added a slurry of Pd(OH)$_2$ (0.020 g) at room temperature. Hydrogen balloon pressure was applied and the reaction mixture was stirred at this temperature for 1 h and then the reaction temperature was raised to 50-55° C. and stirred at this temperature for overnight. The reaction was filtered through celite. The collected solvent was removed with a rotary evaporator to afford a light brown sticky material. This crude product was loaded on to silica gel column and elated with 4% methanol/dichloromethane to afford an off white powder, which was then separated on prep-HPLC to afford cis racemic [1037] along with minor trans isomer. ESIMS: 292 [M$^+$+1]

Example 28

Synthesis of dibenzyl (4-(3,5,7-trihydroxychroman-2-yl)-1,2-phenylene)bis(carbonate) [1048]

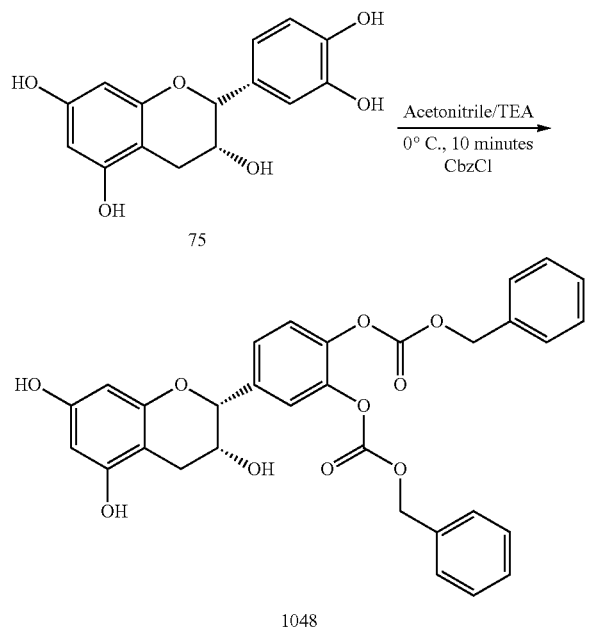

To a suspension of [75] (1.0 eq, 0.15 gm, 0.5 mmol) in 10 ml acetonitrile at 0° C. was added dropwise methyl amine (2.0 eq, 0.14 ml, 1.0 mol) and stirred for 10 minutes. To this suspension benzyl chloroformate (2.0 eq, 0.16 ml, 1.0 mol) was added dropwise over a period of 5 minutes. The resulting solution was stirred at 0° C. for another 10 minutes. The progress of the reaction, was monitored by TLC. The reaction mixture was diluted with ethyl acetate and washed with water. Ethyl acetate layer was separated and dried over Na$_2$SO$_4$, filtered and evaporated to yield colorless gel which was subjected to column chromatography on silica gel and elated with 2% MeOH/Dichloromethane to afforded [1048] as a colorless solid [0.135 gm, 46%]. ESIMS: 740 [M$^+$+1]

In a similar manner the compounds [1043], [1044] and [1049] were synthesized.

Example 29

Synthesis of 4-(3,5,7-trihydroxychroman-2-yl)-1,2-phenylene bis(benzylcarbamate) [1059]

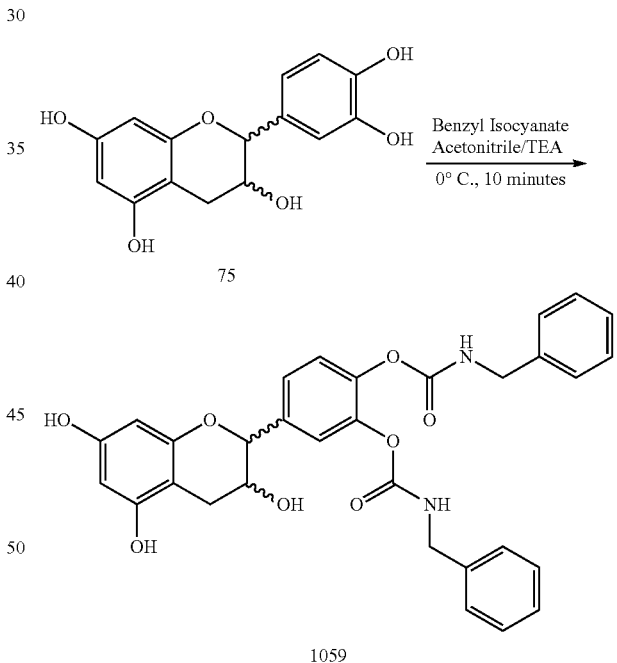

To a suspension of [75] (1.0 eq, 0.2 gm, 0.68 mmol) in 10 ml acetonitrile at 0° C. was added dropwise triethyl amine (2.0 eq, 0.14 ml, 1.4 mol) and stirred for 10 minutes. To this suspension benzyl isocyanate [2.0 eq. 0.17 ml, 1.4 mol] was added dropwise over a period of 5 minutes. The resulting solution was stirred at 0° C. for 10 minutes. The progress of the reaction was monitored by TLC. The reaction mixture was diluted with ethyl acetate and washed with water. Ethyl acetate layer was separated and dried over Na$_2$SO$_4$, filtered and evaporated to yield colorless gel which was subjected to column chromatography on silica gel [100-200 mesh size]

and eluted the compound by 2% MeOH/Dichloromethane to afforded [1059] as a colorless solid [0.08 g, 20%]. ESIMS: 556 [M+ +1]

Example 30

Synthesis of (2R,3R)-2-(3,4-dihydroxyphenyl)-5,7-dihydroxychroman-3-yl isopropylcarbamate [1046]

Step 1: Synthesis of Tetrabenzylated Racemic Epicatechin [76] Form Racemic Epicatechin [75]

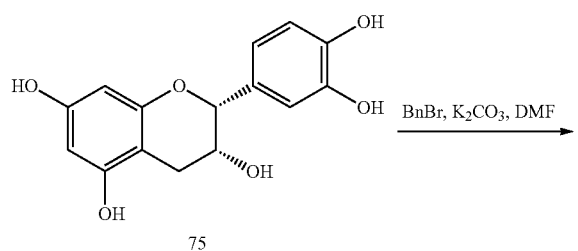

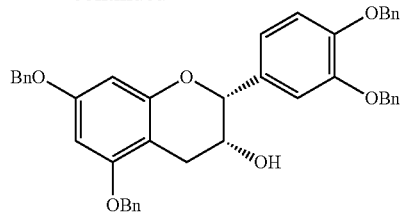

To a stirred of [75] (1.0 gm, 3.4 mmol) in DMF was added K₂CO₃ (2.3 gm, 17.0 mmol) at 0° C. under nitrogen atmosphere. After stirring at this temperature for 15 min, was added Benzyl bromide drop-wise. The temperature of reaction mixture was allowed to raise to room temperature and stirred it for overnight. TLC showed complete consumption of [75]. Reaction mixture was quenched with water (50 ml) and extracted with ethyl acetate (2×100 ml). The combined organic layer was washed with water, brine and dried over sodium sulphate. The organic layer was rotary evaporated to afford to afford light brown sticky material. This crude product was loaded on to silica gel column and eluted with 8% ethyl acetate/hexane to afford white powder [76] (1.5 gm, 68%). ESIMS: 651 [M+ +1]

Step 2: Synthesis of [77] from [76]

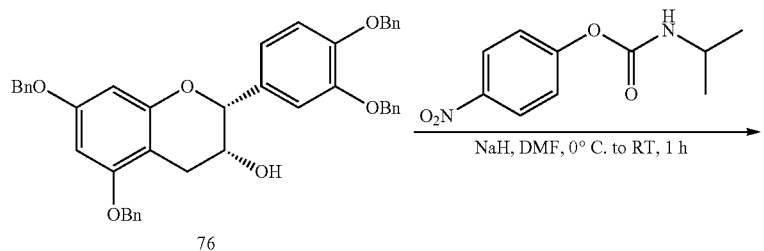

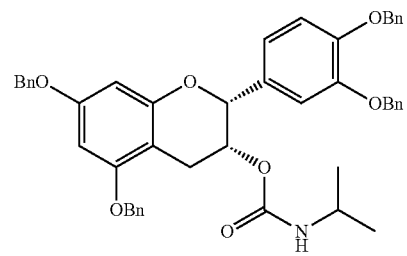

To a stirred of [76] (0.20 gm, 0.30 mmol) in DMF was added NaH portionwise (0.017 gm, 0.46 mmol) at 0° C. under nitrogen atmosphere. After stirring at this temperature for 1 h, was added 4-nitrophenyl isopropylcarbamate (0.10 gm, 0.46 mmol) portion-wise. The temperature of reaction mixture was allowed to raise to room temperature and stirred it for 2 h. TLC showed complete consumption of [76] Reaction mixture was quenched with water (50 ml) and extracted with ethyl acetate (2×100 ml). The combined organic layer was washed with water, brine and dried over sodium sulphate. The organic layer was rotary evaporated to afford to afford light brown sticky material which was purified on silica gel column with 8% EtOAc/hexane as eluent to afford [77] (0.07 gm, 35%) as light yellow powder. ESIMS: 736 [M$^+$+1]

Step 3: Synthesis of [1046] from [77]

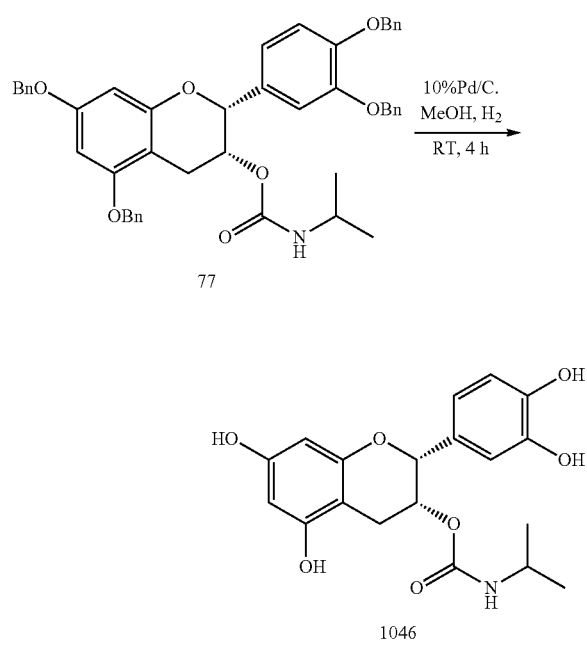

To a stirred solution of (0.070 g, 0.09 mmol) in 1:1 mixture ethyl acetate and methanol (10 ml), was added a slurry of 10% Pd/C (0.070 g) at room temperature. Hydrogen balloon pressure was applied and the reaction mixture was stirred at this temperature for 4 hr. The reaction mass was filtered over celite and the solvent was removed under rotary evaporator to afford light brown sticky material. This crude product was purified on silica gel column with 4% MeOH/Dichloromethane as eluent to afford [1046] (0.02 g, 10%) as a off white powder (0.005 g, 74%), ESIMS: 376 [M$^+$+1]

In a similar manner the compounds [1045], [1047], [1053], [1055] and [1056] were synthesized.

Example 31

Synthesis of dibenzyl (4-((2R,3R)-5,7-bis(((benzyloxy)carbonyl)oxy)-3-hydroxychroman-2-yl)-1,2-phenylene) bis(carbonate) [1052]

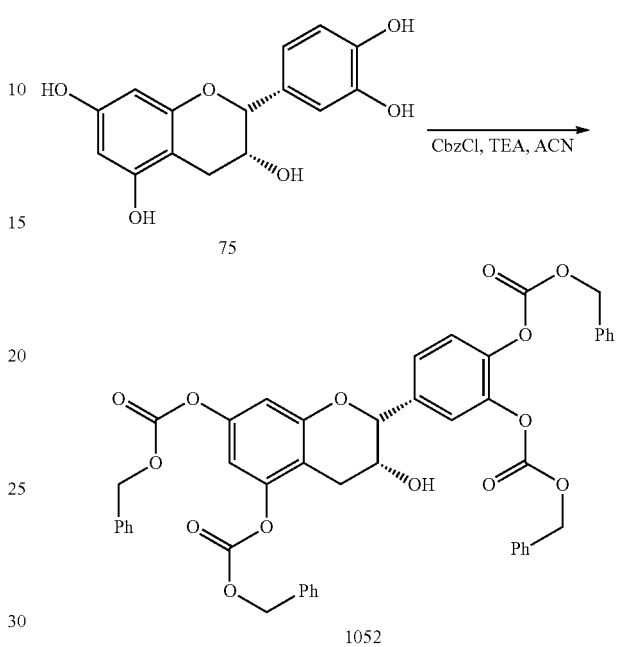

To a suspension of [75] (1.0 eq, 1.0 gm, 3.5 mmol) in 10 ml acetonitrile at 0° C. was added dropwise triethyl amine (2.9 ml, 21.0 mol) and stirred for 10 minutes. To this suspension benzyl chloroformate (3.61 ml, 21.0 mmol) was added dropwise over a period of 5 minutes. The resulting solution was stirred at 0° C. for another 10 minutes. The progress of the reaction was monitored by TLC. The reaction mixture was diluted with ethyl acetate and washed with water. Ethyl acetate layer was separated and dried over Na$_2$SO$_4$, filtered and evaporated to afford [1052] transparent sticky material (2.70 g, 94%]. ESIMS: 827 [M$^+$1]

In a similar manner [1051] was synthesized.

Example 32

Synthesis of dibenzyl (4-((2R,3R)-5,7-bis(((benzyloxy)carbonyl)oxy)-3-hydroxychroman-2-yl)-1,2-phenylene) bis(carbonate) [1066]

Step 1: Synthesis of [1066] from [1048]

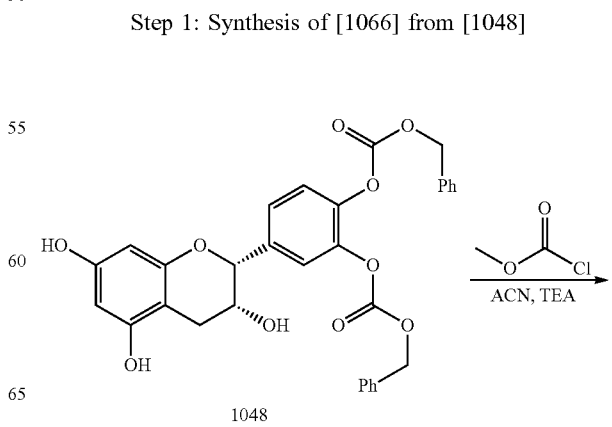

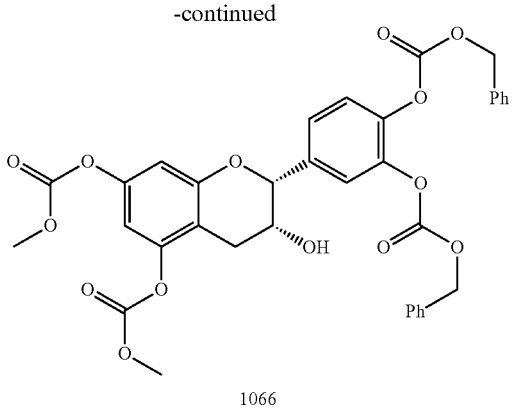

1066

To a suspension of [1048] (0.1 gm, 0.17 mmol) in 10 ml acetonitrile at 0° C. was added dropwise to triethyl amine (0.02 ml, 0.17 mmol) and stirred for 10 minutes. To this suspension methyl chloroformate (0.01 ml, 0.17 mmol) was added dropwise over a period of 5 minutes. The resulting solution was stirred at 0° C. for another 30 minutes. The progress of the reaction was monitored by TLC. The reaction mixture was diluted with ethyl acetate and washed with water. Ethyl acetate layer was separated and dried over $Na_2SO_4$, filtered and evaporated to yield colorless gel which was subjected to column chromatography on silica gel and eluted with 20% Ethylacetate/Hexane to afforded [1066] as a off white solid. [0.04 gm, 35%]. ESIMS: 675 [$M^+$+1]

In a similar manner [1060] was synthesized

Step 2: Synthesis of [1058] from [1066]

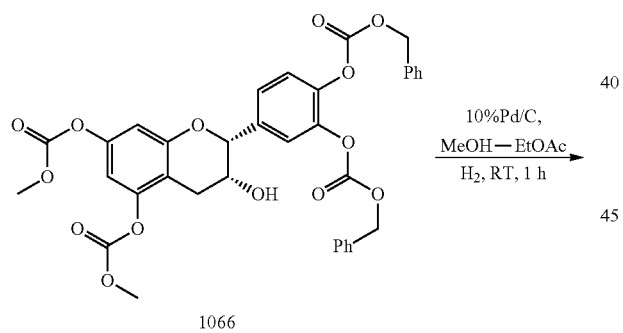

1066

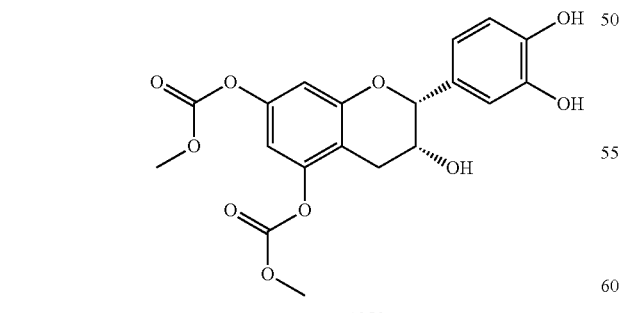

1058

To a stirred solution of [1066] (0.10 g, 0.14 mmol) in 1:1 mixture ethyl acetate and methanol (10 ml), was added a slurry of 1.0% Pd/C (0.01 g) at room temperature. Hydrogen balloon pressure was applied and the reaction, mixture was stirred at this temperature for 1 hr. The reaction mass was filtered over celite and the solvent was removed under rotary evaporator to afford light brown sticky material. This crude product was purified on silica gel column with 4% MeOH/Dichloromethane as eluent to afford [1058] (0.05 g, 83%) as a light brown powder (0.05 g, 74%). ESIMS: 407 [$M^+$+1]

In a similar manner [1050], [1054] and [1057] were synthesized.

Example 33

Synthesis of [1061], [1062] and [1063]

Step 1: Synthesis of [78], [79] and [80] from [1048]

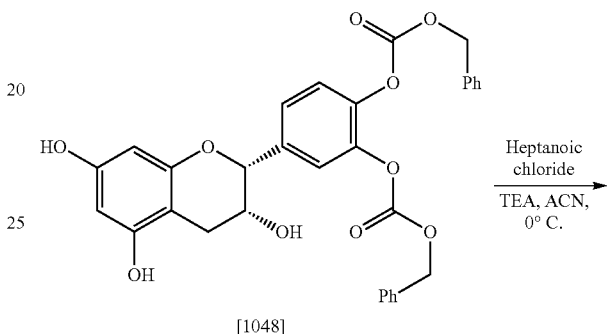

[1048]

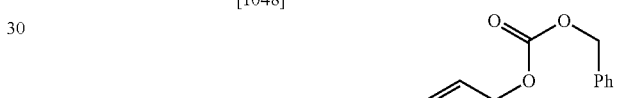

[78]

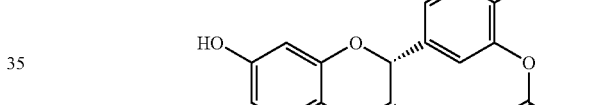

[79]

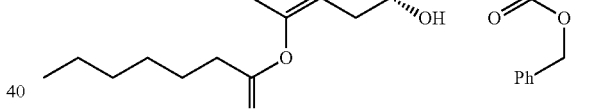

[80]

To a suspension of [1048] (0.5 gm, 0.89 mmol) in 20 ml acetonitrile at 0° C. was added dropwise triethyl amine (0.12 ml, 0.89 mmol) and stirred for 1.0 minutes. To this suspension hepatnoic chloride (0.13 g, 0.89 mmol) was added dropwise over a period of 5 minutes. The resulting solution was stirred at 0° C. for another 30 minutes. The progress of the reaction was monitored by TLC. The reaction mixture was diluted with ethyl acetate and washed with water. Ethyl acetate layer was separated and dried over $Na_2SO_4$, filtered and evaporated to yield colorless gel which was subjected to column chromatography on silica gel and eluted with 2% MeOH/Dichloromethane to afforded [78] (0.07 g, 11%) as off white solid, [79] (0.05, 9%) and [80] (0.18 g, 25%) as a light green sticky material. [78] and [79]: ESIMS: 671 [M$^+$+1]

[80]: ESIMS: 783 [M$^+$1]

Step 2: Synthesis of [1061], [1062] and [1063] was carried out as described for [1058] from [78], [79] and [80]

In a similar manner [1064] and [1065] were synthesized.

Example 34

Testing of Compounds for Their AMPK Activation Potential

AMPK activation potential of the compounds was evaluated using cell based ELISA. Hepatoma (Hep G2) liver cells were maintained in a T 75 culture flask-containing 25 mM DMEM+10% fetal calf serum. The cells were maintained in a T 75 culture flask-containing medium (DMEM+10% fetal calf serum). On reaching a confluence of 70 to 80%, the cells were seeded in a 96 well plate at a density of 40,000 cells per well in 25 mM DMEM+10% FCS medium. The plates were then incubated at 37° C. with 5% $CO_2$ for 24 hours. Various concentrations of drugs were prepared in DMSO and diluted to required concentration with the medium and incubated at 37° C. with 5% $CO_2$ for 30 min and 1 h for Epicatechin analogs and 11-BHP analogs respectively. Metformin was used as positive control. Cells were fixed with 4% formaldehyde for 30 minutes at room temperature and washed three times with PBS containing 0.1% Triton X-100. Endogenous peroxidase was quenched with 1% $H_2O_2$ in PBS-T (0.1% Tween 20) for 30 minutes and washed three times in PBS-T. Cells were blocked with 1% BSA in PBS-T for 1 hour. The cells were incubated with 1:1000 dilution primary antibody (Phospho-AMPKα (Thr172) Rabbit mAb, Cell Signaling in PBS-T containing 5% BSA at 4° C. overnight. The cells were then washed three times with PBS-T for 5 minutes and incubated with 1:1000 dilution secondary antibody (Anti-rabbit IgG, HRP-linked Antibody, Cell Signaling) in PBS-T with 1% BSA for 1 hour at RT. Cells were washed three times with PBS-T for 5 minutes The cells were incubated with 100 µl TMB substrate solution for 30 minutes and the reaction was stopped with 100 µl of 2N $H_2SO_4$. Then the plate was read at 450 nM using ELISA plate reader and absorbance recorded. % activity was calculated using DMSO control as 100%. All compounds of the present invention, as exemplified and encompassed are found to be active. For illustrative purpose, the activation potential of the compounds at 10 nm concentration is provided in Table 2.

TABLE 2

Activiation potential of the compounds.

| Compound | % pAMPK(at 10 nm) |
|---|---|
| 1002 | 108 |
| 1004 | 114 |
| 1005 | 102 |
| 1006 | 103 |
| 1007 | 113 |
| 1008 | 103 |
| 1009 | 101 |
| 1015 | 119 |
| 1017 | 110 |
| 1018 | 100 |
| 1019 | 101 |
| 1026 | 101 |
| 1027 | 94 |
| 1028 | 101 |
| 1029 | 93 |
| 1030 | 94 |
| 1032 | 104 |
| 1031 | 101 |
| 1033 | 107 |
| 1034 | 107 |
| 1035 | 102 |
| 1036 | 105 |
| 1037 | 110 |
| 1041 | 88 |
| 1042 | 95 |
| 1043 | 98 |
| 1044 | 96 |
| 1045 | 105 |
| 1046 | 101 |
| 1047 | 100 |
| 1048 | 103 |
| 1049 | 105 |
| 1050 | 91 |
| 1051 | 85 |
| 1052 | 103 |
| 1053 | 94 |
| 1054 | 91 |
| 1055 | 105 |
| 1056 | 112 |
| 1058 | 117 |
| 1059 | 144 |
| 1060 | 110 |
| 1064 | 110 |
| 1066 | 139 |
| 1068 | 90 |
| 1069 | 110 |
| 1070 | 126 |
| 1071 | 102 |
| 1072 | 99 |
| 1073 | 109 |

We claim:

1. A process for the preparation of a compound of Formula (I)

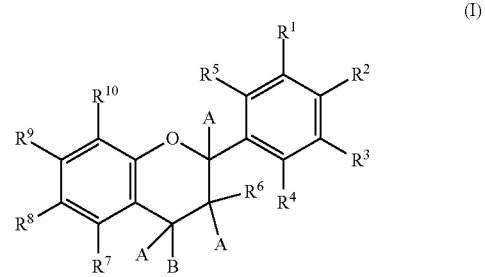

(I)

wherein

A and B are independently deuterium, hydrogen, or alkyl, $R^1$ to $R^{10}$ are independently hydrogen; $NH_2$, Cl, hydroxyl, $C_1$-$C_8$ alkoxy, $C_1$-$C_8$ acyclic or cyclic alkyl, OCO—$OR^{11}$, —O—CO—$R^{11}$, O—CO—$NR^{11}R^{12}$, —O—CO—$R^{13}$, which can be optionally substituted $OR^{11}$, $COOR^{11}$, $R^{11}$ and $R^{12}$ are independently hydrogen, $C_{1-6}$ alkyl, aryl, $C_1$-$C_8$ alkaryl, $C_1$-$C_8$ substituted alkyl, which may be straight, branched chain or cyclic, substituted aryl, or $R^{11}$ and $R^{12}$ taken together with the atoms to which they may attach to form a 5- to 7-member ring optionally incorporating one or two ring heteroatoms selected from the group consisting of N and O, which is optionally substituted with further substituents or A and $R^6$ may form an oxime;

$R^{13}$ is $C_1$-$C_{12}$ alkyl, $C_1$-$C_8$ aryl, $C_1$-$C_{12}$ substituted alkyl, which may be straight, branched chain or cyclic, $C_1$-$C_{12}$ alkoxy which may be straight, branched chain or cyclic;

wherein substitution at C2 and C3 on the pyran ring is always cis, comprising the steps of:

(i) protecting the hydroxyl groups of an acetophenone of Formula 1, wherein X is Me- with a protecting agent in the presence of a base and a solvent;

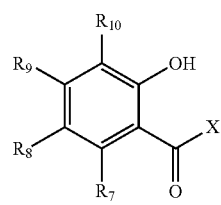

1

(ii) reacting compound of Formula 1 obtained from step (i) with a compound of formula 2 in the presence of a base and a solvent to obtain a chalcone of formula 3;

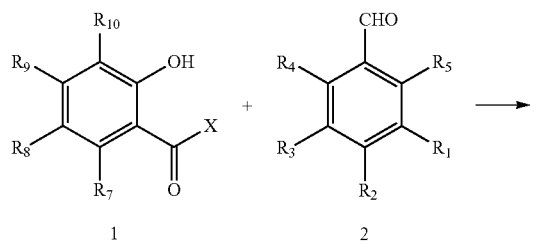

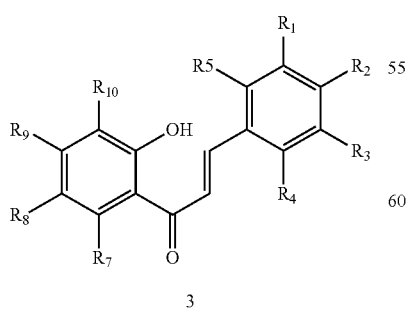

3

(iii) converting the chalcone of formula 3 to a compound of formula 4 in the presence of an epoxidizing agent or a base;

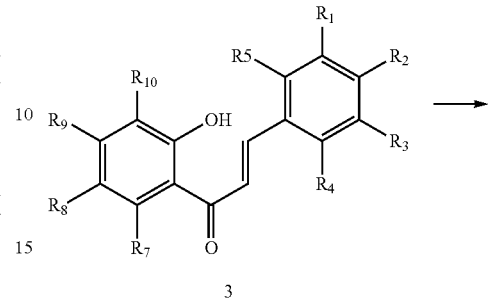

3

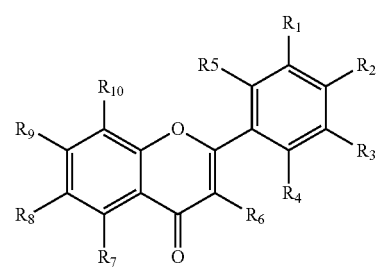

4

(iv) optionally protecting hydroxyl group(s) of the compound obtained in step (iii);

(v) reducing the compounds of step (iii) or step (iv) in the presence of;

a reducing agent to obtain a mixture of 4H-chromene and 2H-chromene compounds of formula 6 and 7;

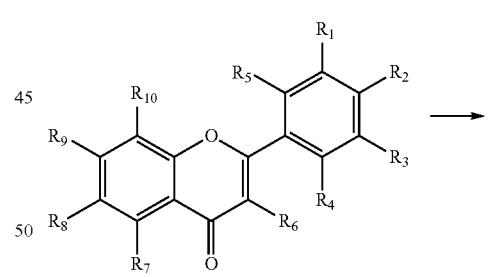

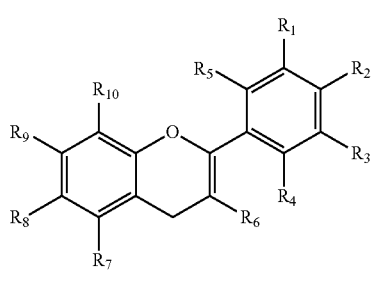

4H-chromene
6

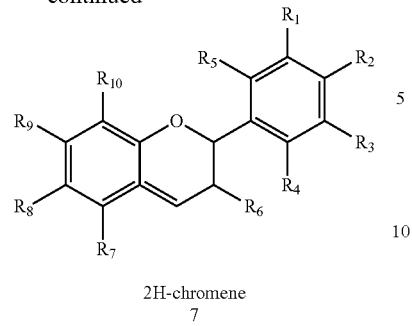

2H-chromene
7 deprotecting 4H-chromene and 2H-chromene compounds obtained in step (v) to obtain the compound of formula I.

2. The process of claim 1, comprising the steps of:

protecting hydroxyl groups of a flavan-3-ol of formula 12 with a protecting agent;

(ii) treating the protected flavan-3-ol of step (i) with an oxidizing agent to obtain a compound of formula 13;

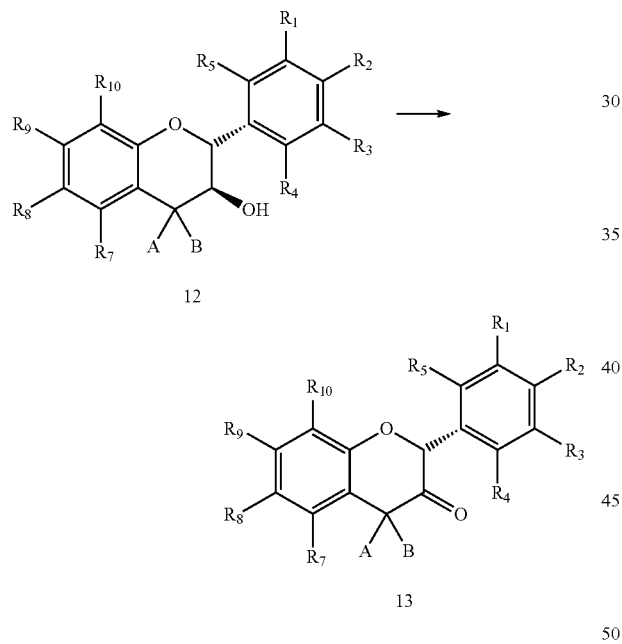

(iii) functionalizing of the oxo group of compound 13 to obtain a compound of formula 14;

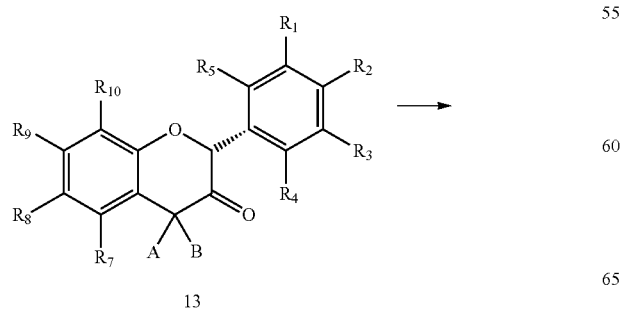

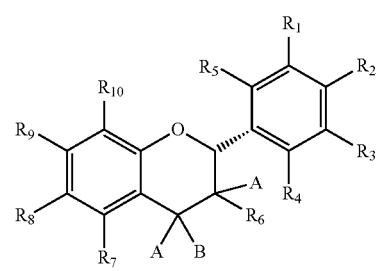

Cis 14
or
Trans 14

(iv) deprotecting the compounds obtained in step (iii) to obtain the compound of formula I.

3. The process of claim 1, comprising the steps of:

(i) optionally protecting hydroxyl groups of a flavan-3-ol of formula 15 with a protecting agent;

(ii) functionalising the hydroxyl group of the compound of formula 15 to obtain a compound of formula 16;

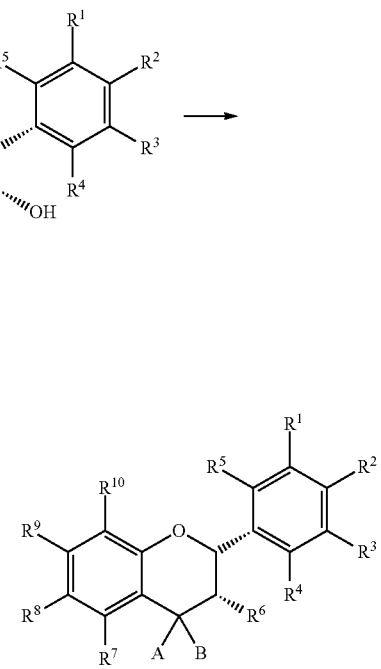

deprotecting the compound of formula 16 to obtain the compound of formula I.

4. The process of claim 1, comprising the steps of:

(i) treating a chalcone of formula 3 with a reducing agent in presence of a solvent at a temperature ranging from ambient to reflux to obtain a compound of formula 10;

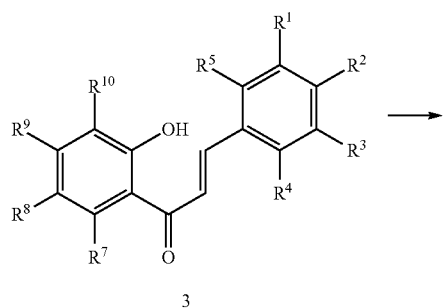

3

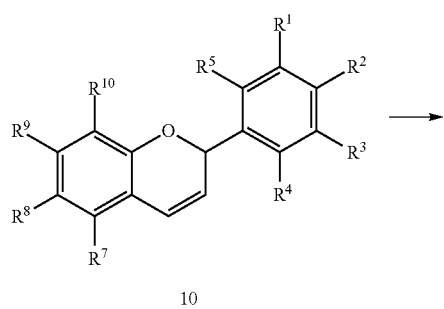

10

(i) converting the compound of formula 10 to a compound of formula 11 in the presence of a hydroxylating agent with or without chiral co-catalysts and a suitable solvent at a temperature ranging from ambient to reflux;

10

11

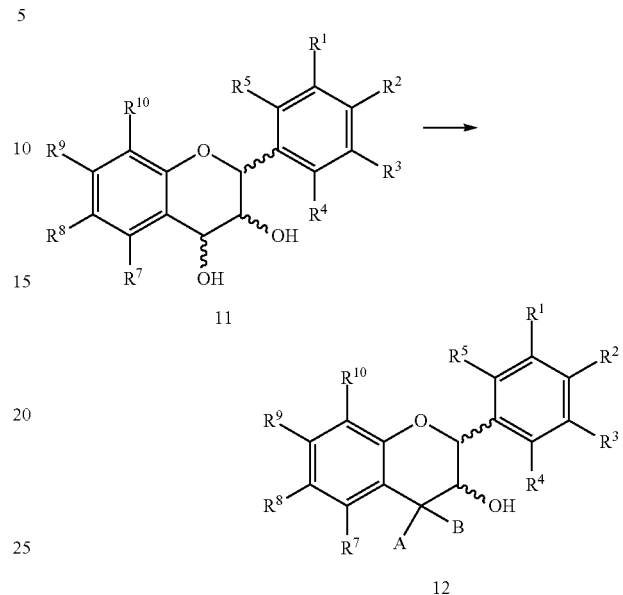

(ii) functionalizing the hydroxyl group of compound of formula 11 with a suitable reagent in the presence of a suitable solvent to obtain a compound of formula 12;

11

12

(iii) treating the compound of formula 12 with an oxidizing agent to obtain a compound of formula 13;

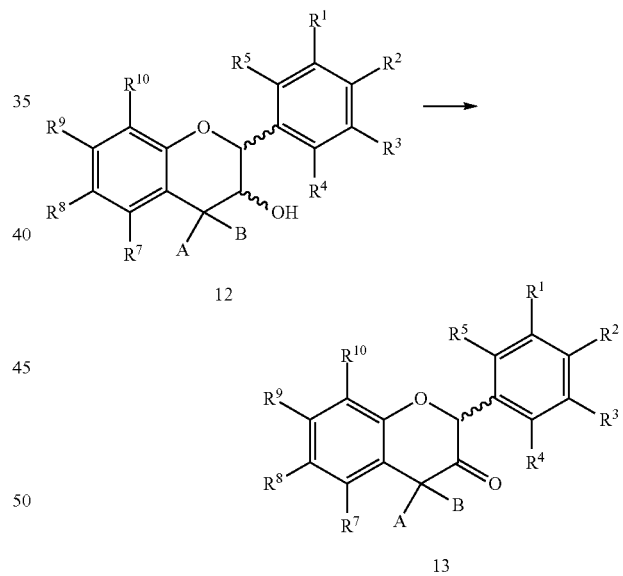

12

13

(iv) reducing the compound of formula 13 from step iv in the presence of a chiral reducing agent at a temperature ranging from −78° C. to room temperature in presence of suitable solvents to obtain the compound of formula I.

5. A compound selected from the group consisting of:
(i) (±) cis 2-(3-hydroxyphenyl)chroman-3,5-diol;
(ii) (±) cis 2-(3-hydroxyphenyl)chroman-3-ol;
(iii) (±) cis 2-phenylchroman-3,5,7-triol;
(iv) (±) cis 2-(3-methoxyphenyl)chroman-3,7-diol;
(x) (±) cis 2-(3-hydroxyphenyl)-7-methoxychroman-3-ol;
(vi) (±) cis 7-methoxy-2-(3-methoxyphenyl)chroman-3-ol;

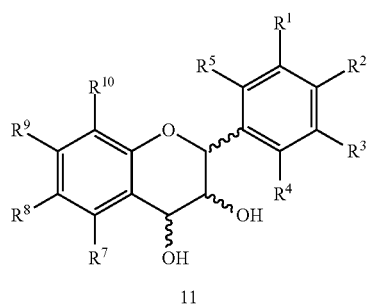

(vii) (±) cis 4-(3,7-dihydroxychroman-2-yl)phenyl acetate;
(viii) (±) cis 3-hydroxy-2-(3-hydroxyphenyl)chroman-7-yl acetate;
(ix) (±) cis 4-(7-acetoxy-3-hydroxychroman-2-yl)phenyl acetate;
(x) 2-(3-methoxy-4-methylphenyl)chromane-3,7-diol;
(xi) 2-(3-hydroxy-4-methylphenyl)chromane-3,7-diol;
(xii) 2-(4-fluoro-3-methoxyphenyl)chromane-3,7-diol;
(xiii) 2-(4-fluoro-3-hydroxyphenyl)chromane-3,7-diol;
(xiv) 2-(3-hydroxyphenyl)-3-propoxychroman-7-ol;
(xv) (2R,3R)-2-(3,4-dihydroxyphenyl)chromane-4,4-d2-3,5,7-triol;
(xvi) (2R,3R)-2-(3,4-dihydroxyphenyl)chromane-2-d-3,5,7-triol;
(xvii) (2R,3R)-2-(3,4-dihydroxyphenyl)chromane-2,4-d2-3,5,7-triol;
(xviii) (2R,3R)-2-(3,4-dihydroxyphenyl)-3-hydroxychromane-5,7-diyl diisobutyl bis(carbonate);
(xix) dibenzyl (4-((2R,3R)-5,7-bis(((benzyloxy)carbonyl)oxy)-3-hydroxychroman-2-yl)-1,2-phenylene) bis(carbonate);
(xx) (2R,3R)-2-(3,4-dihydroxyphenyl)-3-hydroxychromane-5,7-diyl diisobutyl bis(carbonate);
(xxi) (2R,3R)-2-(3,4-dihydroxyphenyl)-3-hydroxychromane-5,7-diyl diethyl bis(carbonate);
(xxii) (2R,3R)-2-(3,4-dihydroxyphenyl)-3-hydroxychromane-5,7-diyl dimethyl bis(carbonate);
(xxiii) dibenzyl (4-((2R,3R)-3-hydroxy-5,7-bis((isobutoxycarbonyl)oxy)chroman-2-yl)-1,2-phenylene) bis(carbonate);
(xxiv) (2R,3R)-2-(3,4-dihydroxyphenyl)-3,7-dihydroxychroman-5-yl heptanoate;
(xxv) (2R,3R)-2-(3,4-dihydroxyphenyl)-3,5-dihydroxychroman-7-yl heptanoate;
(xxvi) (2R,3R)-2-(3,4-dihydroxyphenyl)-3-hydroxychromane-5,7-diyl diheptanoate;
(xxvii) (2R,3R)-2-(3,4-dihydroxyphenyl)-3,7-dihydroxychroman-5-yl octanoate;
(xxviii) (2R,3R)-2-(3,4-dihydroxyphenyl)-3,5-dihydroxychroman-7-yl octanoate;
(xxix) dibenzyl (4-((2R,3R)-3-hydroxy-5,7-bis((methoxycarbonyl)oxy)chroman-2-yl)-1,2-phenylene) bis(carbonate); and
(xxx) (2R,3R)-2-(3-hydroxy-4-methylphenyl)chromane-3,7-diol.

6. A method of increasing exercise tolerance in a subject, comprising administering to the subject the compound of claim 5.

7. A pharmaceutical composition comprising the compound of claim 5 along with a pharmaceutically or nutraceutically-acceptable excipient.

8. The compound of claim 5, when present as its stereoisomer, enantiomer, or pharmaceutically acceptable salt thereof.

9. A compound of Formula (II),

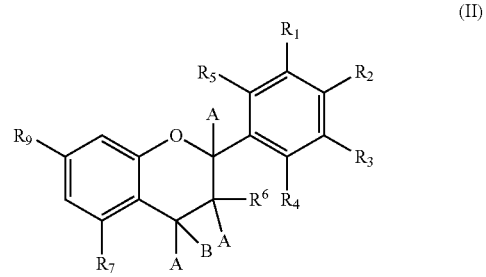

wherein
A and B are hydrogen;
$R^1$, $R^4$ and $R^5$ are H,
at least one of $R^2$, $R^3$, $R^6$, $R^7$ and $R^9$ is —O—(C=O)—$R^{13}$; —O—(C=O)—O—$R^{13}$ or —O—(C=O)—$NR^{11}R^{12}$ wherein $R^{11}$ and $R^{12}$ are $C_{1-6}$ alkyl which may be straight, branched chain or cyclic, or $C_1$-$C_6$ substituted aryl,
$R^{13}$ is $C_1$-$C_6$ substituted aryl, or $C_1$-$C_{12}$ alkyl, which may be straight, branched chain or cyclic,
wherein the remaining $R^2$, $R^3$, $R^6$, $R^7$ and $R^9$ are —OH
wherein substitution at C2 and C3 on the pyran ring is always cis.

10. The compound of claim 9, wherein
A and B are hydrogen;
$R^1$, $R^4$ and $R^5$ are H, $R^2$, $R^3$ and $R^6$ are OH, and
$R^7$ and $R^9$ hydroxyl or —O—(C=O)—$R^{13}$
wherein $R^{13}$ is hydrogen or $C_{1-12}$ alkyl,
wherein at least one of $R^7$ and $R^9$ is —O—(C=O)—$C_{1-12}$ alkyl, and
wherein substitution at C2 and C3 on the pyran ring is always cis.

11. A compound of Formula (II),

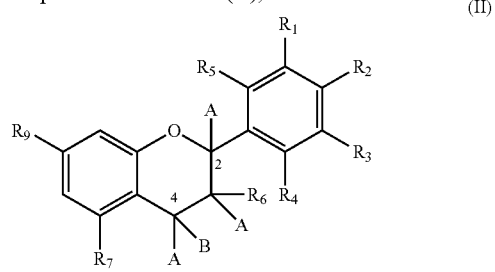

wherein
A and B is independently deuterium or hydrogen and at least one of C2 and C4 is substituted with deuterium;
$R^1$, $R^4$ and $R^5$ are H,
$R^2$, $R^3$, $R^6$, $R^7$ and $R^9$ are —OH
wherein substitution at C2 and C3 on the pyran ring is always cis.

* * * * *